US011448655B2

(12) United States Patent
O'Connell et al.

(10) Patent No.: US 11,448,655 B2
(45) Date of Patent: Sep. 20, 2022

(54) METHOD FOR IDENTIFYING A MODULATOR OF THE TNFα OR CD40L INTERACTION WITH THEIR COGNATE RECEPTORS

(71) Applicant: UCB BIOPHARMA SRL, Brussels (BE)

(72) Inventors: James Philip O'Connell, Slough (GB); John Robert Porter, Slough (GB); Alastair Lawson, Slough (GB); Boris Kroeplien, Slough (GB); Stephen Edward Rapecki, Slough (GB); Timothy John Norman, Slough (GB); Graham John Warrellow, Slough (GB)

(73) Assignee: UCB BIOPHARMA SRL, Brussels (BE)

( * ) Notice: Subject to any disclaimer, the term of this patent is extended or adjusted under 35 U.S.C. 154(b) by 0 days.

(21) Appl. No.: 16/883,859

(22) Filed: May 26, 2020

(65) Prior Publication Data
US 2020/0400678 A1     Dec. 24, 2020

Related U.S. Application Data

(62) Division of application No. 15/736,520, filed as application No. PCT/EP2015/074524 on Oct. 22, 2015, now Pat. No. 10,705,094.

(30) Foreign Application Priority Data

Jun. 18, 2015   (GB) .................................... 1510758

(51) Int. Cl.
| | |
|---|---|
| *G01N 33/68* | (2006.01) |
| *C07K 14/525* | (2006.01) |
| *C07K 16/24* | (2006.01) |
| *A61K 47/64* | (2017.01) |
| *A61P 37/00* | (2006.01) |
| *A61P 35/00* | (2006.01) |
| *C07D 401/14* | (2006.01) |
| *C07D 471/00* | (2006.01) |
| *C07K 14/705* | (2006.01) |
| *C07D 213/72* | (2006.01) |
| *C07D 235/04* | (2006.01) |
| *C07D 239/26* | (2006.01) |
| *C07D 471/04* | (2006.01) |

(52) U.S. Cl.
CPC ..... *G01N 33/6845* (2013.01); *A61K 47/6425* (2017.08); *A61P 35/00* (2018.01); *A61P 37/00* (2018.01); *C07D 213/72* (2013.01); *C07D 235/04* (2013.01); *C07D 239/26* (2013.01); *C07D 401/14* (2013.01); *C07D 471/00* (2013.01); *C07D 471/04* (2013.01); *C07K 14/525* (2013.01); *C07K 14/70575* (2013.01); *C07K 16/241* (2013.01); *G01N 33/6854* (2013.01); *G01N 33/6863* (2013.01); *C07K 2317/55* (2013.01); *C07K 2317/92* (2013.01); *G01N 2333/525* (2013.01); *G01N 2500/02* (2013.01)

(58) Field of Classification Search
None
See application file for complete search history.

(56) References Cited

U.S. PATENT DOCUMENTS

| | | |
|---|---|---|
| 4,908,372 A | 3/1990 | Carr et al. |
| 5,597,899 A | 1/1997 | Banner et al. |
| 7,691,815 B2 | 4/2010 | Liang |
| 7,993,636 B2 | 8/2011 | Mayumi et al. |
| 8,377,441 B2 | 2/2013 | Chang |
| 9,908,944 B2 | 3/2018 | Padkjaer et al. |
| 10,428,148 B2 | 10/2019 | Katagiri et al. |
| 10,705,094 B2 | 7/2020 | O'Connell et al. |
| 10,775,385 B2 | 9/2020 | O'Connell et al. |
| 10,883,996 B2 | 1/2021 | O'Connell et al. |
| 10,969,393 B2 | 4/2021 | O'Connell et al. |
| 11,022,614 B2 | 6/2021 | O'Connell et al. |
| 11,174,311 B2 | 11/2021 | Lawson et al. |
| 2001/0018507 A1 | 8/2001 | Rathjen et al. |
| 2002/0110868 A1 | 8/2002 | Dahiyat et al. |
| 2003/0060461 A1 | 3/2003 | Kodama et al. |
| 2004/0067982 A1 | 4/2004 | Zheng et al. |
| 2006/0222624 A1 | 10/2006 | Bratt et al. |
| 2007/0117755 A1 | 5/2007 | Liang |
| 2009/0022659 A1 | 1/2009 | Olson et al. |
| 2009/0269357 A1 | 10/2009 | Ke et al. |
| 2010/0266613 A1 | 10/2010 | Harding et al. |

(Continued)

FOREIGN PATENT DOCUMENTS

| | | |
|---|---|---|
| CA | 2005053 A1 | 6/1990 |
| CN | 1204230 A | 1/1999 |

(Continued)

OTHER PUBLICATIONS

Final Office Action dated Mar. 9, 2021, issued in U.S. Appl. No. 16/470,999.

(Continued)

*Primary Examiner* — Elly-Gerald Stoica

(74) *Attorney, Agent, or Firm* — Medler Ferro Woodhouse & Mills

(57) ABSTRACT

It has been demonstrated that certain compounds bind to TNF and stabilise a conformation of trimeric TNF that binds to the TNF receptor. Accordingly, these compounds can be used as modulators of TNF. A new assay for identifying compounds with this mechanism of action is also disclosed.

17 Claims, 21 Drawing Sheets

Specification includes a Sequence Listing.

(56) References Cited

U.S. PATENT DOCUMENTS

| | | |
|---|---|---|
| 2010/0297111 A1 | 11/2010 | Beirnaert |
| 2011/0250130 A1 | 10/2011 | Benatuil et al. |
| 2013/0018105 A1 | 1/2013 | Carroll et al. |
| 2014/0112929 A1 | 4/2014 | Batuwangala et al. |
| 2014/0165223 A1 | 6/2014 | Carroll et al. |
| 2021/0088530 A1 | 3/2021 | O'Connell et al. |
| 2021/0132079 A1 | 5/2021 | O'Connell et al. |
| 2021/0140972 A1 | 5/2021 | O'Connell et al. |
| 2022/0025033 A1 | 1/2022 | Lawson et al. |

FOREIGN PATENT DOCUMENTS

| | | |
|---|---|---|
| CN | 1700930 A | 11/2005 |
| CN | 104428293 A | 5/2015 |
| CN | 104619709 A | 5/2015 |
| EP | 0288088 A2 | 10/1988 |
| EP | 0492448 A1 | 1/1992 |
| JP | H0596 A | 1/1993 |
| JP | 2003-040888 A | 2/2003 |
| JP | 2008-539772 A | 11/2008 |
| JP | 2010-172307 A | 8/2010 |
| JP | 2011-519836 A | 7/2011 |
| JP | 2012-509312 A | 4/2012 |
| WO | WO 93/06489 A1 | 4/1993 |
| WO | WO 93/14083 A1 | 7/1993 |
| WO | WO 1994/18325 A1 | 8/1994 |
| WO | WO 1997/22587 A1 | 6/1997 |
| WO | WO 02/098869 A2 | 12/2002 |
| WO | WO 2004/012673 A2 | 2/2004 |
| WO | WO 2006/122786 A2 | 11/2006 |
| WO | WO 2007/060411 A1 | 5/2007 |
| WO | WO 2009/020848 A2 | 8/2008 |
| WO | WO 2008/144753 A2 | 11/2008 |
| WO | WO 2008/144757 A1 | 11/2008 |
| WO | WO 2009/132037 A1 | 10/2009 |
| WO | WO 2009/155723 A2 | 12/2009 |
| WO | WO 2010/058419 A1 | 5/2010 |
| WO | WO 2010/118404 A2 | 10/2010 |
| WO | 2012/078878 A2 | 6/2012 |
| WO | WO 2013/024040 A2 | 2/2013 |
| WO | WO 2013/186229 A1 | 12/2013 |
| WO | WO 2014/001557 A1 | 1/2014 |
| WO | WO 2014/009295 A1 | 1/2014 |
| WO | WO 2014/009296 A1 | 1/2014 |
| WO | WO 2014/040076 A1 | 3/2014 |
| WO | WO 2014/123696 A1 | 8/2014 |
| WO | WO 2014/165223 A1 | 10/2014 |
| WO | WO 2015/086496 A1 | 6/2015 |
| WO | WO 2015/086498 A1 | 6/2015 |
| WO | WO 2015/086499 A1 | 6/2015 |
| WO | WO 2015/086500 A1 | 6/2015 |
| WO | WO 2015/086501 A1 | 6/2015 |
| WO | WO 2015/086502 A1 | 6/2015 |
| WO | WO 2015/086503 A1 | 6/2015 |
| WO | WO 2015/086504 A1 | 6/2015 |
| WO | WO 2015/086505 A1 | 6/2015 |
| WO | WO 2015/086506 A1 | 6/2015 |
| WO | WO 2015/086507 A1 | 6/2015 |
| WO | WO 2015/086508 A1 | 6/2015 |
| WO | WO 2015/086509 A1 | 6/2015 |
| WO | WO 2015/086511 A1 | 6/2015 |
| WO | WO 2015/086512 A1 | 6/2015 |
| WO | WO 2015/086513 A1 | 6/2015 |
| WO | WO 2015/086519 A1 | 6/2015 |
| WO | WO 2015/086520 A1 | 6/2015 |
| WO | WO 2015/086521 A1 | 6/2015 |
| WO | WO 2015/086523 A1 | 6/2015 |
| WO | WO 2015/086525 A1 | 6/2015 |
| WO | WO 2015/086526 A1 | 6/2015 |
| WO | WO 2015/086527 A1 | 6/2015 |
| WO | WO 2016/050975 A1 | 4/2016 |
| WO | WO 2016/149436 A1 | 9/2016 |
| WO | WO 2016/149437 A1 | 9/2016 |
| WO | WO 2016/149439 A1 | 9/2016 |
| WO | WO 2016/168633 A1 | 10/2016 |
| WO | WO 2016/168638 A1 | 10/2016 |
| WO | WO 2016/168641 A1 | 10/2016 |
| WO | WO 2016/198398 A1 | 12/2016 |
| WO | WO 2016/198400 A1 | 12/2016 |
| WO | WO 2016/198401 A1 | 12/2016 |
| WO | WO 2016/202411 A1 | 12/2016 |
| WO | WO 2016/202412 A1 | 12/2016 |
| WO | WO 2016/202413 A1 | 12/2016 |
| WO | WO 2016/202414 A1 | 12/2016 |
| WO | WO 2016/202415 A1 | 12/2016 |
| WO | WO 2017/023902 A1 | 2/2017 |
| WO | WO 2017/023905 A1 | 2/2017 |
| WO | WO 2017/167993 A1 | 10/2017 |
| WO | WO 2017/167994 A1 | 10/2017 |
| WO | WO 2017/167995 A1 | 10/2017 |
| WO | WO 2017/167996 A1 | 10/2017 |

OTHER PUBLICATIONS

Notice of Allowance dated Jul. 14, 2021, issued in U.S. Appl. No. 16/470,999.

References were provided in U.S. Appl. No. 15/742,109, to which this application claims priority.

Alzani et al., "Mechanism of Suramin-Induced Deoligomerization of Tumor Necrosis Factor Alpha," Biochemistry 34:6344-6350 (1995).

Andersen et al., "Prediction of Residues in Discontinuous B-Cell Epitopes using Prtein 3D Structures," Protein Science 15:2558-2567 (2006).

Baldwin et al., "Structural Changes of Tumor Necrosis Factor Alpha Associated with Membrane Insertion and Channel Formation," PNAS 93:1021-1026 (1996).

Cha et al., "High Resolution Crystal Structure of a Human Tumor Necrosis Factor-a Mutant with Low Systemic Toxicity," The Journal of Biological Chemistry 273(4):2153-2160 (1998).

Eck et al., "The Structure of Tumor Necrosis Factor-Alpha at 2.6 A Resolution. Implications for Receptor Binding," Journal of Biological Chemistry 264:17595-17605 (1989).

Fang et al., "TNF: a structure and function relationship," Foreign Medical Immunology, vol. 26, No. 2. (2003). [Machine translation].

Ganesan et al., "Exploratory Computational Assessment of Possible Binding Models for Small Molecule Inhibitors of the CD40-CD154 Co-Stimulatory Interaction," Pharmazie 67:374-379 K2012).

Garcia et al. in: D. Wallach et al. (eds), Advances in TNF Family Research, Advances in Experimental Medicine and Biology 691:187-201 (2011), DOI 10.1007/978-1-4419-6612-4_20.

Grell et al., "The Transmembrane Form of Tumor Necrosis Factor is the Prime Activating Ligand of the 80 kDa Tumor Necrosis Factor Receptor," Cell 83:793-802 (1995).

He et al., "Small-Molecule Inhibition of TN-alpha," Science 310:1022-1025 (2005).

Hoffmann et al., "New Binding Mode to TNF-Alpha Revealed by Ubiquitin-Based Artificial Binding Protein," PLOS One 7:e31298 (2012).

Hu et al., "Comparison of the Inhibition Mechanisms of Adalimumab and Infliximab in Treating Tumor Necrosis Factor alpha-Associated Diseases from the Molecular View," Journal of Biological Chemistry 288:27059-27067 (2013).

Jones et al., "The Structure of Tumor Necrosis Factor—Implications for Biological Function," Journal of Cell Science S13:11-18 (1990).

Kim et al., "Comparative Analyses of Complex Formation and Binding Sites Between Human Tumor Necrosis Factor-Alpha and its Three Antagonists Elucidate Their Different Neutralizing Mechanisms," Journal of Molecular Biology 374(5):1374-1388 (2007).

Liang et al., "Structural Basis for Treating Tumor Necrosis Factor Alpha (TNFalpha)-Associated Diseases with the Therapeutic Antibody Infliximab," Journal of Biological Chemistry 288:13799-13807 (2013).

Lloyd et al., "Modelling the human immune response: performance of a 1O" human antibody repertoire against a broad panel of therapeutically relevant antigens," Protein Engineering, Design & Selection 22(3):159-168 (2009).

(56) References Cited

OTHER PUBLICATIONS

Loetscher et al., "Recombinant 55-kDa Tumor Necrosis Factor (TNF) Receptor," Journal of Biological Chemistry 266:18324-18329 (1991).
Ma et al., "A Novel Small-Molecule Tumor Necrosis Factor Inhibitor Attenuates Inflammation in a Hepatitis Mouse Model," Journal of Biological Chemistry 289:12457-12466 (2014).
Mascarenhas et al., "Are Different Stoichiometries Feasible for Complexes Between Lymphotoxin-alpha and Tumor Necrosis Factor Receptor 1?" BMC Structural Biology 12:8 (2012).
Mukai et al., "Solution of the Structure of the TNF-TNFR2 Complex," Biochemistry 3(148):1-11 (2010).
Nesbitt et al., "Mechanism of Action of Certolizumab Pegol (CDP870): In Vitro Comparison with Other Anti-Tumor Necrosis Factor Alpha Agents," Inflammatory Bowel Diseases 13:1323-1332 (2007).
Sedger et al., "TNF and TNF-receptors: From Mediators of Cell Death and Inflammation to Therapeutic Giants-Past, Present, and Future," Cytokine & Growth Factor Reviews, 25:453-473 (2014).
Shibata et al., "Creation and X-ray Structure Analysis of the Tumor Necrosis Factor Receptor-1-selective Mutant of a Tumor Necrosis Factor-alpha Antagonist," J. Biol. Chem, 283(2): 998-1007 (2008).
Silvian et al., "Small Molecule Inhibition of the TNF Family Cytokine CD40 Ligand through a Subunit Fracture Mechanism," ACS Chemical Biology 6:636-647 (2011).
Simon et al., "Determining Target Engagement in Living Systems," Nature Chemical Biology 9:200-205 (2013).
Sudhamsu et al., "Dimerization of LTBetaR by LTalpha1beta2 is Necessary and Sufficient for Signal Transduction," PNAS 110:19896-19901 (2013).
Tracey et al., "Tumor Necrosis Factor Antagonist Mechanisms of Action: A Comprehensive Review," Pharmacology & Therapeutics 117:244-279 (2007).
Zalevsky et al., "Dominant-Negative Inhibitors of Soluble TNF Attenuate Experimental Arthritis without Suppressing Innate Immunity to Infection," Journal of Immunology 179:1872-1883 (2007).
ZHU et al., "Characterization of the Neutralizing Activity of Three Anti-Human TNF Monoclonal Antibodies and Prediction of their TNF Epitopes by Molecular Modeling and Mutant Protein Approaches," Immunology Letters 102:177-183 (2006).
Non-Final Office Action issued in U.S. Appl. No. 15/736,520, dated Feb. 28, 2019.
Non-Final Office Action issued in U.S. Appl. No. 15/736,336, dated Apr. 24, 2019.
Non-Final Office Action issued in U.S. Appl. No. 15/736,535, dated Apr. 25, 2019.
Non-Final Office Action issued in U.S. Appl. No. 15/736,558, dated Apr. 26, 2019.
Non-Final Office Action issued in U.S. Appl. No. 15/736,614.
Office Action in U.S. Appl. No. 15/736,336 dated Oct. 3, 2019.
Office Action in U.S. Appl. No. 15/736,520 dated Oct. 7, 2019.
Office Action in U.S. Appl. No. 15/736,535 dated Nov. 8, 2019.
Office Action in U.S. Appl. No. 15/736,558 dated Nov. 8, 2019.
Notice of Allowance in U.S. Appl. No. 15/736,614 dated Apr. 6, 2020.
Non-final Office Action in U.S. Appl. No. 15/736,558 dated Apr. 21, 2020.
Non-final Office Action in U.S. Appl. No. 15/736,535 dated May 4, 2020.
Notice of Allowance in U.S. Appl. No. 15/736,336 dated Jun. 4, 2020.
China Nat't IP Search Report in 201580081000.1 dated Aug. 20, 2019.
The International Search Report issued in PCT/EP2015/074491 dated Jan. 13, 2016.
Notice of Allowance dated Jan. 25, 2021, issued in U.S. Appl. No. 15/736,558.
Non-Final Office Action dated Sep. 10, 2020, in U.S. Appl. No. 16/470,999.
Final Rejection dated Oct. 8, 2020, in U.S. Appl. No. 15/736,558.
Notice of Allowance dated Sep. 25, 2020, in U.S. Appl. No. 15/736,535.
Narhi et al., "Induction of α-Helix in the β-Sheet Protein Tumor Necrosis Factor-α: Thermal- and Trifluoroethanol-Induced Denaturation at Neutral pH," Biochemistry 35:11447-11453 (1996).
Fischer et al., "Targeting sTNF/TNFR1 Signaling as a New Therapeutic Strategy," Antibodies 4:48-70 (2015).

Fig. 1
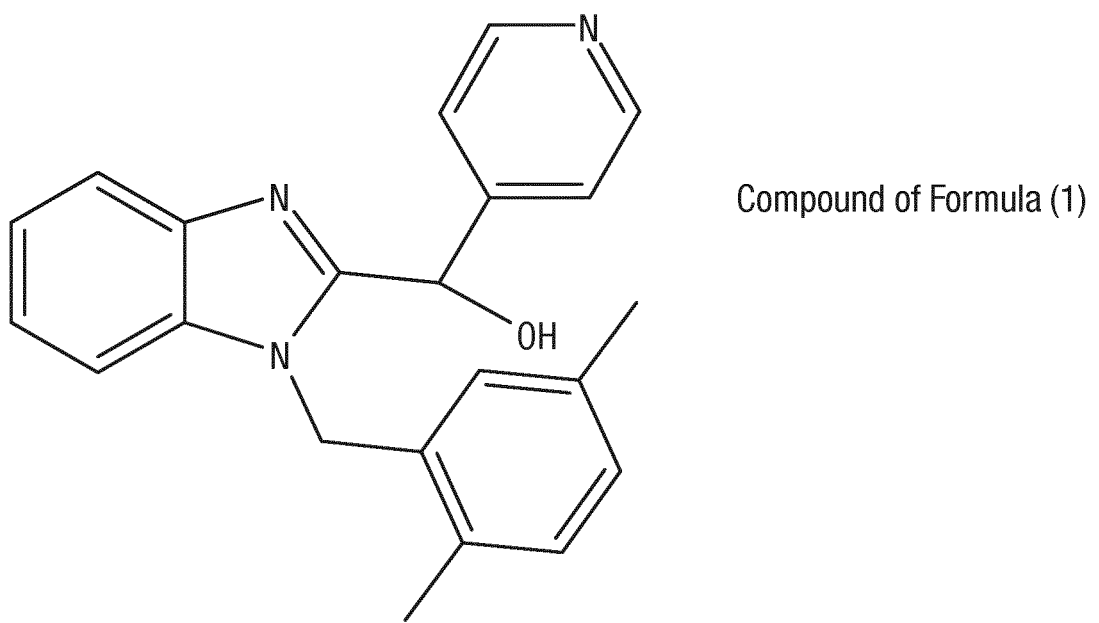
Compound of Formula (1)
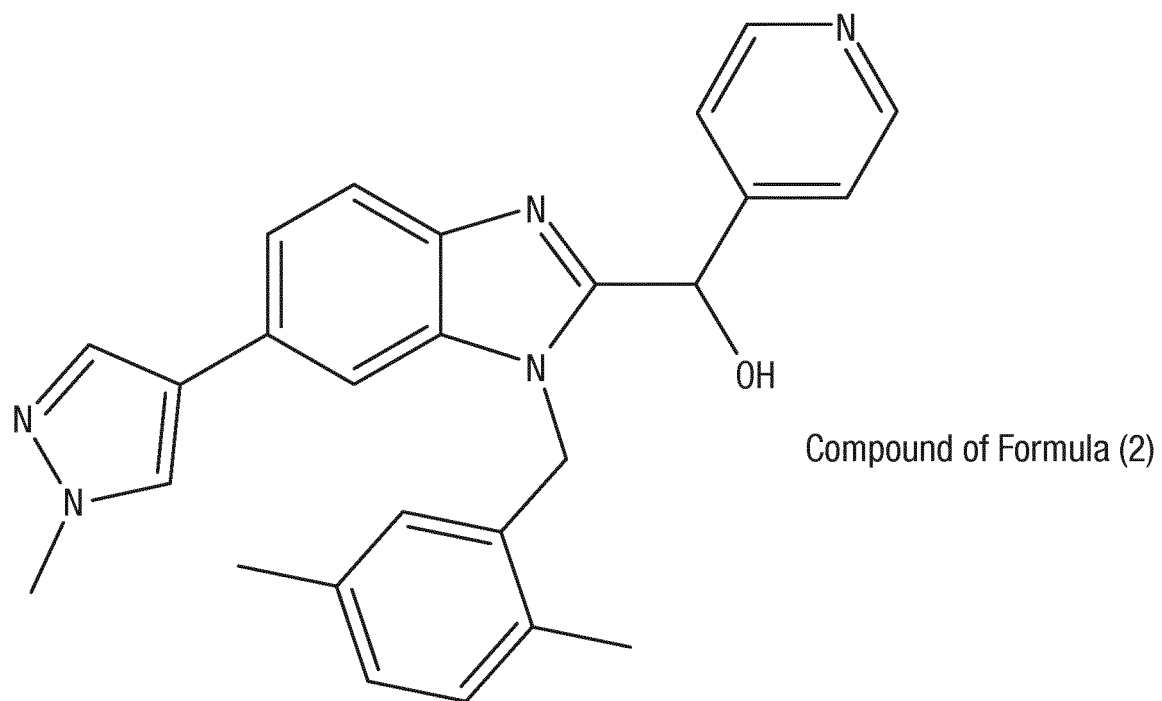
Compound of Formula (2)

Fig. 2
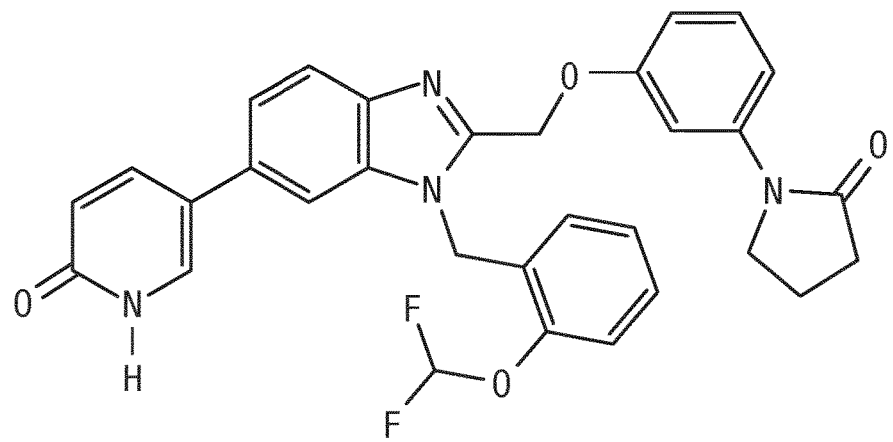
Compound of Formula (3)
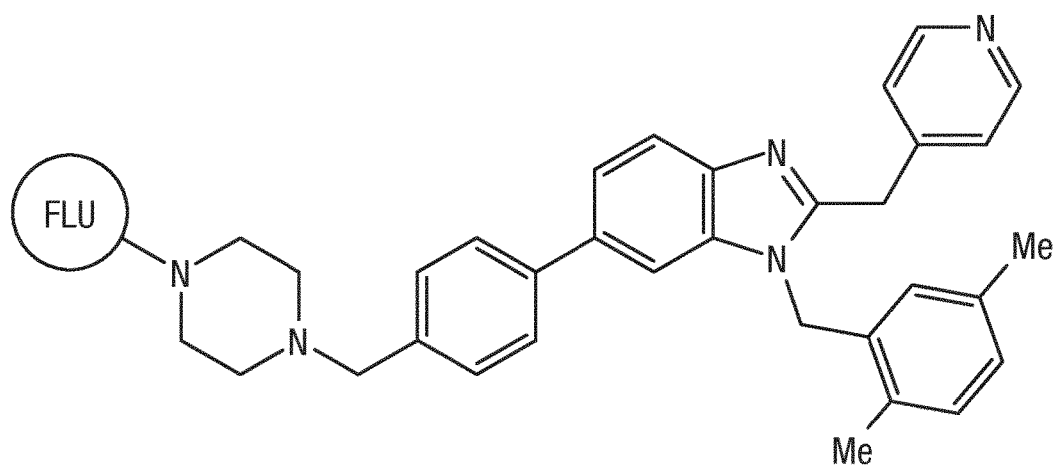
Compound of Formula (4)

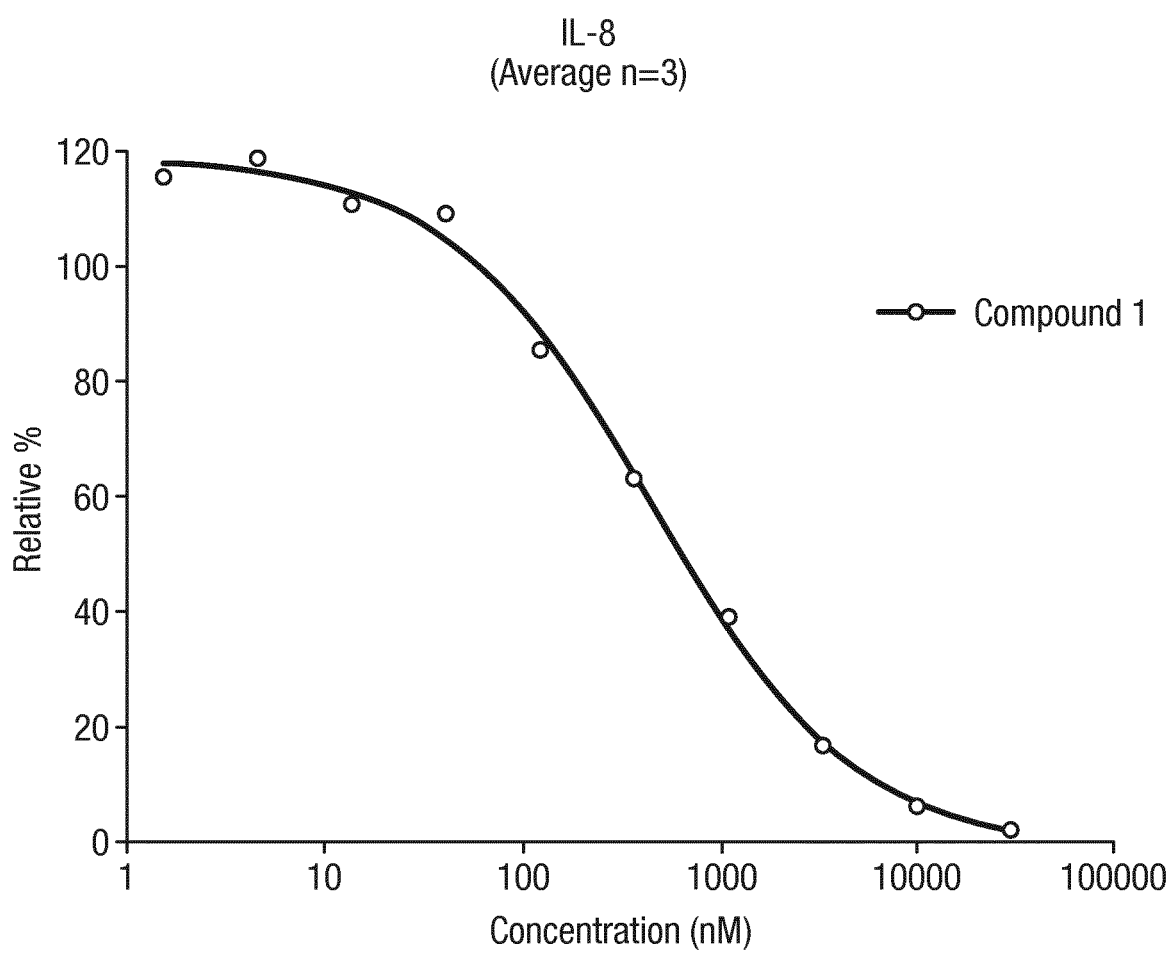

Compound 1 Binding Kinetics (Biacore)

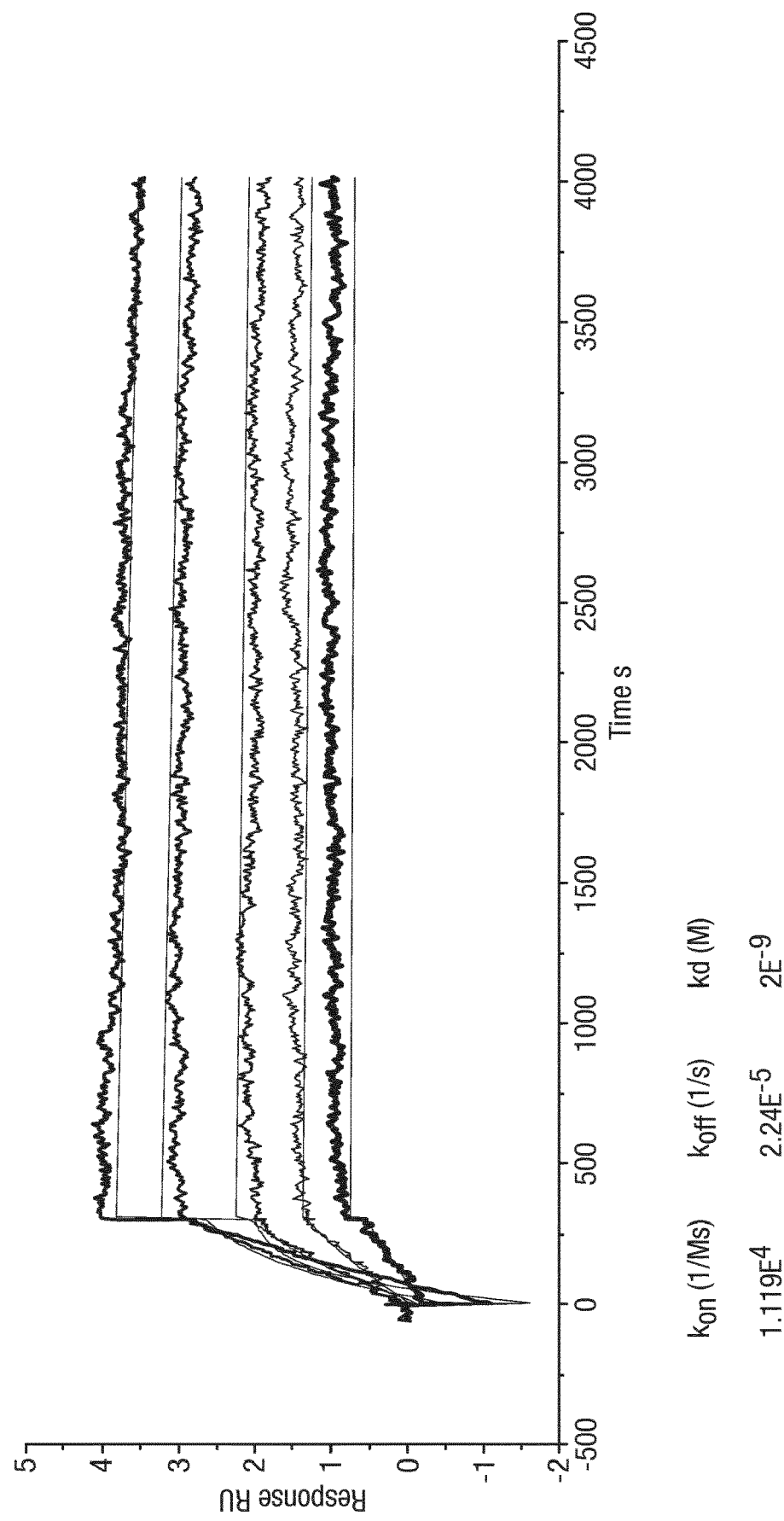

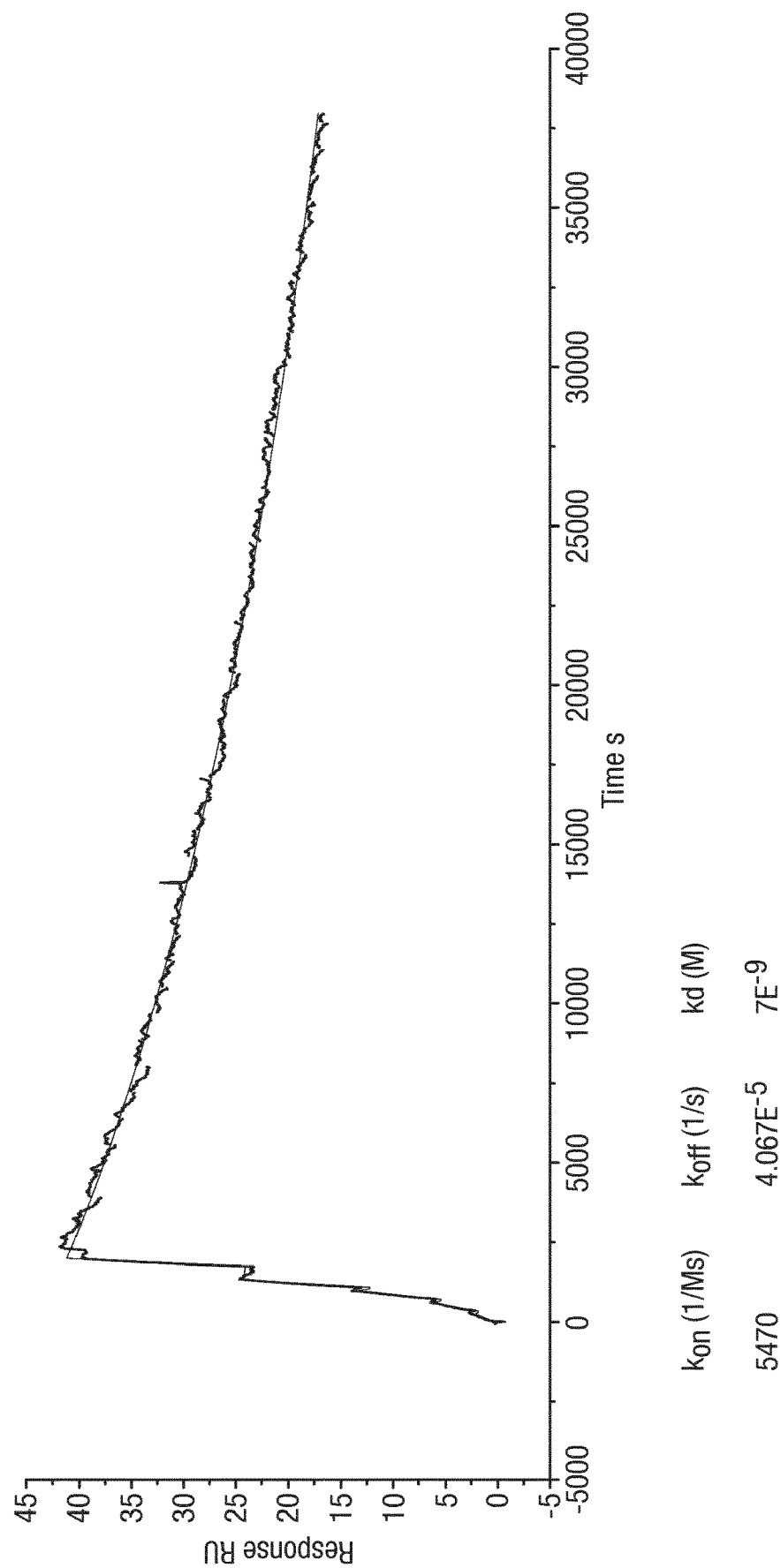

METHOD FOR IDENTIFYING A MODULATOR OF THE TNFα OR CD40L INTERACTION WITH THEIR COGNATE RECEPTORS

REFERENCE TO AN ELECTRONIC SEQUENCE LISTING

The content of the electronic sequence listing (00890004US1seqlist.txt; Size: 16,341 bytes; and Date of Creation Dec. 13, 2017) is herein incorporated by reference in its entirety.

FIELD OF THE INVENTION

This invention relates to modulators of the TNF superfamily. In particular, the invention relates to new small molecule modulators of the TNF superfamily. The present invention also relates to assays for identifying new modulators of the TNF superfamily.

BACKGROUND OF THE INVENTION

The Tumour Necrosis Factor (TNF) superfamily is a family of proteins that share a primary function of regulating cell survival and cell death. Members of the TNF superfamily share a common core motif, which consists of two antiparallel β-pleated sheets with antiparallel β-strands, forming a "jelly roll" β-structure. Another common feature shared by members of the TNF superfamily is the formation of homo- or heterotrimeric complexes. It is these trimeric forms of the TNF superfamily members that bind to, and activate, specific TNF superfamily receptors.

TNFα is the archetypal member of the TNF superfamily. Dysregulation of TNFα production has been implicated in a number of pathological conditions of significant medical importance. For example, TNFα has been implicated in rheumatoid arthritis, inflammatory bowel diseases (including Crohn's disease), psoriasis, Alzheimer's disease (AD), Parkinson's disease (PD), pain, epilepsy, osteoporosis, asthma, systemic lupus erythematosus (SLE) and multiple sclerosis (MS). Other members of the TNF superfamily have also been implicated in pathological conditions, including autoimmune disease.

Conventional antagonists of TNF superfamily members are macromolecular and act by inhibiting the binding of the TNF superfamily member to its receptor. Examples of conventional antagonists include anti-TNFα antibodies, particularly monoclonal antibodies, such as infliximab (Remicade®), adalimumab (Humira®) and certolizumab pegol (Cimzia®), or soluble TNFα receptor fusion proteins, such as etanercept (Enbrel®).

SUMMARY OF THE INVENTION

The present inventors have identified classes of small molecular entities (SME) that modulate TNFα. These compounds act by binding to the homotrimeric form of TNFα, and inducing and stabilising a conformational change in the homotrimer of TNFα. For example, homotrimers of TNFα with the compound bound can bind to TNFα receptors, but are less able, or unable, to initiate signalling downstream of the TNFα receptor. These compounds can be used in the treatment of conditions mediated by TNFα. The present inventors have also developed assays that can identify compounds that are capable of inhibiting TNFα in this manner.

Accordingly, the present invention provides a method for identifying a compound capable of binding to a trimeric protein that is a TNF superfamily member, whereby the compound-trimer complex binds to the requisite TNF superfamily receptor and modulates the signalling of the receptor, comprising:
a) identifying the binding of the compound to the trimeric form of the TNF superfamily member in a sample; and/or
b) measuring the stability of the trimeric form of the TNF superfamily member in a sample comprising the compound; and/or
c) measuring the level of trimeric TNF superfamily member bound to the requisite receptor in a sample comprising the compound; and/or
d) measuring the competition of the compound with a probe compound for binding to the trimeric form of the TNF superfamily member;
and comparing the binding of the compound to the trimeric form of the TNF superfamily member in (a), and/or the stability of the trimeric form of the TNF superfamily member in (b), and/or the level of trimeric TNF superfamily member bound to the requisite receptor in (c), and/or the level of competition observed in (d), to corresponding values from control samples and selecting a compound that is capable of binding to a trimeric protein that is a TNF superfamily member, whereby the compound-trimer complex binds to the requisite TNF superfamily receptor and modulates the signalling of the receptor.

Thus, the methods of the invention may be used to identify a compound that is capable of binding to a trimeric protein that is a TNF superfamily member, whereby the compound-trimer complex binds to the requisite TNF superfamily receptor and modulates the signalling induced by the trimer through the receptor. In other words, the compound-trimer complex in accordance with the invention modulates the signalling of the receptor.

The present invention also provides a complex comprising (or consisting of) a trimeric protein that is a TNF superfamily member and a compound that is bound thereto, whereby the compound-trimer complex binds to the requisite TNF superfamily receptor and modulates the signalling of the receptor.

The present invention also provides a complex comprising a TNF superfamily member and a compound that is capable of binding to a trimeric protein that is a TNF superfamily member, whereby the compound-trimer complex binds to the requisite TNF superfamily receptor and modulates the signalling of the receptor, for use in a method of therapy practised on the human or animal body.

The present invention also provides a pharmaceutical composition comprising a complex of a compound that is capable of binding to a trimeric protein that is a TNF superfamily member, whereby the compound-trimer complex binds to the requisite TNF superfamily receptor and modulates the signalling of the receptor with a trimeric protein that is a TNF superfamily member, and a pharmaceutically acceptable carrier.

BRIEF DESCRIPTION OF THE FIGURES

FIG. 1 shows the structure of a compound of formula (1) and a compound of formula (2).

FIG. 2 shows the structure of a compound of formula (3) and a compound of formula (4).

FIG. 5 (top trace) shows the deconvoluted mass spectrogram of TNFα in a solution containing 10% v/v DMSO. FIG. 5 (middle trace) shows the deconvoluted mass spectrogram of TNFα in a solution containing 10% v/v DMSO and compound of formula (1).

FIG. 11 shows a graph of the concentration of the compound of formula (1) (nM) against % relative IL-8 production in TNFα treated human monocytes.

FIG. 13B shows the binding kinetics for the compound of formula (2) with TNFα. FIG. 13C shows the binding kinetics for the compound of formula (3) with TNFα.

FIG. 17 (middle trace) shows the mass spectrogram of CD40L in a solution containing 10% v/v dimethyl sulfoxide (DMSO). FIG. 17 (top trace) shows the mass spectrogram of CD40L in a solution containing 10% v/v DMSO and the compound of formula (1).

DESCRIPTION OF THE SEQUENCE LISTING

Figure 3A:
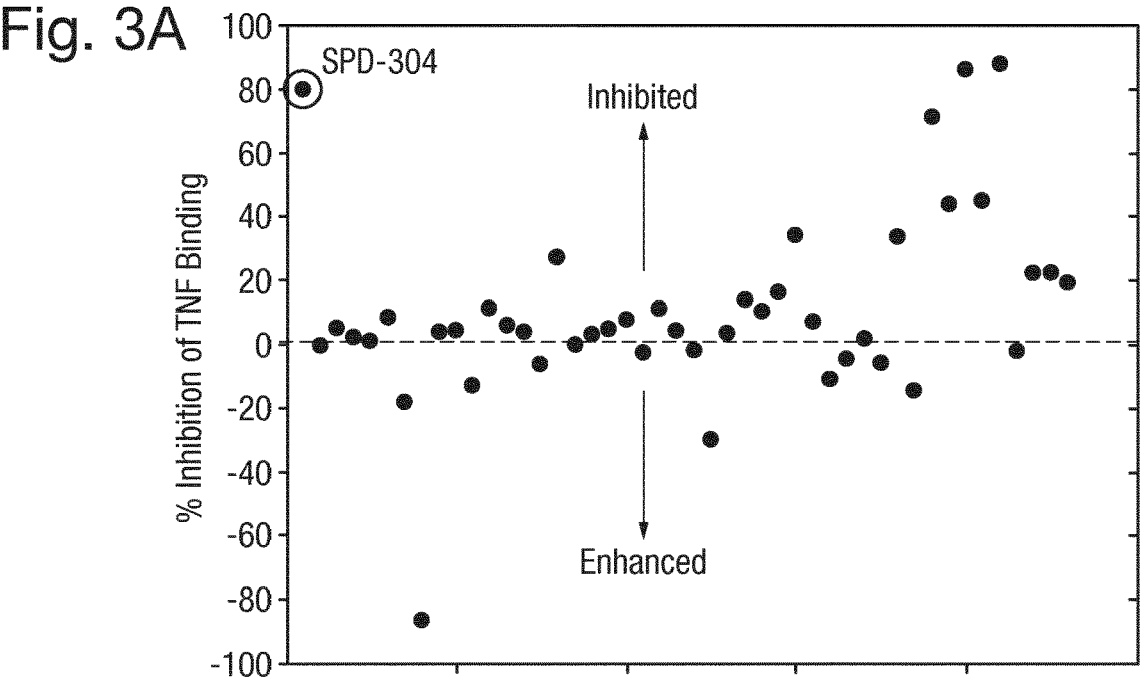
FIG. 3A shows the results of a screen (Mesoscale Discovery assay, MSD) of test compounds that affect the binding of TNFα to the TNF receptor. Multiple test compounds were investigated, and the level of % inhibition of TNFα binding to the TNF receptor calculated.

SEQ ID NO: 1 shows the HCVR of C185_01974.0.
SEQ ID NO: 2 shows the LCVR of C185_01974.0.
SEQ ID NO: 3 shows the amino acid sequence of the mIgG1 heavy chain of C185_01974.0.
SEQ ID NO: 4 shows the amino acid sequence of the kappa light chain of C185_01974.0.
SEQ ID NO: 5 shows the HCVR of C185_01979.0.
SEQ ID NO: 6 shows the LCVR of C185_01979.0.
SEQ ID NO: 7 shows the amino acid sequence of the mIgG1 heavy chain of C185_01979.0.
SEQ ID NO: 8 shows the amino acid sequence of the kappa light chain of C185_01979.0.

DETAILED DESCRIPTION OF THE INVENTION

Assays for Identifying Modulators of TNF Superfamily Members

The present inventors have developed assays for identifying modulators of TNF superfamily members. Modulators of TNF superfamily members may include agonists and antagonists of TNF superfamily members. A modulator of TNF superfamily members may be an antagonist of one or more TNF superfamily members. Alternatively, a modulator of TNF superfamily members may be an agonist of one or more TNF superfamily members. Specifically, the present inventors have developed assays that can be used to identify compounds that bind to trimeric forms of TNF superfamily members, and that stabilise these trimers in a conformation that is capable of binding to the requisite TNF receptor, and so modulate signalling through said receptor. Accordingly, the invention provides assays that are useful for identifying modulators of TNF superfamily members.

In particular, the assays described herein may be used to identify compounds that bind to trimeric forms of TNF superfamily members, and which form a compound-trimer complex which binds to the requisite TNF family receptor.

In a preferred embodiment, the assays of the invention identify compounds that bind to the trimeric form of TNF superfamily members, but not to the monomeric form. In a particularly preferred embodiment, the compounds bind to and stabilise the trimeric form of TNF superfamily members, do not bind to the monomeric form and do not stabilise the dimeric form of the TNF superfamily member. The stabilisation of TNF superfamily trimers by test compounds may occur by the test compound inhibiting the exchange of monomer units between trimers.

Assays of the invention may comprise determining whether a test compound enhances the binding of the TNF superfamily member to its receptor, and hence identify TNF superfamily modulators. In a preferred embodiment, assays of the invention may comprise determining whether a test compound enhances the binding of the TNF superfamily member to its receptor, and hence identify TNF superfamily antagonists which act by increasing the binding of reduced signalling, or non-signalling, forms of TNF superfamily members to their receptors.

Assays for identifying TNF superfamily modulators according to the invention may comprise incubating a sample of the TNF superfamily member of interest under conditions that destabilise the formation of trimers of the TNF superfamily member, for example in the presence of DMSO, and measuring the extent to which a test compound stabilises the formation of TNF superfamily member trimers. Alternatively, assays for identifying TNF superfamily modulators according to the invention may involve binding of TNF superfamily trimers to a test compound, and measuring the extent of binding of the compound-trimer complex to the requisite TNF receptor.

The TNF superfamily members and their receptors may be purified or present in mixtures, such as in cultured cells, tissue samples, body fluids or culture medium. Assays may be developed that are qualitative or quantitative, with the latter being useful for determining the binding parameters (affinity constants and kinetics) of the test compound to trimeric forms of TNF superfamily members, and also of the binding parameters of the compound-trimer complex to the requisite TNF receptor.

The amount of the monomeric, dimeric and trimeric forms of the TNF superfamily members may be determined by measuring the mass of the monomeric, dimeric and trimeric forms, the molar amount of the monomeric, dimeric and trimeric forms, the concentration of the monomeric, dimeric and trimeric forms, and the molarity of the monomeric, dimeric and trimeric forms. This amount may be given in any appropriate units. For example, the concentration of the monomeric, dimeric and trimeric forms may be given in pg/ml, ng/ml or µg/ml. The mass of the monomeric, dimeric and trimeric forms may be given in pg, ng or µg.

The amount of the monomeric, dimeric or trimeric forms of a TNF superfamily member in a sample of interest may be compared with the level of the monomeric, dimeric or trimeric forms of a TNF superfamily member in another sample, such as a control sample, as described herein. In such a method, the actual amount of the monomeric, dimeric or trimeric forms of a TNF superfamily member, such as the mass, molar amount, concentration or molarity of the monomeric, dimeric or trimeric forms of a TNF superfamily member in the samples may be assessed. The amount of the monomeric, dimeric or trimeric forms of a TNF superfamily member may be compared with that in another sample without quantifying the mass, molar amount, concentration or molarity of the monomeric, dimeric or trimeric forms of a TNF superfamily member. Thus, the amount of the monomeric, dimeric or trimeric forms of a TNF superfamily member in a sample according to the invention may be assessed as a relative amount, such as a relative mass, relative molar amount, relative concentration or relative molarity of the monomeric, dimeric or trimeric forms of a TNF superfamily member based on a comparison between two or more samples.

In the present invention, libraries of compounds may be screened in order to identify modulators of TNF superfamily members (i.e. using the assays disclosed herein). Such libraries typically comprise at least 260 compounds. Preferably, such libraries comprise at least 300, at least 500 or even at least 1000 compounds.

Mass Spectrometry Based Assays

The present inventors have found that mass spectrometry may be used to identify compounds that bind to trimeric forms of TNF superfamily members and that stabilise these trimers in a conformation that is capable of binding to the requisite TNF receptor.

In particular, mass spectrometry may be used to assess whether a compound stabilises the trimeric form of TNF superfamily members.

Accordingly, the invention provides an assay for identifying a compound that is capable of binding to a trimeric protein that is a TNF superfamily member, whereby the compound-trimer complex binds to the requisite TNF superfamily receptor and modulates the signalling of the receptor comprising the steps of identifying the binding of a test compound to the trimeric form of the TNF superfamily member in a sample and comparing the binding of the compound to the trimeric form of the TNF superfamily member to corresponding values from control samples, which comprises conducting a mass spectrometric analysis on a sample containing the TNF superfamily member and the compound to detect the amount of the TNF superfamily member trimer and comparing the amount of TNF superfamily member trimer in the sample with a control sample and selecting a compound that is capable of binding to the trimeric form of the TNF superfamily member, whereby the compound-trimer complex binds to the requisite TNF superfamily receptor and modulates the signalling of the receptor. The control sample may be identical to the sample being assayed, except that it lacks the test compound. The sample comprising the TNF superfamily member and the compound may further comprise a destabilising agent.

In the present invention, a test compound may be added to a solution of a TNF superfamily member in the presence of a destabilising agent. Destabilising agents, also known as chaotropes, include low molar concentrations (e.g. 1M) of urea, guanidine or acetonitrile, high concentrations (e.g. 6M or higher) of these reagents will result in complete dissociation of the TNFα trimer and unfolding of the constituent TNFα monomeric subunits. The destabilising agent is preferably DMSO, typically at a concentration of 5%, 10% or higher. The resulting solution may be analysed using mass spectrometry.

Non-covalent complexes formed between TNF superfamily members and test compounds with binding affinities as weak as 1 mM can be detected. Binding stoichiometry may be obtained directly from presence or absence of complexes in which multiple molecules of the test compound are bound. Binding affinities ($K_D$ values) can be determined by measuring the TNF superfamily member—test compound complex (compound-trimer complex)/TNF superfamily member concentration ratio at known test compound concentrations.

The test compound stabilises the trimeric form of the TNF superfamily member if it increases the proportion of trimer compared to the amount of trimer observed for a sample containing the TNF superfamily member and the destabilising agent in the absence of the test compound. The test compound may increase the amount of trimer by 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400% or more compared to the amount of trimer present in a sample containing the TNF superfamily member and the destabilising agent in the absence of the test compound.

The test compound may also increase the amount of trimer compared to that observed for a sample of the TNF superfamily member in the absence of both the destabilising agent and the test compound. The test compound may increase the amount of trimer by 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400% or more compared to the amount of trimer present in a sample containing the TNF superfamily member in the absence of both the destabilising agent and the test compound.

Trimer stabilisation is evidenced in two ways in the mass spectrometric study.

First there is the physical dissociation of the TNFα trimer complex which can be measured by the ratio of monomer and trimer observed in the mass spectrum. The dimeric species is not observed in our studies. This dissociation may be an artefact of the high energy process used to introduce molecules into the mass spectrometer. None-the-less it can be used to assess the ability of the test compounds to stabilise the trimeric complex during the nebulisation and ionisation processes and thereby reduce the amount of monomer observed in the mass spectrum, the monomer/trimer ratio being used to determine the degree of stabilisation.

Second, under soft ionisation conditions less energy is imparted to the trimeric complex resulting in its intact transmission into the spectrometer thereby more closely reflecting the true solution composition. The electrospray ionisation process results in multiple charging of proteins because, in positive ionisation mode, basic functional groups within certain amino acids acquire a positive charge. Mass spectrometers measure the mass/charge ratio. Therefore, for example a nominally 52,000 Da TNFα trimer will appear at an m/z ratio of 5,200 if it is carrying 10 charges. It is this multiple charging effect that permits spectrometers with a limited mass range to be used in the study of multimeric protein complexes. Software supplied with the spectrometer allow the user to deconvolute the data to give the mass of the protein as it would appear if it was to carry just a single charge (i.e. its true molecular weight based on its atomic composition).

In folded proteins where many amino acids are buried in the core with only a percentage exposed on the surface typically 6 to 8 positive charges are acquired. No one single charged species predominates, often several species (ions) are observed within a small range, these comprise what is known as the charge state envelope. At the other extreme, where a protein is totally denatured (i.e. unfolded) then many more amino acids are exposed and the typical number of charges acquired may be as high as 20, the charge state envelope also comprises a larger number of charged species as statistically there are now more available sites to accept a charge. Thus the number of charges and the number of charged species comprising the charge state envelope are sensitive readouts on the degree of protein folding. Further, if a folded protein can exist in multiple conformations which differ in the relative number of surface exposed amino acids then shifts in the charge state envelope will reflect these differences.

Under soft nano-electrospray ionisation conditions, mass spectrometric studies of intact, folded TNFα protein show that almost 100% of the TNFα trimer is detected, very little of the TNFα monomer is detected whilst the dimeric species is completely absent.

Under harsher ionization conditions, or when a destabilising agent is added to the TNFα sample, increased levels of the monomeric TNFα are observed with a concomitant reduction in the levels of the trimer. Only a very small quantity of dimer is observed.

Mass spectrometry may also be used to determine whether the test compound binds to the monomeric, dimeric and trimeric forms of the TNF superfamily member.

Mass spectrometry may also be used to determine the stoichiometry of the test compounds with TNF superfamily members, i.e. how many molecules of the test compound bind to the TNF superfamily member.

Mass spectrometry may also be used to determine whether the compound—TNF superfamily member trimer complex binds to the requisite TNF receptor.

Mass spectrometry may also be used to measure the rates at which a test compound binds to a TNF superfamily member (the "on" rate" $k_{on-c}$) and rate at which the test compound dissociates from the TNF superfamily member (the "off" rate or $k_{off-c}$). As used herein, the symbol "$K_{D-c}$" denotes the binding affinity (dissociation constant) of a test compound for a TNF superfamily member. $K_{D-c}$ is defined as $k_{off-c}/k_{on-c}$. Test compounds may have slow "on" rates, which can be measured in minutes by mass spectral analysis of the TNF superfamily member and compound-trimer complex peak intensities. $K_{D-c}$ values for a test compound can be estimated by repeating this measurement at different TNF superfamily member: compound-trimer complex ratios. In a preferred embodiment, binding of compounds of the invention to TNF superfamily trimers is characterized by fast "on" rates, ideally about $10^7$ $M^{-1}$ $s^{-1}$, with slow "off" rate, for example values typically of $10^{-3}$ $s^{-1}$, $10^{-4}$ $s^{-1}$, or no measurable "off" rate.

Mass spectrometry may also be used to determine whether the test compound binds to the TNF superfamily member in the presence of the requisite receptor. This may involve incubating the test compound with a TNF superfamily member that has been pre-incubated with its receptor. The sample containing the test compound, and pre-incubated TNF superfamily member and receptor can then be fractionated to separate molecules according to their molecular size, for example by analytical gel filtration. The resulting fractions may be analysed using mass spectrometry to determine whether the test compound binds to the TNF superfamily member in the presence of the requisite receptor. The compound will elute in the same fraction as the TNF superfamily member if it is bound to the TNF superfamily member. The compound will elute in a different fraction than the TNF superfamily member if it is not bound to the TNF superfamily member. In this case the compound will typically elute in a later gel filtration fraction than the TNF superfamily member.

Mass spectrometric methods may include, for example, matrix-assisted laser desorption/ionization mass spectrometry (MALDI MS), surface-enhanced laser desorption/ionization mass spectrometry (SELDI MS), time of flight mass spectrometry (TOF MS) and liquid chromatography mass spectrometry (LC MS).

Receptor-Ligand Binding Assays

Conventional TNF superfamily antagonists act by inhibiting the binding of the TNF superfamily member to its receptor. The present inventors have used receptor-ligand binding assays to determine whether a test compound enhances the binding of the TNF superfamily member to its receptor. Such receptor-ligand binding assays may be used to hence identify TNF superfamily antagonists which act by increasing the binding of reduced-signalling, or non-signalling, forms of TNF superfamily members to their receptors. Receptor-ligand binding assays may also be used to hence identify agonists which act by increasing the binding of TNF superfamily members to their receptors and enhance signalling by TNF superfamily receptors.

Accordingly, the invention provides an assay for identifying a compound that is capable of binding to a trimeric protein that is a TNF superfamily member, whereby the compound-trimer complex binds to the requisite TNF superfamily receptor and modulates the signalling of the receptor comprising the step of measuring the level of trimeric TNF superfamily member bound to the requisite receptor in a sample comprising a test compound and comparing the level of trimeric TNF superfamily member bound to the requisite receptor to corresponding values from control samples, which comprises performing a receptor-ligand binding assay in which a sample of TNF superfamily member and the compound, is applied to the requisite TNF receptor that has been bound to a surface and comparing the amount of TNF superfamily member trimer bound to the requisite TNF receptor with a control sample and selecting a compound that is capable of binding to the trimeric form of the TNF superfamily member, whereby the compound-trimer complex binds to the requisite TNF superfamily receptor and modulates the signalling of the receptor. The control sample may be identical to the sample being assayed, except that it lacks the test compound and/or it contains a known compound. The sample comprising the TNF superfamily member and the compound may further comprise a destabilising agent.

A test compound may be added to a solution comprising a TNF superfamily member and destabilising agent. The level of binding of the TNF superfamily receptor in the presence of the destabilising agent alone (in a control sample) can be compared with the level of binding of the TNF superfamily member to its receptor in the presence of the destabilising agent and the test compound. The test compound enhances the binding of the TNF superfamily member to its receptor if it increases the proportion of the TNF superfamily member bound to its receptor compared to the level of binding of the TNF superfamily member to its receptor observed for a sample containing the TNF superfamily member and the destabilising agent in the absence of the test compound.

The test compound may increase the amount of the TNF superfamily member bound to its receptor by 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400% or more compared to the amount of the TNF superfamily member bound to its receptor in a sample containing the TNF superfamily member in the absence of the test compound.

The receptor-ligand binding assay of the invention typically requires a TNF superfamily receptor bound to a support. The TNF superfamily receptor may be bound directly to the support, or indirectly, using a linker molecule, such as avidin or streptavidin. The level of binding of the TNF superfamily member to its receptor can then be assayed by adding a solution of the TNF superfamily member with a destabilising agent. Destabilising agents, also known as chaotropes, include low molar concentrations (e.g. 1M) of urea, guanidine or acetonitrile, high concentrations (e.g. 6M or higher) of these reagents will result in complete dissociation of the TNFα trimer and unfolding of the constituent TNFα monomeric subunits. The destabilising agent is preferably DMSO, typically at a concentration of 5%, 10% or higher.

Binding of TNF superfamily member to its receptor is typically determined using an antibody that is specific to the TNF superfamily member and which is bound to a marker. The marker can be any molecule that can be detected. For example, the marker can be a radioactive isotope (for example $^{125}I$, $^{32}P$, $^{35}S$ and $^{3}H$), fluorescent dye (for example fluorescein, rhodamine), enzyme-conjugate and the like. A substrate for the enzyme is used to quantify the amount of the TNF superfamily member bound to the surface-bound receptor. Other markers include molecular labels that can be activated to produce light on exposure to certain stimuli, such as electricity. The choice of a marker will depend upon the detection system used.

Receptor-ligand binding assays may be carried out in several formats, including cell-based binding assays, solution-phase assays and immunoassays. The solid supports for receptor-ligand binding reactions preferably contain wells. In general, test compound-trimer complexes are incubated with the requisite TNF superfamily receptor for a specified period of time followed by measurement of the amount of the compound-trimer complex that is bound to the receptor. The level of bound compound-trimer complex may be calculated by measuring the marker using microscopy, fluorimetry, a scintillation counter, or any available immunoassay.

As used herein, the symbol "$k_{on-r}$" denotes the rate (the "on" rate) at which a compound-trimer complex binds to a TNF superfamily receptor. As used herein, the symbol "$k_{off-r}$" denotes the rate (the "off" rate) at which a compound-trimer complex dissociates from a TNF superfamily receptor. As used herein, the symbol "$K_{D-r}$" denotes the binding affinity (dissociation constant) of a compound-trimer complex for a superfamily receptor. $K_{D-r}$ is defined as $k_{off-r}/k_{on-r}$.

Receptor-ligand binding assays may be used to measure the binding affinity of the compound-trimer complexes of the invention to the requisite TNF superfamily receptor. In particular, competition assays may be used to compare the $k_{on-r}$ and $k_{off-r}$ values for compound-trimer complexes of the invention to the requisite TNF superfamily receptor and the $k_{on-r}$ and $k_{off-r}$ values of the TNF superfamily member binding to its receptor in the absence of the test compound, and to determine $K_{D-r}$ values for binding of compound-trimer complexes of the invention to the requisite TNF superfamily receptor.

Stability Assays

The present inventors have developed methods for determining the effect of test compounds on the stability of TNF superfamily members. Accordingly, the invention provides an assay for identifying a compound that is capable of binding to a trimeric protein that is a TNF superfamily member, whereby the compound-trimer complex binds to the requisite TNF superfamily receptor and modulates the signalling of the receptorcomprising the step of measuring the stability of the trimeric form of the TNF superfamily member in a sample comprising the compound and comparing the stability of the trimeric form of the TNF superfamily member to corresponding values from control samples, which comprises performing an assay to determine the $T_m$ of the trimeric form of the TNF superfamily member in a sample of the TNF superfamily member and the compound, comparing the $T_m$ of the trimeric form of the TNF superfamily member with a control sample and selecting a compound that is capable of binding to the trimeric form of the TNF superfamily member, whereby the compound-trimer complex binds to the requisite TNF superfamily receptor and modulates the signalling of the receptor. The control sample may be identical to the sample being assayed, except that it lacks the test compound and/or it contains a known compound. The sample comprising the TNF superfamily member and the compound may further comprise a destabilising agent.

A test compound may be added to a solution comprising a TNF superfamily member and destabilising agent. The stability of the trimeric form of the TNF superfamily member in the presence of the destabilising agent alone (in a control sample) can be compared with the stability of the trimeric form of the TNF superfamily member in the presence of the destabilising agent and the test compound. The test compound enhances the stability of the trimeric form of the TNF superfamily member if it increases the thermal transition midpoint ($T_m$) of the trimeric form of the TNF superfamily member compared to the $T_m$ of the trimeric form of the TNF superfamily member observed for a sample containing the TNF superfamily member and the destabilising agent in the absence of the test compound. The $T_m$ of the trimeric form of the TNF superfamily member is the temperature at which 50% of the biomolecules are unfolded. The $T_m$ of the trimeric form of the TNF superfamily member in the presence and/or absence of the test compound may be measured using any appropriate technique known in the art, for example using differential scanning calorimetry (DSC) or fluorescence probed thermal denaturation assays.

The test compound may increase the $T_m$ of the trimeric form of the TNF superfamily member by at least 1° C., at least 2° C., at least 5° C., at least 10° C., at least 15° C., at least 20° C. or more compared to the $T_m$ of the trimeric form of the TNF superfamily member in a sample containing the TNF superfamily member in the absence of the test compound. Preferably the test compound increases the $T_m$ of the trimeric form of the TNF superfamily member by at least 1° C., more preferably by at least 10° C. and even more preferably by between 10° C. and 20° C.

Destabilising agents, also known as chaotropes, include low molar concentrations (e.g. 1M) of urea, guanidine or acetonitrile, high concentrations (e.g. 6M or higher) of these reagents will result in complete dissociation of the TNFα trimer and unfolding of the constituent TNFα monomeric subunits. The destabilising agent is preferably DMSO, typically at a concentration of 5%, 10% or higher.

Isothermal Calorimetry Assays

The present inventors have developed isothermal calorimetry methods for determining the effect of test compounds on the binding affinity of TNF superfamily members for their receptors.

Accordingly, the invention provides an assay for identifying a compound capable of binding to a trimeric protein that is a TNF superfamily member, whereby the compound-trimer complex binds to the requisite TNF superfamily receptor and modulates the signalling of the receptorcomprising the step of measuring the level of trimeric TNF superfamily member bound to the requisite receptor in a sample comprising the compound and comparing the level of trimeric TNF superfamily member bound to the requisite receptor to corresponding values from control samples, which comprises performing an isothermal calorimetric analysis to measure the binding affinity of the TNF superfamily member for the requisite receptor in the presence of the compound; and comparing the binding affinity of the TNF superfamily member for the requisite receptor with a control sample and selecting a compound capable of binding to a trimeric protein that is a TNF superfamily member, whereby the compound-trimer complex binds to the requisite TNF superfamily receptor and modulates the signalling of the receptor. The control sample may be identical to the sample being assayed, except that it lacks the test compound and/or it contains a known compound.

Aliquots of a TNF superfamily member may be added sequentially to a reservoir of the requisite TNF receptor. The volume of the aliquots may be in any appropriate range. The aliquots may be of any appropriate volume, such as from 0.1 µl to 10 µl. In a preferred embodiment the aliquots may be 0.5 µl, 1.0 µl, or 3.0 µl in volume. It may be possible to use larger volumes depending on the syringe volume.

Each addition of the TNF superfamily member will result in the release or absorption of a small amount of heat as the TNF superfamily trimers bind to the receptor. Typically, each addition of the TNF superfamily member will result in the release of a small amount of heat as the TNF superfamily trimers bind to the receptor. The amount of heat release can be measured using isothermal calorimetry, and this information used to obtain the binding affinity of the TNF superfamily member with its receptor.

This process can be repeated using sequential additions of a solution comprising a TNF superfamily member and a test compound to a reservoir of the TNF superfamily receptor. Preferably the TNF superfamily member and test compound will be in the form of a compound-trimer complex. Again, the amount of heat release can be measured using isothermal calorimetry, and this information used to obtain the binding affinity of the TNF superfamily member with its receptor.

The binding affinities of the TNF superfamily member and compound-trimer complex may be compared to determine whether the compound increases the binding affinity of the TNF superfamily member to its receptor.

The test compound may increase the binding affinity of the TNF superfamily member to its receptor by 2 times, 3 times, 4 times, 5 times, 10 times, 20 times, 30 times, 40 times, 50 times, 60 times, 70 times, 80 times, 90 times, 100 times or more compared to the binding affinity of the TNF superfamily member to its receptor in the absence of the test compound.

The binding affinity may be given in terms of binding affinities ($K_{D-r}$) and may be given in any appropriate units, such as µM, nM or pM. The smaller the $K_{D-r}$ value, the larger the binding affinity of the TNF superfamily member to its receptor.

The $K_{D-r}$ value of the TNF superfamily member for binding to its receptor in the presence of the test compound may be at least 1.5 times, 2 times, 3 times, 4 times, 5 times, 10 times, 20 times, 30 times, 40 times, 50 times, 60 times, 70 times, 80 times, 90 times, 100 times lower than the $K_{D-r}$ value of the TNF superfamily member for binding to its receptor in the absence of the test compound.

The $K_{D-r}$ value of the TNF superfamily member for binding to its receptor in the presence of the test compound may be 1 µM, 100 nM, 10 nM, 5 nM, 1 nM, 100 pM, 10 pM or less. In a preferred embodiment the $K_{D-r}$ value of the TNF superfamily member for binding to its receptor in the presence of the test compound is 1 nM or less.

Competition Assays

The present inventors have developed methods for identifying compounds that are capable of binding to a trimeric protein that is a TNF superfamily member, whereby the compound-trimer complex binds to the requisite TNF superfamily receptor and modulates the signalling of the receptor by investigating the ability of a test compound to compete with a probe compound for binding to a trimeric TNF superfamily member. Accordingly, the invention provides an assay which comprises measuring the competition of a test compound with a probe compound for binding to the trimeric form of the TNF superfamily member and comparing the level of competition thereby observed to corresponding values from control samples and selecting a compound that is capable of binding to a trimeric protein that is a TNF superfamily member, whereby the compound-trimer complex binds to the requisite TNF superfamily receptor and modulates the signalling of the receptor.

The probe compound may comprise a compound in accordance with the invention that is radiolabelled. Radionuclei that may be used in the probes of the present invention include tritium ($^{3}$H), $^{14}$C, $^{18}$F, $^{22}$Na, $^{32}$F, $^{33}$F, $^{35}$S, $^{36}$Cl, $^{125}$I, $^{131}$I and $^{99m}$Tc.

In particular, the competition assay may be a fluorescence polarization (FP) assay, where the degree of fluorescence polarization is related to the rotational relaxation time of a fluorescent molecule, and hence, molecular size. Large molecules exhibit a greater degree of polarization than small molecules. Thus, FP assays may be used to measure the interaction of a small fluorescent ligand or probe, with a larger protein, such as a TNF superfamily member. The degree of polarization provides a direct measure of the bound/free ratio of the fluorescent ligand.

The invention therefore provides a method for identifying a compound that is capable of binding to a trimeric protein that is a TNF superfamily member, whereby the compound-trimer complex binds to the requisite TNF superfamily receptor and modulates the signalling of the receptor comprising the steps of measuring the competition of the compound with a probe compound for binding to the trimeric form of a TNF superfamily member, comparing the level of competition observed to corresponding values from a control sample and selecting a compound that is capable of binding to a trimeric protein that is a TNF superfamily member, whereby the compound-trimer complex binds to the requisite TNF superfamily receptor and modulates the signalling of the receptor, wherein said method comprises performing a fluorescence polarization assay using the compound and a probe compound, comparing the degree of polarization of the probe compound in the presence of the compound with the degree of polarization in a control sample.

The ability of a test compound to compete with a probe or ligand may be quantified using standard terminology, such as half maximal inhibitory concentration ($IC_{50}$). In this context, $IC_{50}$ values represent the concentration of a compound that is required to result in a 50% inhibition of binding of the probe to the trimeric TNF superfamily member. The test compounds may have $IC_{50}$ values of 500 nM, 400 nM, 300 nM, 200 nM, 100 nM, 90 nM, 80 nM, 70 nM, 60 nM, 50 nM, 40 nM, 30 nM, 20 nM, 10 nM, 5 nM, 1 nM, 100 pM or less. Preferably, the test compounds have an $IC_{50}$ value of 200 nM or less. More preferably, the test compounds have an $IC_{50}$ value of 150 nM or less or an $IC_{50}$ value of 100 nM or less.

As mentioned above, in the present invention a library of compounds is typically subjected to one or more of the assays described herein in order to identify modulators of TNF superfamily members. Such libraries, which may comprise at least 260 compounds, at least 300, at least 500 or even at least 1000 compounds, may be screened using fluorescence polarization.

When a library of compounds is screened using fluorescence polarization, the method may comprise selecting a compound as a modulator of the TNF superfamily member if the compound results in a particular $IC_{50}$ value. For example, a compound may be identified as a modulator of the TNF superfamily member if the compound results in an $IC_{50}$ value of less than 50 μM. In some aspects, compounds are identified where they result in an $IC_{50}$ value of less than 500 nM, less than 200 nM or even less than 100 nM.

A compound from a library may also be identified as a modulator of a TNF superfamily member if it has the lowest $IC_{50}$ value out of all the compounds of the library that are tested. Likewise, a compound may be identified as a modulator of a TNF superfamily member where it has a low $IC_{50}$ value (i.e. a better $IC_{50}$ value) compared with other compounds of the library. For example, the 50% of compounds of the library which result in the lowest $IC_{50}$ values may be identified as modulators. In some aspects, the 25% or even 10% of compounds of the library which result in the lowest $IC_{50}$ values may be identified as modulators.

In one embodiment, the probe compound comprises a compound in accordance with the invention conjugated to a fluorescent ligand. Suitably, the fluorescent ligand is a fluorescent dye having a fluorescence lifetime of 10 ns or less. Typical examples of suitable fluorescent dyes include fluorescein, rhodamine, a Cy dye (for example Cy2, Cy3, Cy3B, Cy3.5, Cy5, Cy5.5 or Cy7), an Alexa Fluor® dye (for example Alexa Fluor® 350, 405, 430, 488, 532, 546, 555, 568, 594, 610, 633, 635, 647, 660, 680, 700, 750 or 790) or a BODIPY® dye (for example BODIPY FL, BODIPY R6G, BODIPY TMR or BODIPY TR). A specific example of a probe compound of the invention is the compound of formula (4) as depicted in FIG. 2.

The control sample may be identical to the sample being assayed, except that it lacks the test compound and/or it contains a known compound.

The sample comprising the TNF superfamily member and the compound may further comprise a destabilising agent. Destabilising agents, also known as chaotropes, include low molar concentrations (e.g. 1M) of urea, guanidine or acetonitrile, high concentrations (e.g. 6M or higher) of these reagents will result in complete dissociation of the TNFα trimer and unfolding of the constituent TNFα monomeric subunits. The destabilising agent is preferably DMSO, typically at a concentration of 5%, 10% or higher.

Although fluorescence polarization may be used to identify modulators of TNF superfamily members, in some aspects of the invention such modulators may be identified by any assay described herein excluding fluorescence polarization (i.e. by a method that is not fluorescence polarization). In particular, binding of a compound to a trimeric TNF superfamily member, and competition of a compound with a probe compound for binding to the trimeric form of the TNF superfamily member, may be determined by any method other than by fluorescence polarization.

Signalling Through TNF Superfamily Receptors

The invention may involve a method for identifying a compound that can modulate (i.e. prevent, reduce or enhance) signalling by TNF superfamily member-bound TNF superfamily receptors.

In one embodiment, the invention may involve a method for identifying a compound that can prevent or reduce signalling by TNF superfamily member-bound TNF superfamily receptors. Such a method may comprise contacting TNF superfamily receptors with both a TNF superfamily member and a compound-trimer complex and detecting whether the test compound prevents or reduces the TNF superfamily member trimer signalling through the TNF superfamily receptor. The amount of signalling from TNF superfamily receptors treated with the compound-trimer complex can be compared to the amount of signalling from TNF superfamily receptors treated with TNF superfamily member only.

Alternatively, the invention may involve a method for identifying a compound that can enhance signalling by TNF superfamily member-bound TNF superfamily receptors. Such a method may comprise contacting TNF superfamily receptors with both a TNF superfamily member and a compound-trimer complex and detecting whether the test compound increases the TNF superfamily member trimer signalling through the TNF superfamily receptor. The amount of signalling from TNF superfamily receptors treated with the compound-trimer complex can be compared to the amount of signalling from TNF superfamily receptors treated with TNF superfamily member only.

To detect the level of signalling, assays that measure the downstream effects of TNF superfamily receptor signalling can be performed. For example, a L929 murine fibrosarcoma cell-killing assay can be used to assess the stimulation of cell death by TNF. Inhibition of TNF-induced IL-8 production by human monocytes may also be used to assess whether a test compound inhibits TNF signalling via its receptor.

Antibodies for Identifying Trimer-Compound Complexes

The present inventors developed antibodies that bind selectively to complexes comprising compounds of the invention and a trimeric TNF superfamily member. These antibodies may be used to identify further compounds that are capable of inhibiting TNF.

In particular, the present inventors have identified two antibodies, termed CA185_01974 and CA185_01979, which were raised against human TNFα in complex with a compound of the invention. The heavy chain variable region (HCVR) of CA185_01974 is shown in SEQ ID NO: 1 and the light chain variable region (LCVR) of CA185_01974 is shown in SEQ ID NO: 2. The full length IgG1 heavy chain is shown in SEQ ID NO: 3 (1974 HC mIgG1 full) and the full length light chain (1974 LC kappa full) is shown in SEQ ID NO: 4.

The HCVR of CA185_01979 is shown in SEQ ID NO: 5 and the LCVR of CA185_01979 is shown in SEQ ID NO: 6. The full length IgG1 heavy chain of CA185_01979 is shown in SEQ ID NO: 7 (1979 HC mIgG1 full) and the full length light chain in SEQ ID NO: 8 (1979 L C Kappa full).

Antibodies comprising the above HCVR/LCVR or full-length sequence pairs can readily be generated by the skilled person using standard techniques.

Methods of the invention for determining compounds which are capable of binding to a trimeric protein which is a TNF superfamily member and modulating signalling through the receptor may therefore involve identifying whether an antibody with a HCVR/LCVR pair of SEQ ID NOs: 1/2 or 5/6 binds the trimer-compound complex. Likewise, methods may involve identifying whether an antibody with a sequence pair of SEQ ID Nos: 3/4 or 7/8 binds the trimer compound complex. Antibody assays may be used in addition to the other assays described herein.

Antibodies of the invention can be tested for binding to a compound-trimer complex by, for example, standard ELISA or Western blotting. The binding selectivity of an antibody may also be determined by monitoring binding of the antibody to cells expressing the target protein, for example by flow cytometry. Thus, a screening method of the invention may comprise the step of identifying an antibody that is capable of binding a compound-trimer complex by carrying out an ELISA or Western blot or by flow cytometry.

The antibodies described herein selectively (or specifically) recognise at least one compound-trimer complex, i.e. epitopes within a compound-trimer complex. An antibody, or other compound, "selectively binds" or "selectively recognises" a protein when it binds with preferential or high affinity to the protein for which it is selective but does not substantially bind, or binds with low affinity, to other proteins.

In the present instance, a compound-trimer complex may typically bind an antibody with a HCVR/LCVR pair of SEQ ID NOs: 1/2 or 5/6 (or with sequence pairs of SEQ ID NOs: 3/4 or 7/8) with an affinity of less than 1 nM. In other words, the methods of the invention may involve determining that a compound is capable of binding to a trimeric protein which is a TNF superfamily member and modulating signalling through the receptor by identifying that an antibody with a HCVR/LCVR pair of SEQ ID NOs: 1/2 or 5/6 (or sequence pairs of SEQ ID NOs: 3/4 or 7/8) binds the trimer-compound complex with a $K_{D-ab}$ of less than 1 nM. In some instances, the $K_{D-ab}$ may be less than 500 pM, or less than 200 pM. The affinity may be determined by surface plasmon resonance. The TNF is typically human TNFα.

Likewise, a complex of the invention may be a complex of a trimeric TNF superfamily member and a compound, wherein the compound-trimer complex binds an antibody with a HCVR/LCVR pair of SEQ ID NOs: 1/2 or 5/6 (or sequence pairs of SEQ ID Nos: 3/4 or 7/8). Again, the TNF is typically human TNF α, and the binding affinity is typically less than 1 nM (or less than 500 pM/200 pM). Binding affinity is typically determined by surface plasmon resonance.

Modulators of TNF Superfamily Members

Using the assays described herein, the present inventors have identified test compounds that bind to trimeric forms of the TNF superfamily members. These compounds are small molecular entities (SMEs) that have a molecular weight of 1000 Da or less, preferably 750 Da or less, more preferably 600 Da or less. These compounds stabilise a conformation of the trimeric TNF superfamily member that binds to the requisite TNF superfamily receptor and modulate the signalling of the receptor.

The stabilising effect of compounds of the invention on trimeric forms of TNF superfamily members may be quantified by measuring the thermal transition midpoint (Tm) of the trimers in the presence and absence of the compound. Tm signifies the temperature at which 50% of the biomolecules are unfolded. Compounds which stabilise TNF superfamily member trimers will increase the Tm of the trimers. Tm may be determined using any appropriate technique known in the art, for example using differential scanning calorimetry (DSC) or fluorescence probed thermal denaturation assays.

The compounds may bind inside the central space present within the TNF superfamily member trimer (i.e. the core of the trimer).

These compounds may turn the TNF superfamily member into a TNF superfamily receptor antagonist. These compounds are therefore capable of blocking the TNF superfamily member signalling without having to compete with the high affinity interaction between the TNF superfamily member and its receptor.

Alternatively, the compounds may stabilise a conformation of the trimeric TNF superfamily member that binds to the requisite TNF superfamily receptor and enhances the signalling of the receptor. These compounds are therefore capable of increasing the TNF superfamily member signalling without having to compete with the high affinity interaction between the TNF superfamily member and its receptor.

Where herein the compounds are described as antagonists, it will be understood that the compounds may equally be agonists and increase signalling by a TNF superfamily receptor that is bound to a complex of a TNF superfamily member trimer and such an agonist compound. Similarly, where other disclosure refers to antagonistic compounds, methods of identifying such compounds and uses of such compounds, this disclosure may refer equally to agonist compounds.

The compounds identified by the methods of the invention are allosteric modulators that bind to the natural agonists of the TNF superfamily receptors, i.e. to trimeric forms of TNF superfamily members and drive these trimers to adopt a conformation that still binds to the requisite TNF superfamily receptor and modulates signalling by the receptor. By modulating, it will be understood that the compound may have an antagonistic effect and so decrease signalling by a TNF superfamily receptor, or else a stimulatory effect and so increase or enhance signalling by a TNF superfamily receptor.

The compounds identified by the methods of the invention can convert the natural TNF superfamily member agonists into antagonists. In contrast, conventional TNF superfamily member antagonists bind to the TNF superfamily member or the TNF superfamily receptor and prevent the binding of the TNF superfamily member to the requisite receptor. In the alternative, the compounds identified by the methods of the invention may increase signalling by a TNF superfamily receptor when the TNF superfamily member is bound compared to the level of signalling by the TNF superfamily receptor when the TNF superfamily member is bound in the absence of the compound. The compounds identified by the methods of the invention may therefore convert the natural TNF superfamily member agonists into so-called "super-agonists". The compounds identified by the methods of the invention may therefore also be known as allosteric modulators of ligand activity (AMLAs).

The compounds identified by the methods of the invention are not limited in terms of their chemical formula or structure, provided that they bind to at least one TNF superfamily member and stabilise a conformation of the trimeric TNF superfamily member that binds to the requisite TNF superfamily receptor and modulate the signalling of the TNF superfamily receptor. The compounds identified by the methods of the invention can therefore be identified using the assays and methods described herein. The compounds identified by the methods of the invention may comprise a benzimidazole moiety or an isostere thereof, for example the compounds of formulae (1), (2) and (3).

The compounds identified by the methods of the invention may increase the binding affinity of TNF superfamily members (in the form of a compound-trimer complex) to the requisite receptor compared to the binding affinity of the TNF superfamily members to the requisite receptor in the absence of the compounds.

The compounds identified by the methods of the invention bind to the trimeric forms of TNF superfamily members. Such compounds may bind specifically to the trimeric forms of one or more TNF superfamily members. A compound identified by the methods of the invention may bind specifically to only one of the TNF superfamily members, but not to any other TNF superfamily members. A compound identified by the methods of the invention may also bind specifically to two, three, four or up to all of the TNF superfamily members. By specific, it will be understood that the compounds bind to the molecule or molecules of interest, in this case the trimeric form of the TNF superfamily member, with no significant cross-reactivity to any other molecule, which may include other members of the TNF superfamily. Cross-reactivity may be assessed by any suitable method, for example surface plasmon resonance. Cross-reactivity of a compound for the trimeric form of a TNF superfamily member with a molecule other than the trimeric form of that particular TNF superfamily member may be considered significant if the compound binds to the other molecule at least 5%, 10%, 15%, 20%, 25%, 30%, 35%, 40%, 45%, 50%, 55%, 60%, 65%, 70%, 75%, 80%, 85%, 90% or 100% as strongly as it binds to the trimeric form of the TNF superfamily member of interest. A compound that is specific for the trimeric form of a TNF superfamily member may bind to another molecule at less than 90%, 85%, 80%, 75%, 70%, 65%, 60%, 55%, 50%, 45%, 40%, 35%, 30%, 25% or 20% the strength that it binds to the trimeric form of the TNF superfamily member. Preferably, the compound binds to the other molecule at less than 20%, less than 15%, less than 10% or less than 5%, less than 2% or less than 1% the strength that it binds to the trimeric form of the TNF superfamily member.

The $K_{D-r}$ value of the TNF superfamily member for binding to its receptor in the presence of the test compound (i.e. in the form of a compound-trimer complex) may be at least 1.5 times, 2 times, 3 times, 4 times, 5 times, 10 times, 20 times, 30 times, 40 times, 50 times, 60 times, 70 times, 80 times, 90 times, 100 times lower than the $K_{D-r}$ value of the TNF superfamily member for binding to its receptor in the absence of the test compound. In a preferred embodiment, the $K_{D-r}$ value of the compound-trimer complex for binding to the TNF superfamily member is decreased at least 1.5 times, preferably at least 3 times, more preferably at least 4 times the $K_{D-r}$ value of the TNF superfamily trimer binding to the TNF superfamily receptor in the absence of the test compound, i.e. the binding affinity of the compound-trimer complex for the TNF superfamily receptor is preferably increased at least 1.5-fold, preferably at least three-fold, more preferably at least four-fold compared to the binding affinity of the TNF superfamily trimer to the TNF superfamily receptor in the absence of test compound.

The decrease in the $K_{D-r}$ value of the compound-trimer complex for binding to the TNF superfamily receptor compared to the $K_{D-r}$ value of the TNF superfamily trimer alone binding to the TNF superfamily receptor may result from an increase in the on rate ($k_{on-r}$) of the compound-trimer complex binding to the TNF superfamily receptor compared to the TNF superfamily trimer alone, and/or a decrease in the off rate ($k_{off-r}$) compared to the TNF superfamily trimer alone. In a preferred embodiment, the on rate ($k_{on-r}$) of the compound-trimer complex binding to the TNF superfamily receptor is increased compared to the TNF superfamily trimer alone. In another embodiment, the off rate ($k_{off-r}$) of the compound-trimer complex binding to the TNF superfamily receptor is decreased compared to the TNF superfamily trimer alone. In a further embodiment, the on rate ($k_{on-r}$) of the compound-trimer complex binding to the TNF superfamily receptor is increased, and the off-rate ($k_{off-r}$) of the compound-trimer complex binding to the TNF superfamily receptor is decreased, compared to the TNF superfamily trimer alone. The $k_{on-r}$ value of the compound-trimer complex to the requisite TNF superfamily receptor may be increased by at least 1.5-fold or at least two-fold and preferably at least three fold compared to the $k_{on-r}$ value of the TNF superfamily trimer binding to its receptor in the absence of the compound and/or the $k_{off-r}$ value of the compound-trimer complex to the requisite TNF superfamily receptor may be decreased by at least 1.2-fold, at least 1.6-fold, at least two-fold, more preferably at least 2.4-fold compared to the $k_{off-r}$ value of the TNF superfamily trimer binding to its receptor in the absence of the compound.

In one embodiment, the on-rate for compound binding to TNF superfamily trimer ($k_{on-c}$) is faster than the on-rate for compound-trimer complex binding to TNF superfamily receptor ($k_{on-r}$). In another embodiment, the off-rate for compound-trimer complex binding to TNF superfamily receptor ($k_{off-r}$) is faster than the off-rate for compound binding to TNF superfamily trimer ($k_{off-c}$). In a further embodiment, the on-rate for compound binding to TNF superfamily trimer ($k_{on-c}$) is faster than the on-rate for compound-trimer complex binding to TNF superfamily receptor ($k_{on-r}$), and the off-rate for compound-trimer complex binding to TNF superfamily receptor ($k_{off-r}$) is faster than the off-rate for compound binding to TNF superfamily trimer ($k_{off-c}$). In a preferred embodiment, the $K_{D-c}$ value of the compound for binding to TNF superfamily trimer is lower than the $K_{D-r}$ value of the compound-trimer complex for binding to TNF superfamily receptor, i.e. the compound has a higher affinity for the trimer than the compound-trimer complex has for the receptor.

The $k_{on-r}$, $k_{off-r}$, and $K_{D-r}$ values for both the compound-trimer complex and the TNF superfamily trimer to the requisite TNF superfamily receptor may be determined using any appropriate technique, for example surface plasmon resonance, mass spectrometry and isothermal calorimetry, as described in the Examples herein. The $K_{D-r}$ value of the TNF superfamily member for binding to its receptor in the presence of the test compound may be 1 µM, 100 nM, 10 nM, 5 nM, 1 nM, 100 pM, 10 pM or less. In a preferred embodiment the $K_{D-r}$ value of the TNF superfamily member for binding to its receptor in the presence of the test compound (i.e. in a compound-trimer complex) is 1 nM or less. In a more preferred embodiment, the $K_{D-r}$ value of a compound-trimer complex for binding to the requisite TNF superfamily receptor is less than 600 pM, more preferably less than 500 pM, less than 400 pM, less than 300 pM, less than 200 pM, less than 100 pM or less than 50 pM. In a most preferred embodiment the $K_{D-r}$ value of a compound-trimer complex for binding to the requisite TNF superfamily receptor is less than 200 pM.

Compounds identified by the methods of the invention may be identified by an assay which comprises determining the $K_{D-r}$ of the trimeric form of the TNF superfamily member in a sample of the TNF superfamily member and the compound; comparing the $K_{D-r}$ of the trimeric form of the TNF superfamily member in the sample with a control sample; and selecting a compound of the invention.

The compounds identified by the methods of the invention may completely or partially inhibit signalling through a TNF receptor when a TNF superfamily member in the form of a compound-trimer complex binds to the receptor. The compound may act to reduce signalling through a TNF superfamily receptor by at least 10%, 20%, 30%, 40%, 50%, 60%, 70%, 80%, 90% or 100%. Alternatively, the compounds identified by the methods of the invention may increase signalling through a TNF receptor when a TNF superfamily member in the form of a compound-trimer complex binds to the receptor. The compound may act to increase signalling through a TNF superfamily receptor by at least 10%, 20%, 30%, 40%, 50%, 60%, 70%, 80%, 90%, 100% or 200%. Any change in the level of signalling may be measured by any appropriate technique, including measuring reporter gene activity by alkaline phosphatase or luciferase, NF-κB translocation using machines such as the Cellomics Arrayscan, phosphorylation of downstream effectors, recruitment of signalling molecules, or cell death.

The compounds identified by the methods of the invention may modulate at least one of the downstream effects of signalling through a TNF receptor when a TNF superfamily member in the form of a compound-trimer complex binds to the receptor. Such effects are discussed herein and include TNF superfamily-induced IL-8, IL17A/F, IL2 and VCAM production, TNF superfamily-induced NF-κB activation and neutrophil recruitment. Standard techniques are known in the art for measuring the downstream effects of TNF superfamily members. The compounds identified by the methods of the invention may modulate at least 1, 2, 3, 4, 5, 10 or up to all of the downstream effects of signalling through a TNF receptor.

The activity of the compounds identified by the methods of the invention may be quantified using standard terminology, such as $IC_{50}$ or half maximal effective concentration ($EC_{50}$) values. $IC_{50}$ values represent the concentration of a compound that is required for 50% inhibition of a specified biological or biochemical function. $EC_{50}$ values represent the concentration of a compound that is required for 50% of its maximal effect. The compounds identified by the methods of the invention may have $IC_{50}$ or $EC_{50}$ values of 500 nM, 400 nM, 300 nM, 200 nM, 100 nM, 90 nM, 80 nM, 70 nM, 60 nM, 50 nM, 40 nM, 30 nM, 20 nM, 10 nM, 5 nM, 1 nM, 100 pM or less. $IC_{50}$ and $EC_{50}$ values may be measured using any appropriate technique, for example cytokine production can be quantified using ELISA. $IC_{50}$ and $EC_{50}$ values can then be generated using a standard 4-parameter logistic model also known as the sigmoidal dose response model.

TNF Superfamily and their Receptors

There are 22 TNF superfamily members currently known: TNFα (TNFSF1A), TNFβ (TNFSF1B), CD40L (TNFSF5), BAFF (TNFSF13B/BlyS), APRIL (TNFSF13), OX40L (TNFSF4), RANKL (TNFSF11/TRANCE), TWEAK (TNFSF12), TRAIL (TNFSF10), TL1A (TNFSF15), LIGHT (TNFSF14), Lymphotoxin, Lymphotoxin β (TNFSF3), 4-1BBL (TNFSF9), CD27L (TNFSF7), CD30L (TNFSF8), EDA (Ectodysplasin), EDA-A1 (Ectodysplasin A1), EDA-A2 (Ectodysplasin A2), FASL (TNFSF6), NGF and GITRL (TNFSF18).

In a preferred embodiment the TNF superfamily member is TNFα. TNFα exists in both a soluble (TNFα$_s$) and membrane-bound form (TNFα$_m$). When TNFα is referred to herein this encompasses both the TNFα$_s$ and TNFα$_m$ forms. In a particularly preferred embodiment, TNFα is in the TNFα$_s$ form.

The assays of the invention may be used to identify modulators of at least one of any TNF superfamily members, including the 22 known TNF superfamily members. Specifically, the assays of the invention may be used to identify compounds that bind to any TNF superfamily member, particularly to trimeric forms of TNF superfamily members, and that stabilise these trimers in a conformation that is capable of binding to the requisite TNF receptor, and which modulate signalling through said receptor. In a preferred embodiment, the assay of the invention is used to identify modulators of TNFα or CD40L, more preferably TNFα, even more preferably TNFα$_s$.

The compound identified by the methods of the invention may be a modulator of at least one of any TNF superfamily members, including the 22 known TNF superfamily members. In a preferred embodiment, the TNF superfamily member is TNFα or CD40L, more preferably TNFα even more preferably TNFα$_s$.

The compound-trimer complex of the invention may include the trimeric form of any TNF superfamily member, including the 22 known TNF superfamily members. In a preferred embodiment, the TNF superfamily member is TNFα or CD40L. More preferably the TNF superfamily member is TNFα, even more preferably TNFα$_s$.

Members of the TNF superfamily bind to, and initiate signalling through TNF receptors. There are currently 34 known TNF receptors: 4-1BB (TNFRSF9/CD137), NGF R (TNFRSF16), BAFF R (TNFRSF13C), Osteoprotegerin (TNFRSF11B), BCMA (TNFRSF17), OX40 (TNFRSF4), CD27 (TNFRSF7), RANK (TNFRSF11A), CD30 (TN- FRSF8), RELT (TNFRSF19L), CD40 (TNFRSF5), TACI (TNFRSF13B), DcR3 (TNFRSF6B), TNFRH3 (TNFRSF26), DcTRAIL R1 (TNFRSF23), DcTRAIL R2 (TNFRSF22), TNF-R1 (TNFRSF1A), TNF-R2 (TNFRSF1B), DR3 (TNFRSF25), TRAIL R1 (TNFRSF10A), DR6 (TNFRSF21), TRAIL R2 (TNFRSF10B), EDAR, TRAIL R3 (TNFRSF10C), Fas (TNFRSF6/CD95), TRAIL R4 (TNFRSF10D), GITR (TNFRSF18), TROY (TNFRSF19), HVEM (TNFRSF14), TWEAK R (TNFRSF12A), TRAMP (TNFRSF25), Lymphotoxin β R (TNFRSF3) and XEDAR.

In a preferred embodiment the TNF receptor is TNF-R1 or TNF-R2. When TNF-R is referred to herein this encompasses both TNF-R1 and TNF-R2, including the extracellular domain (ECD) of TNF-R1 and TNF-R2. The assays of the invention may be used to identify compounds that modulate the signalling of TNF superfamily members through any requisite TNF superfamily receptor. In a preferred embodiment, the assays of the invention may be used to identify compounds that modulate the signalling of TNF superfamily members through TNF-R1, TNF-R2 or CD40. In a more preferred embodiment, the TNF superfamily member is TNFα and the TNF receptor is TNF-R1 or TNF-R2. In an even more preferred embodiment, the TNF superfamily member is TNFα and the TNF receptor is TNF-R1. In an even more preferred embodiment, the TNF superfamily member is TNFα$_s$ and the TNF receptor is TNF-R1. The assays of the invention may be used to identify compounds which act by specifically modulate the signalling of TNF superfamily members through TNF-R1. In particular, the compounds may act by modulating the signalling of TNF superfamily members through TNF-R1, but have no effect on signalling of TNF superfamily members through TNF-R2. In an even more preferred embodiment, the TNF superfamily member is TNFα$_s$ and the TNF receptor is TNF-R1.

The compound-trimer complex of the invention may modulate TNF superfamily members signalling through at least one TNF receptor, including the 34 known TNF receptors. In a preferred embodiment, the TNF receptor is TNF-R1, TNF-R2 or CD40L.

In a more preferred embodiment, the TNF superfamily member is TNFα and the TNF receptor is TNF-R1 or TNF-R2. In an even more preferred embodiment, the TNF superfamily member is TNFα and the TNF receptor is TNF-R1. In an even more preferred embodiment, the TNF superfamily member is TNFα$_s$ and the TNF receptor is TNF-R1.

Therapeutic Indications

TNFα is the archetypal member of the TNF superfamily. TNFα is a pleiotropic cytokine that mediates immune regulation and inflammatory responses. In vivo, TNFα is also known to be involved in responses to bacterial, parasitic and viral infections. In particular, TNFα is known to have a role in rheumatoid arthritis (RA), inflammatory bowel diseases (including Crohn's disease), psoriasis, Alzheimer's disease (AD), Parkinson's disease (PD), pain, epilepsy, osteoporosis, asthma, sepsis, fever, Systemic lupus erythematosus (SLE) and Multiple Sclerosis (MS) and cancer. TNFα is also known to have a role in Amyotrophic Lateral Sclerosis (ALS), ischemic stroke, immune complex-mediated glomerulonephritis, lupus nephritis (LN), antineutrophil cytoplasmic antibodies (ANCA-) associated glomerulonephritis, minimal change disease, diabetic nephropathy (DN), acute kidney injury (AKI), obstructive uropathy, kidney allograft rejection, cisplatin-induced AKI and obstructive uropathy.

Other members of the TNF superfamily are known to be involved in autoimmune disease and immune deficiencies.

In particular, members of the TNF superfamily are known to be involved in RA, SLE, cancer, MS, asthma, rhinitis, osteoporosis and multiple myeloma (MM). TL1A is known to play a role in organ transplant rejection.

A compound identified by the methods of the invention or a complex of the invention may be used to treat, prevent or ameliorate any condition that that can be treated, prevented or ameliorated by a conventional TNF superfamily member modulator. The compound identified by the methods of the invention or the complex of the invention may be used alone or in combination with a conventional TNF superfamily member modulator. Any condition that results, partially or wholly, from pathogenic signalling through a TNF receptor by a TNF superfamily member or from a deficiency in signalling through a TNF receptor by a TNF superfamily member may in principle be treated, prevented or ameliorated according to the present invention. Pathogenic signalling through a TNF receptor by a TNF superfamily member includes increased signalling through a TNF receptor over and above the normal physiological level of signalling, signalling through a TNF receptor which is initiated normally, but which fails to stop in response to normal physiological signals and signalling through a TNF receptor that is within the normal physiological range of magnitude, but which is initiated by non-physiological means. In a preferred embodiment, the invention relates to the treatment, prevention or amelioration of conditions mediated or influenced by TNFα or CD40L.

The compounds identified by the methods of the present invention that interact with TNFα are accordingly beneficial in the treatment and/or prevention of various human ailments. These include autoimmune and inflammatory disorders; neurological and neurodegenerative disorders; pain and nociceptive disorders; and cardiovascular disorders.

Inflammatory and autoimmune disorders include systemic autoimmune disorders, autoimmune endocrine disorders and organ-specific autoimmune disorders. Systemic autoimmune disorders include systemic lupus erythematosus (SLE), psoriasis, vasculitis, polymyositis, scleroderma, multiple sclerosis, ankylosing spondylitis, rheumatoid arthritis and Sjögren's syndrome. Autoimmune endocrine disorders include thyroiditis. Organ-specific autoimmune disorders include Addison's disease, haemolytic or pernicious anaemia, glomerulonephritis (including Goodpasture's syndrome), Graves' disease, idiopathic thrombocytopenic purpura, insulin-dependent diabetes mellitus, juvenile diabetes, uveitis, inflammatory bowel disease (including Crohn's disease and ulcerative colitis), pemphigus, atopic dermatitis, autoimmune hepatitis, primary biliary cirrhosis, autoimmune pneumonitis, autoimmune carditis, myasthenia gravis, spontaneous infertility, osteoporosis, asthma and muscular dystrophy (including Duchenne muscular dystrophy).

Neurological and neurodegenerative disorders include Alzheimer's disease, Parkinson's disease, Huntington's disease, stroke, amyotrophic lateral sclerosis, spinal cord injury, head trauma, seizures and epilepsy.

Cardiovascular disorders include thrombosis, cardiac hypertrophy, hypertension, irregular contractility of the heart (e.g. during heart failure), and sexual disorders (including erectile dysfunction and female sexual dysfunction).

In particular, a compound identified by the methods of the invention or a complex of the invention may be used to treat or prevent inflammatory disorders, CNS disorders, immune disorders and autoimmune diseases, pain, osteoporosis, fever and organ transplant rejection. In a preferred embodiment, a compound identified by the methods of the invention or a complex of the invention may be used to treat or prevent rheumatoid arthritis, inflammatory bowel diseases (including Crohn's disease), psoriasis, Alzheimer's disease, Parkinson's disease, epilepsy, asthma, sepsis, systemic lupus erythematosus, multiple sclerosis, asthma, rhinitis, cancer and osteoporosis. In another preferred embodiment, a compound identified by the methods of the invention or a complex of the invention may be used to treat or prevent rheumatoid arthritis (RA), non specific inflammatory arthritis, erosive bone disease, chondritis, cartilage degeneration and/or destruction, juvenile inflammatory arthritis, Still's Disease (juvenile and/or adult onset), juvenile idiopathic arthritis, juvenile idiopathic arthritis (both oligoarticular and polyarticular forms), inflammatory bowel diseases (including Crohn's disease, ulcerative colitis, indeterminate colitis, pouchitis), psoriasis, psoriatic arthopathy, ankylosing spondylitis, Sjogren's Disease, Alzheimer's disease (AD), Behcet's Disease, Parkinson's disease (PD), amyotrophic lateral sclerosis (ALS), ischemic stroke, pain, epilepsy, osteoporosis, osteopenia, anaemia of chronic disease, cachexia, diabetes, dyslipidemia, metabolic syndrome, asthma, chronic obstructive airways (or pulmonary) disease, sepsis, fever, respiratory distress syndrome, systemic lupus erythematosus (SLE), multiple sclerosis (MS) immune complex-mediated glomerulonephritis, lupus nephritis (LN), antineutrophil cytoplasmic antibodies (ANCA-) associated glomerulonephritis, minimal change disease, diabetic nephropathy (DN), acute kidney injury (AKI), obstructive uropathy, kidney allograft rejection, cisplatin-induced AKI and obstructive uropathy, eye diseases (including diabetic retinopathy, diabetic macular oedema, retinopathy of prematurity, age related macular degeneration, macular oedema, proliferative and/or non proliferative retinopathy, corneal vascularisation including neovascularization, retinal vein occlusion, various forms of uveitis and keratitis), thryoiditis, fibrosing disorders including various forms of hepatic fibrosis, various forms of pulmonary fibrosis, systemic sclerosis, scleroderma, cancer and cancer associated complications (including skeletal complications, cachexia and anaemia).

Pharmaceutical Compositions, Dosages and Dosage Regimes

Compounds identified by the methods of the invention and a compound-trimer complexes of the invention will typically be formulated into pharmaceutical compositions, together with a pharmaceutically acceptable carrier.

As used herein, "pharmaceutically acceptable carrier" includes any and all solvents, dispersion media, coatings, antibacterial and antifungal agents, isotonic and absorption delaying agents, and the like that are physiologically compatible. The carrier may be suitable for parenteral, e.g. intravenous, intramuscular, intradermal, intraocular, intraperitoneal, subcutaneous, spinal or other parenteral routes of administration, for example by injection or infusion. Alternatively, the carrier may be suitable for non-parenteral administration, such as a topical, epidermal or mucosal route of administration. In a preferred embodiment the carrier is suitable for oral administration. Depending on the route of administration, the modulator may be coated in a material to protect the compound from the action of acids and other natural conditions that may inactivate the compound.

The pharmaceutical compositions of the invention may include one or more pharmaceutically acceptable salts. A "pharmaceutically acceptable salt" refers to a salt that retains the desired biological activity of the parent compound and does not impart any undesired toxicological effects. Examples of such salts include acid addition salts and base addition salts.

Preferred pharmaceutically acceptable carriers comprise aqueous carriers or diluents. Examples of suitable aqueous carriers that may be employed in the pharmaceutical compositions of the invention include water, buffered water and saline. Examples of other carriers include ethanol, polyols (such as glycerol, propylene glycol, polyethylene glycol, and the like), and suitable mixtures thereof, vegetable oils, such as olive oil, and injectable organic esters, such as ethyl oleate. In many cases, it will be preferable to include isotonic agents, for example, sugars, polyalcohols such as mannitol, sorbitol, or sodium chloride in the composition.

Therapeutic compositions typically must be sterile and stable under the conditions of manufacture and storage. The composition can be formulated as a solution, microemulsion, liposome, or other ordered structure suitable to high drug concentration.

Pharmaceutical compositions of the invention may comprise additional active ingredients.

Also within the scope of the present invention are kits comprising compounds identified by the methods of the invention and complexes of the invention and instructions for use. The kit may further contain one or more additional reagents, such as an additional therapeutic or prophylactic agent as discussed above.

The compounds identified by the methods of the invention and the compound-trimer complexes of the present invention or formulations or compositions thereof may be administered for prophylactic and/or therapeutic treatments.

In therapeutic applications, compounds and compound-trimer complexes are administered to a subject already suffering from a disorder or condition as described above, in an amount sufficient to cure, alleviate or partially arrest the condition or one or more of its symptoms. Such therapeutic treatment may result in a decrease in severity of disease symptoms, or an increase in frequency or duration of symptom-free periods. An amount adequate to accomplish this is defined as a "therapeutically effective amount".

In prophylactic applications, formulations are administered to a subject at risk of a disorder or condition as described above, in an amount sufficient to prevent or reduce the subsequent effects of the condition or one or more of its symptoms. An amount adequate to accomplish this is defined as a "prophylactically effective amount". Effective amounts for each purpose will depend on the severity of the disease or injury as well as the weight and general state of the subject.

A subject for administration may be a human or non-human animal. The term "non-human animal" includes all vertebrates, e.g., mammals and non-mammals, such as non-human primates, sheep, dogs, cats, horses, cows, chickens, amphibians, reptiles, etc. Administration to humans is preferred.

A compound identified by the methods of the invention or a compound-trimer complex of the present invention may be administered via one or more routes of administration using one or more of a variety of methods known in the art. As will be appreciated by the skilled artisan, the route and/or mode of administration will vary depending upon the desired results. Examples of routes of administration for compounds or compound-trimer complexes of the invention include intravenous, intramuscular, intradermal, intraocular, intraperitoneal, subcutaneous, spinal or other parenteral routes of administration, for example by injection or infusion. The phrase "parenteral administration" as used herein means modes of administration other than enteral and topical administration, usually by injection. Alternatively, a compound identified by the methods of the invention or a compound-trimer complex of the present invention of the invention can be administered via a non-parenteral route, such as a topical, epidermal or mucosal route of administration. In a preferred embodiment the compound identified by the methods of the invention or a compound-trimer complex of the invention is for oral administration.

A suitable dosage of a compound identified by the methods of the invention or a compound-trimer complex of the invention may be determined by a skilled medical practitioner. Actual dosage levels of the active ingredients in the pharmaceutical compositions of the present invention may be varied so as to obtain an amount of the active ingredient that is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A suitable dose may be, for example, in the range of from about 0.01 µg/kg to about 1000 mg/kg body weight, typically from about 0.1 µg/kg to about 100 mg/kg body weight, of the patient to be treated. For example, a suitable dosage may be from about 1 µg/kg to about 10 mg/kg body weight per day or from about 10 µg/kg to about 5 mg/kg body weight per day.

Dosage regimens may be adjusted to provide the optimum desired response (e.g., a therapeutic response). For example, a single dose may be administered, several divided doses may be administered over time or the dose may be proportionally reduced or increased as indicated by the exigencies of the therapeutic situation. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Administration may be in single or multiple doses. Multiple doses may be administered via the same or different routes and to the same or different locations. Alternatively, doses can be via a sustained release formulation, in which case less frequent administration is required. Dosage and frequency may vary depending on the half-life of the antagonist in the patient and the duration of treatment desired.

As mentioned above, compounds identified by the methods of the invention or compound-trimer complexes of the invention may be co-administered with one or other more other therapeutic agents. For example, the other agent may be an analgesic, anaesthetic, immunosuppressant or anti-inflammatory agent.

Combined administration of two or more agents may be achieved in a number of different ways. Both may be administered together in a single composition, or they may be administered in separate compositions as part of a combined therapy. For example, the one may be administered before, after or concurrently with the other.

The following Examples illustrate the invention.

EXAMPLES

Example 1—Synthesis of the Compounds of Formula (1), (2) and (3)

Intermediate 1:
1-(2,5-Dimethylbenzyl)-1H-benzimidazole

Cesium carbonate (22.0 g, 100.0 mmol) and n-butylammonium iodide (12.5 g, 34.0 mmol) were added to a solution of benzimidazole (4.0 g, 34.0 mmol) in DMF (60 ml) at 0° C. The reaction mixture was stirred for 10 minutes at 0° C. and then 2,5-dimethylbenzyl bromide (6.7 g, 34.0 mmol) was added. The reaction mixture was allowed to warm to room temperature and stirred for 3 h. The mixture was quenched with ice-cold water (50 ml) and extracted with ethyl acetate (3×40 ml). The organic layers were dried over anhydrous sodium sulphate and the solvent was removed in vacuo to afford the title compound (8.0 g, 75%) as an off-white solid. $\delta_H$ ($d_6$-DMSO) 8.23 (s, 1H), 7.68-7.66 (m, 1H), 7.43-7.41 (m, 1H), 7.21-7.19 (m, 2H), 7.10 (d, J 7.6 Hz, 1H), 7.01 (d, J 7.6 Hz, 1H), 6.67 (s, 1H), 5.45 (s, 2H), 2.25 (s, 3H), 2.14 (s, 3H). LCMS (ES$^+$) 237 (M+H)$^+$.

Intermediate 2: 5-Bromo-2-nitroaniline

2-Fluoro-4-bromo-1-nitrobenzene (0.5 g, 2.2 mmol) was added to methanolic ammonia (10 ml) and stirred at room temperature. for 18 h. The reaction mixture was then concentrated in vacuo and the residue was triturated with isohexane, yielding the title compound (0.48 g, 97%) as a yellow solid. $\delta_H$ ($d_6$-DMSO) 7.88 (d, J 8.8 Hz, 1H), 7.53 (br s, 2H), 7.25 (d, J 3.0 Hz, 1H), 6.75 (dd, J 9.2, 2.0 Hz, 1H).

Intermediate 3:
5-Bromo-N-(2,5-dimethylbenzyl)-2-nitroaniline

Sodium hydride (60% dispersion in oil, 0.82 g, 20.7 mmol) was added to a stirred solution of Intermediate 2 (5.0 g, 23.0 mmol) in DMF (50 ml) at 0° C. 2,5-Dimethylbenzyl bromide (4.56 g, 23.0 mmol) was added and the reaction mixture was warmed to room temperature and stirred for 5 h. The reaction mixture was quenched with saturated aqueous ammonium chloride solution, extracted with ethyl acetate (3×50 ml), washed with water (2×30 ml), dried over anhydrous sodium sulfate and concentrated in vacuo. The residue was purified by column chromatography (SiO$_2$, 5% EtOAc/isohexane), yielding the title compound (4.89 g, 63%) as a yellow solid. $\delta_H$ ($d_6$-DMSO) 8.42 (br s, 1H), 8.01 (d, J 8.8 Hz, 1H), 7.12-6.86 (m, 4H), 6.85 (d, J 7.2, 1.6 Hz, 1H), 4.54 (d, J 5.6 Hz, 2H), 2.28 (s, 3H), 2.21 (s, 3H).

Intermediate 4: 5-Bromo-N$^1$-(2,5-dimethylbenzyl) benzene-1,2-diamine

SnCl$_2$ (20.2 g, 89.4 mmol) was added to a stirred solution of Intermediate 3 (10.0 g, 29.8 mmol) in EtOH (200 ml) and the reaction mixture was heated to 80° C. for 5 h. The reaction mixture was then concentrated in vacuo and the residue neutralized with saturated aqueous sodium bicarbonate solution and extracted with DCM (3×100 ml). The combined organics were washed with water (2×50 ml), extracted, dried over anhydrous sodium sulfate and concentrated in vacuo. The residue was purified by column chromatography (SiO$_2$, 5% MeOH/DCM), yielding the title compound (5.4 g, 69%) as a dark brown oil. δ$_H$ (d$_6$-DMSO) 7.08 (s, 1H), 7.06 (d, J 7.6 Hz, 2H), 6.97 (d, J 7.6 Hz, 1H), 6.53 (dd, J 8.4, 2.0 Hz, 1H), 6.47 (d, J 8.0 Hz, 1H), 6.45 (d, J 2.0 Hz, 1H), 5.06 (t, J 5.4 Hz, 1H), 4.77 (br s, 2H), 4.15 (d, J 5.2 Hz, 1H), 2.27 (s, 3H), 2.22 (s, 3H). LCMS (ES$^+$) 305 (M+H)$^+$.

Intermediate 5:
6-Bromo-1-(2,5-dimethylbenzyl)-1H-benzimidazole

A mixture of Intermediate 4 (0.40 g, 1.31 mmol) and formic acid (10 ml) was stirred at room temperature. for 18 h. The reaction mixture was concentrated in vacuo and the residue partitioned between ethyl acetate and saturated aqueous sodium bicarbonate solution. The organic layer was dried over anhydrous sodium sulphate and concentrated in vacuo. The crude residue was purified by column chromatography (SiO$_2$, 20-75% EtOAc/isohexane), yielding the title compound (0.20 g, 48%) as a white solid. δ$_H$ (d$_6$-DMSO) 8.24 (s, 1H), 7.74 (d, J 1.7 Hz, 1H), 7.64 (d, J 8.6 Hz, 1H), 7.34 (dd, J 8.6, 1.9 Hz, 1H), 7.12 (d, J 7.7 Hz, 1H), 7.02 (d, J 7.8 Hz, 1H), 6.61 (s, 1H), 5.47 (s, 2H), 2.24 (s, 3H), 2.15 (s, 3H). LCMS (ES$^+$) 316 (M+H)$^+$.

Intermediate 6: [6-Bromo-1-(2,5-dimethylbenzyl)-1H-benzimidazol-2-yl](pyridin-4-yl)methanol To diisopropylamine (2.8 ml) in THF (10 ml), cooled to 0° C., was added n-BuLi (12.5 ml, 1.6M in hexanes) and the resulting mixture was stirred at 0° C. for 10 minutes. An aliquot of this freshly prepared LDA (1.8 ml, 1.62 mmol) was added to a solution of Intermediate 5 (0.25 g, 0.81 mmol) in THF (5 ml) at −78° C. The reaction mixture was stirred for 2 h at −78° C., then pyridine-4-carboxaldehyde (0.15 ml, 1.62 mmol) was added and the reaction mixture was stirred at −78° C. for 10 minutes. The mixture was quenched with saturated aqueous sodium chloride solution and allowed to warm to room temperature. The mixture was extracted with ethyl acetate (3×40 ml). The organic layers were dried over anhydrous sodium sulphate and concentrated in vacuo. The residue was purified by column chromatography (SiO$_2$, 0-10% MeOH/DCM), yielding the title compound (0.18 g, 51%) as a white solid. LCMS (ES$^+$) 423 (M+H)$^+$.

Intermediate 7:
5-(3-Fluoro-4-nitrophenyl)-2-methoxypyridine

6-Methoxypyridin-3-ylboronic acid (40.0 g, 262 mmol), 4-bromo-2-fluoro-1-nitrobenzene (52.3 g, 238 mmol) and Na$_2$CO$_3$ (76 g, 713 mmol) were mixed in 1,2-dimethoxyethane (1200 mL) and water (300 mL). The reaction mixture was purged with argon. Pd(PPh$_3$)$_2$Cl$_2$ (8.34 g, 11.89 mmol) was added and the mixture was heated to 90° C. for 1.5 h. EtOAc and water were added. The organic phase was separated and the aqueous phase was extracted twice with EtOAc. The combined organic layers were dried over Na$_2$SO$_4$, after which the solvent was removed in vacuo. The residue was recrystallised from toluene, affording the title compound (42.00 g, 169.2 mmol, 71%). MS [ESI+] m/z: 249 [M+H]$^+$.

Intermediate 8: N-[2-(Difluoromethoxy)benzyl]-5-(6-methoxypyridin-3-yl)-2-nitroaniline 2-(Difluoromethoxy)benzylamine (2.093 g, 12.09 mmol) was dissolved in NMP (20 mL). Intermediate 7 (2 g, 8.06 mmol) and K$_2$CO$_3$ (1.336 g, 9.67 mmol) were added. This mixture was heated under microwave irradiation at 150° C. for 30 minutes. EtOAc and water were added. The organic phase was separated and the aqueous phase was extracted twice with EtOAc. The combined organic layers were washed three times with water and twice with brine. After drying over Na$_2$SO$_4$, the solvent was removed in vacuo. The residue was recrystallised from heptane/EtOAc (100/25 mL), to afford the title compound (2.513 g, 6.26 mmol, 78%). MS [ESI+]m/z: 402 [M+H]$^+$.

Intermediate 9: N$^1$-[2-(Difluoromethoxy)benzyl]-5-(6-methoxypyridin-3-yl)benzene-1,2-diamine Palladium on carbon (1.10 g, 10 wt %) was added to a solution of Intermediate 8 (2.512 g, 6.26 mmol) in EtOAc (150 mL), flushed with argon. The atmosphere was replaced with a H$_2$ atmosphere and the reaction mixture was stirred under 1 bar of H$_2$ for 1 h. The mixture was filtered through a layer of Kieselguhr. The filtrate was concentrated in vacuo. Purification using flash column chromatography with 7-60% EtOAc in heptane afforded the title compound (2.07 g, 5.57 mmol, 89%). MS [ESI+] m/z: 372 [M+H]$^+$.

Intermediate 10: 5-{4-Amino-3-[2-(difluoromethoxy)benzylamino]phenyl}pyridin-2(1H)-one Pyridine hydrochloride (10.64 g, 92 mmol) was added to Intermediate 9 (6.84 g, 18.42 mmol). The reaction mixture was heated to 165° C. in an open vessel for 3 minutes. Water was added and the mixture was sonicated. The precipitate was filtered off and then triturated in boiling acetonitrile. Filtration of the precipitate afforded the title compound (3.822 g, 9.95 mmol, 54%). MS [ESI+] m/z: 358 [M+H]$^+$.

Compound (1): [1-(2,5-Dimethylbenzyl)-1H-benzimidazol-2-yl](pyridin-4-yl)methanol To a solution of Intermediate 1 (0.25 g, 1.06 mmol) in THF (10 ml) at −78° C. was added 1.6M n-butyllithium (0.79 ml, 1.27 mmol) slowly dropwise and the reaction mixture was stirred for 20 minutes. Isonicotinaldehyde (0.17 g, 1.59 mmol) in THF (1 ml) was added slowly dropwise. After a further 10 minutes the reaction mixture was quenched with water (1 ml) and allowed to warm to room temperature. The reaction mixture was poured into ethyl acetate/water. The organic layer was separated, dried (MgSO4) and concentrated in vacuo. The residue was purified by column chromatography (SiO$_2$, 0-30% MeOH/DCM), yielding the title compound (0.2 g, 55%) as an off-white solid. δ$_H$ (CDCl$_3$) 8.31 (d, J 5.9 Hz, 2H), 7.69 (d, J 8.0 Hz, 1H), 7.28-7.16 (m, 4H), 7.00-6.95 (m, 2H), 6.87-6.85 (m, 1H), 6.16 (s, 2H), 5.84 (s, 1H), 5.35-5.09 (dd, JAB 17.0 Hz, 2H), 2.25 (s, 3H), 1.89 (s, 3H). LCMS (ES$^+$) 344 (M+H)$^+$.

Compound (2): [1-(2,5-Dimethylbenzyl)-6-(1-methyl-1H-pyrazol-4-yl)-1H-benzimidazol-2-yl](pyridin-4-yl)methanol 1-Methyl-4-(4,4,5,5-tetramethyl-[1,3,2]dioxaborolan-2-yl)-1H-pyrazole (0.15 g, 0.71 mmol), and a 2M solution of sodium carbonate (2 ml) were added to a solution of Intermediate 6 (0.15 g, 0.36 mmol), in 1,4-dioxane:water (4:1, 5 ml) and the reaction was degassed for 10 minutes. PdCl$_2$(dppf) (0.01 g, 0.05 mmol) was added and the reaction mixture was degassed for 10 minutes, then heated to 100° C.

for 60 minutes in a Biotage microwave reactor. Ethyl acetate was added and the reaction mixture was filtered through a Celite pad. The organic layer was separated, dried over anhydrous sodium sulphate, and concentrated in vacuo. The residue was purified by preparative HPLC, yielding the title compound as a white solid. $\delta_H$ ($d_6$-DMSO) 8.39 (dd, J 4.5, 1.6 Hz, 2H), 8.03 (s, 1H), 7.76 (s, 1H), 7.64 (d, J 8.8 Hz, 1H), 7.44-7.41 (m, 2H), 7.28 (d, J 5.6 Hz, 2H), 7.06 (d, J 7.7 Hz, 1H), 6.87 (d, J 6.8 Hz, 1H), 6.70 (d, J 5.5 Hz, 1H), 6.01 (d, J 5.5 Hz, 1H), 5.83 (s, 1H), 5.63-5.43 (m, 2H), 3.82 (s, 3H), 2.33 (s, 3H), 1.92 (s, 3H). LCMS (ES$^+$) 424 (M+H)$^+$.

Compound (3): 5-(1-[2-(Difluoromethoxy)benzyl]-2-{[3-(2-oxo-pyrrolidin-1-yl)phenoxy]methyl}-1H-benzimidazol-6-yl)-pyridin-2(1H)-one 2-[3-(2-Oxopyrrolidin-1-yl)phenoxy]acetic acid (2 equivalents) was added to a solution of HATU (2 equivalents) in DMF (2 mL). The mixture was stirred for 30 minutes. A solution of Intermediate 9 (1 equivalent) in DMF (2 mL) was added and the mixture was stirred at room temperature for 24 h. The temperature was then raised to 50° C. and stirring was continued for 24 h. The solvent was evaporated and the residue dissolved in acetic acid (4 mL) and heated to 80° C. for 5 h. The acetic acid was removed by evaporation. The residue was partitioned between water/chloroform (1:1, 6 mL) at 50° C. The layers were separated by using a phase separator. The aqueous layer was washed with chloroform (4 mL) and the organic layer was evaporated to dryness. The residue was taken up in DMSO (1 mL) and purified by preparative LCMS to yield the title compound.

Example 2—Synthesis of the Conjugate of Formula (4)

Intermediate 10: 1-(2,5-Dimethylbenzyl)-6-[4-(piperazin-1-ylmethyl)-phenyl]-2-(pyridin-4-ylmethyl)-1H-benzimidazole Synthesized by a sequence of steps corresponding to the preparation of Intermediates 7, 8 and 9, followed by the preparation of Compound (3), utilising the appropriate boronic acid, the appropriate amine and the appropriate carboxylic acid.

Conjugate (4)

Intermediate 10 (27.02 mg, 0.0538 mmol) was dissolved in DMSO (2 mL). 5 (−6) Carboxy-fluorescein succinimyl ester (24.16 mg, 0.0510 mmol) (Invitrogen catalogue number: C1311) was dissolved in DMSO (1 mL) to give a bright yellow solution. The two solutions were mixed at room temperature, the mixture turning red in colour. The mixture was stirred at room temperature. Shortly after mixing a 20 µL aliquot was removed and diluted in a 80:20 mixture of AcOH:H$_2$O for LC-MS analysis on the 1200RR-6140 LC-MS system. The chromatogram showed two closely eluting peaks at retention times of 1.42 and 1.50 minutes, both with mass (M+H)$^+$=860.8 amu, corresponding to the two products formed with the 5- and 6-substituted carboxyfluorescein group. A further peak at retention time 2.21 minutes had a mass of (M+H)$^+$=502.8 amu, corresponding to Intermediate 10. No peak was observed for unreacted 5(−6) carboxyfluorescein succinimyl ester. The peak areas were 22.0%, 39.6% and 31.4% for the three signals, indicating a 61.6% conversion to the two isomers of the desired product at that time-point. Further 20 µL aliquots were extracted after several hours and then after overnight stirring, diluted as before and subjected to LC-MS analysis. The percentage conversion was determined as 79.8% and 88.6% respectively at these time-points. The mixture was purified on a UV-directed preparative HPLC system. The pooled purified fractions were freeze-dried to remove excess solvent. After freeze-drying, an orange solid (23.3 mg) was recovered, equivalent to 0.027 mmol of product, corresponding to an overall yield of 53% for the reaction and preparative HPLC purification.

Example 3—Screens for Compounds that Bind to TNFα

The compounds of formulae (1) and (2) have been screened using the following assay.

384 well uncoated plates (standard binding) Meso Scale Discovery plates (MSD) were coated overnight with the extracellular domain of TNFR (TNFR-ECD) (10 µl, 1 ug/mL in PBS). To ensure even distribution plates were centrifuged at 1000 rpm for 2 minutes. The plates were then sealed and stored at +4° C. overnight.

The wells of the plates were then washed three times in 50 µl phosphate buffered saline pH 6.5 (PB) with 0.05% Tween 20 (wash buffer), and then blocked with 50 µl 2% BSA. The plates were then incubated at room temperature on a shaker (600 rpm) for 2 hours. After this incubation plates were washed (3×50 µl wash buffer per well).

During the blocking incubation, compounds of formulae (1) and (2) were pre-incubated with TNF (R&D Systems) prior to addition to the pre-blocked and washed MSD plates. For a single point assay as shown in FIG. 3A the compounds were assayed at a final concentration of 100 µM (5% final v/v DMSO).

Figure 3B:
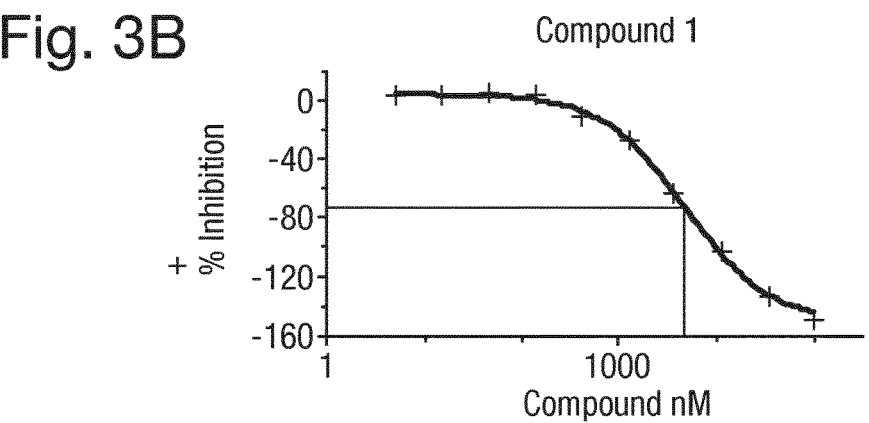
FIG. 3B shows a dose response curve for compound of formula (1) using this assay.
Figure 3C:
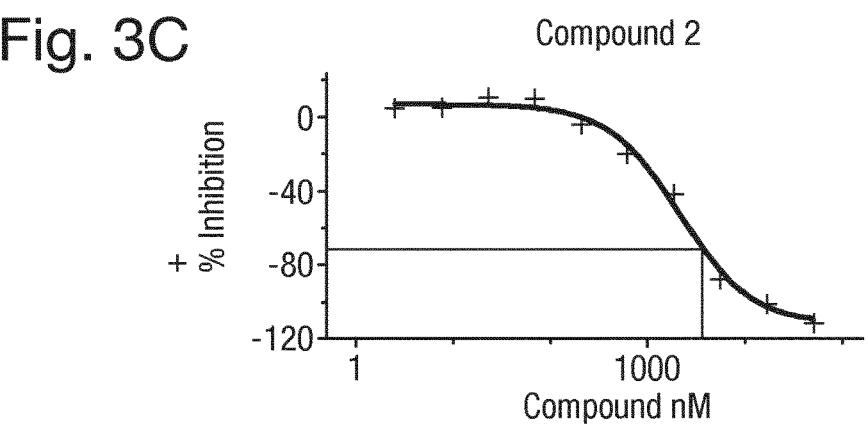
FIG. 3C shows the dose response curve for compound of formula (2).

For the determination of EC50 values (FIGS. 3B and 3C) compounds of formulae (1) and (2) were double or triple diluted in DMSO such that when added to the assay the highest concentration of the test compound was 50 or 100 µM (5% final v/v DMSO). Pre-diluted compounds of formulae (1) and (2) were added at a ratio of 1:1 to 4 ng/mL TNF (final concentration 2 ng/ml), and then incubated at room temperature on a shaker 600 rpm for 1 hour.

10 µl of pre-incubated mixtures of compound of formulae (1) or (2) with TNFα were added to the prepared MSD plate and incubated at room temperature on a shaker for 1 hour.

The plates were then washed with wash buffer (3×50 µl per well). Sulfo-tagged anti-TNF polyclonal antibody was then added to each well and the plates incubated for a further 1.5 hours at room temperature on a shaker.

The plates were then washed (3×50 µl wash buffer per well), followed by the addition of 50 µl MSD Read buffer T plus surfactant (diluted 1 in 2 in H$_2$O) and read on a SECTOR Imager 6000.

For single point assays percentage inhibition was calculated using a control sample without compound.

For EC50s determination results were calculated by standard means using a 4 parameter logistic model (sigmoidal dose response model).

As can be seen from FIG. 3A, the compound labelled "SPD-304", which is representative of TNFα antagonists known in the art, has a % inhibition value of +80%, indicating that this compound inhibits the binding of TNFα to its receptor. In contrast, several of the compounds tested, have negative % inhibition values, indicating that these compound enhance the binding of TNFα to the TNF receptor.

Likewise, dose responses for compounds of formula (1) (FIG. 3B) and formula (2) (FIG. 3C) produce negative inhibition curves. In other words the binding of TNFα to the immobilised ECD-TNFR appears to be enhanced as the concentrations of the compounds increase. For this reason an EC50 (concentration of compound giving 50% of total effect) must be calculated rather than an IC50. In this instance the EC50 for compound of formula (1) was 4.6 µM and the EC50 for the compound of formula (2) was 3.7 µM.

BIA (Biomolecular Interaction Analysis) using surface plasmon resonance can also be used to measure compound induced enhanced binding of TNFα to TNF receptor. For this purpose a Biacore A100/4000 was used. In what is termed an in-solution competition/enhancement assay the extracellular domain of TNF receptor (ECD-TNFR) was immobilised at pH5 to a level of 1 KRU onto a CMS sensor in HBS-P buffer (10 mM HEPES pH 7.4, 0.15 M NaCl, 0.005% Surfactant P20, BIAcore, GE Healthcare).

Compounds were serially diluted two fold so that the highest concentration in the assay was 20 µM. For example a typical assay may use 20 µM, 10 µM, 5 µM, 2.5 µM, 1.25 µM, 0.625 µM, 0.312 µM, 0.156 µM, 0.078 µM, 0.039 µM solution of compound.

Figure 4A:
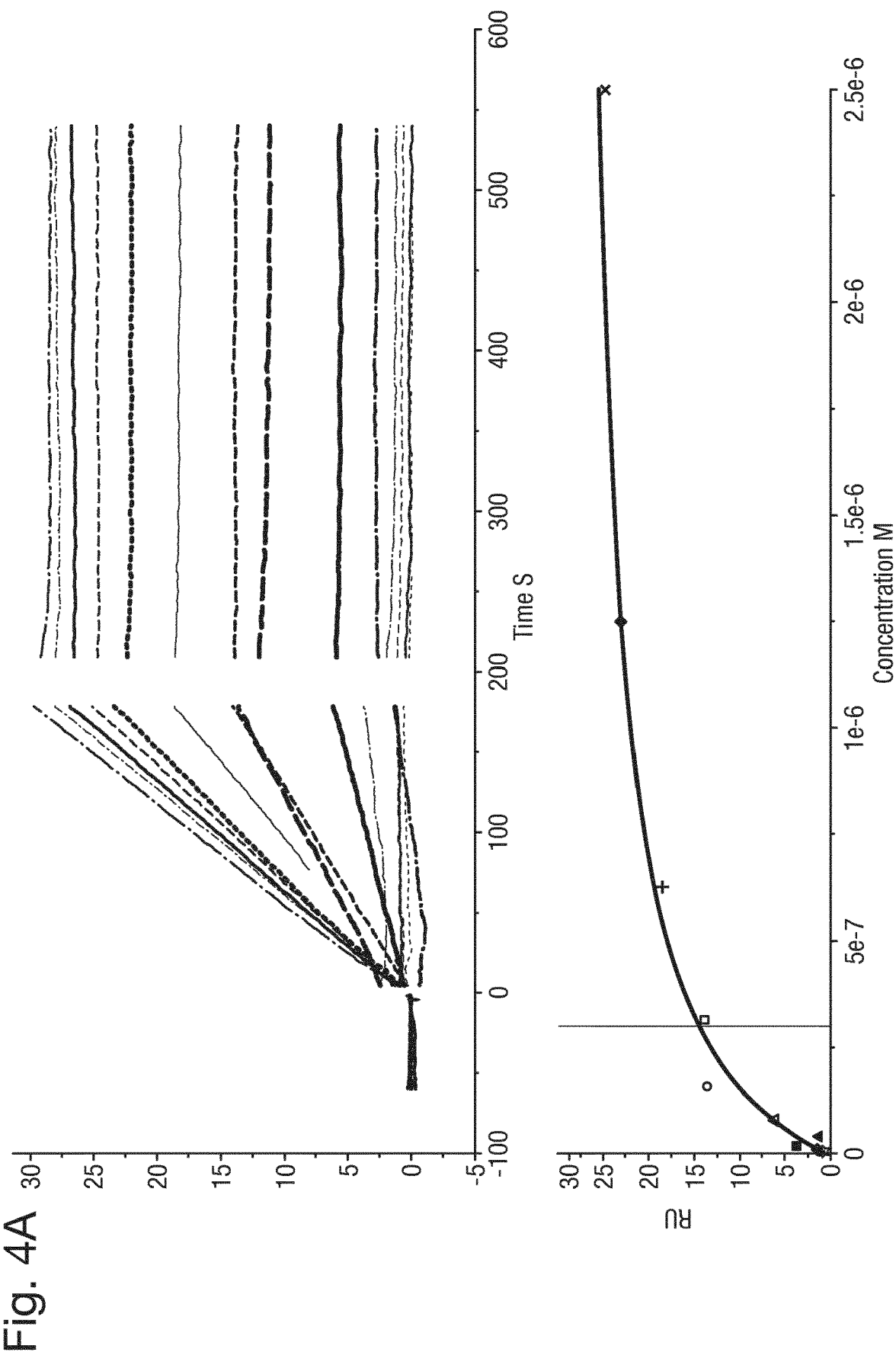
FIG. 4A shows a receptor-ligand binding assay demonstrating the enhanced binding of TNF to the extracellular domain (ECD) of TNFR1 in the presence of compound of formula (1).
Figure 4B:
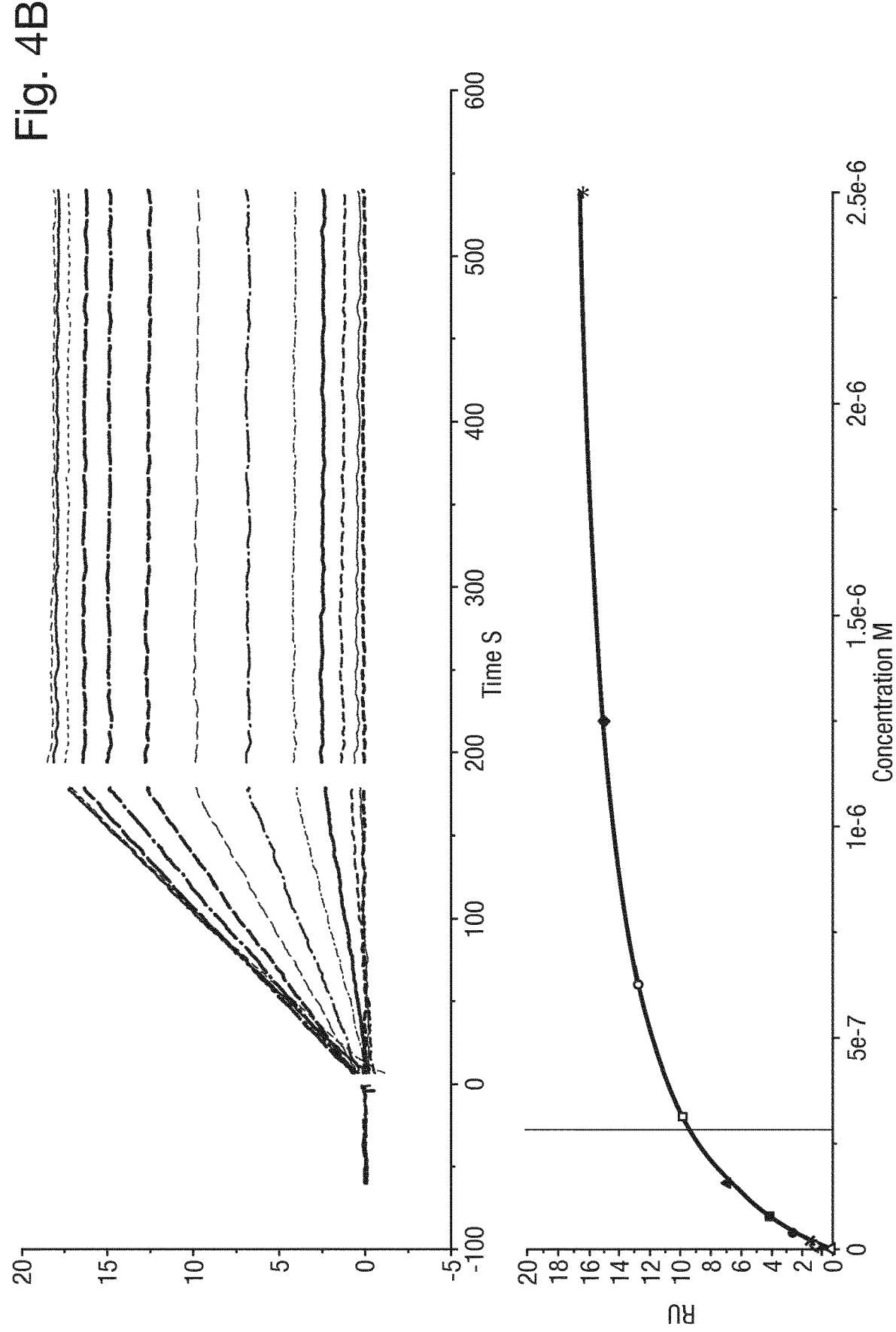
FIG. 4B shows enhanced binding induced by compound of formula (2) in the same assay.

The compounds were mixed with 0.5-1 nM TNFα and equilibrated for at least 5 hours. Control compounds were tested every 10-15 cycles. The TNFα/compound mix was flowed over immobilised TNFR for 3 minutes followed by surface regeneration after each cycle with one 30 ml injection of 10 mM HCL at a flow rate of 30 mL/min. Background subtraction binding curves were analysed using the BIAevaluation software following standard procedures. The EC50 data was determined using a four parameter logistic fit. FIG. 4A and FIG. 4B shows the progress curves for the compounds of formula (1) and formula (2), respectively. The RU (resonance unit) value for TNFα in the absence of compound was subtracted from the curves so these now show only the increase in binding induced by the compounds. The progress curves plateau at higher RU values as the concentration of compound increases. From this an EC50 value can be calculated by determining the concentration of compound that gives a 50% maximal effect using the 4 parameter logistic fit model. In these experiments the EC50 for the compound of formula (1) was calculated to be 298 nM and that for the compound of formula (2) to be 280 nM.

It may be noted that EC50s show inter-assay variability and the conditions for the Biacore assays and MSD assays are very different. As a result the measured EC50s are not expected to be identical for the two assay formats.

Example 4—Mass Spectrometric Analysis of Compound 1 Binding to TNFα

Mass spectrometry was typically performed using a Waters LCT-premier Time-of-Flight mass spectrometer or a Waters SynaptG2 Q-TOF mass spectrometer. Samples were introduced using an Advion Triversa Nanomate nanoflow infusion device which replaces the conventional spectrometer source, sample injection was via an "A" series chip with 5 µM nozzle size at a nominal flow rate of 100 nl/min. Further modifications to the Waters LCT-premier Time-of-Flight mass spectrometer include a customised source cooling device allowing precise control of the source temperature and a commercial pressure regulation device giving precise control over the vacuum conditions in the source region. Together these modifications help retain the TNFα trimer in a native, folded conformation and facilitate the detection of complexes formed with test compounds of weak affinities. Typical settings were Source temperature: 10° C., source pressure 3.74 $e^{-3}$ mbar, analyser pressure 1.54 $e^{-6}$ mbar.

Ions were generated using standard positive ion electrospray conditions resulting in multiple charging of TNFα.

Mass spectrometry is very sensitive to the buffer salts present in the protein sample. Typical buffer salts such as potassium or sodium phosphates have a severely detrimental affect on ionisation. Accordingly protein samples were pre-treated to remove these salts using a Zeba desalt spin column, the protein being exchanged into a mass spectrometry compatible buffer system, typically 50 mM Ammonium Acetate at pH 6.8.

Under soft ionisation conditions when 100% transmission of the trimeric species is observed, under native conditions in a 100% aqueous environment the trimeric form is observed as a charge state envelope comprising the +12, +13 and +14 ions, on addition of 5% v/v DMSO the charge state envelope shifts to lower a m/z (higher z) indicating that, as expected, the organic cosolvent causes partial unfolding in solution of the trimeric species, an increased level of the monomer is also detected. When 10% v/v DMSO is added only the charge state envelope associated with the monomeric form is observed indicating that this level of DMSO disrupts the trimer formation in solution. Typically the test compounds were presented as 10 mM DMSO stock solutions such that when they are incubated with TNFα in solution the final DMSO concentration is 5%. Under soft ionisation conditions the charge state envelope is observed to shift to higher m/z (lower z) compared not only with the 5% DMSO control spectrum but also with the spectrum acquired under 100% aqueous indicating that the test compounds are able to overcome the destabilising effect of the 5% DMSO and afford stabilisation over and above that observed under native conditions. This is evidenced by the changes in the number of charges acquired by the protein under the various conditions described.

The measured "on" rate is an arithmetic product of the rate constant $k_{on}$ and the concentration of the test compound, at high concentrations of the test compound the observed rate is larger than at low concentrations. Experimental measurement of the observed rate by mass spectrometry at different test compound concentrations allows the value of the rate constant ($k_{on}$) to be derived. In a typical experiment a mixture of the test compound and TNFα trimer is prepared at the desired concentration using an Advion Triversa Nanomate robot from stock solutions of TNFα and test compound. The sample is then infused into the mass spectrometer over several minutes during which time the ratio of the free TNFα and TNFα/test compound complex signals in the mass spectrum is recorded. This is repeated for several different test compound/TNFα ratios.

The data recorded for different test compound/TNFα ratios are then fitted to the theoretical one phase logarithmic association curve using Graphpad PRISM v.5 to derive the $k_{on}$ value. This confirmed the low $k_{on}$ value observed on the Biacore.

Test compounds were prepared as 10 mM solutions in dimethylsulphoxide (DMSO). Therefore, it was necessary to establish the effect of DMSO on the native TNFα trimer in the absence of a test compound. DMSO was added to an aqueous solution of TNFα trimer to give a final concentration of 5% v/v and the mass spectrum acquired.

In a 100% aqueous environment, i.e. in the absence of DMSO, a large proportion of TNFα exists in the trimeric form, with a significant proportion of the TNFα monomer. In a 100% aqueous environment, the trimeric form of TNFα is observed as a charge state envelope comprising the +12, +13 and +14 ions (FIG. 5, bottom trace).

Less trimeric TNFα was observed on addition of 5% v/v DMSO. The charge state envelope shifted to a lower mass/charge ratio (m/z) indicating that the DMSO caused partial unfolding of the trimeric species. An increased level of monomeric TNFα was also detected in the presence of 5% v/v DMSO.

Figure 5:
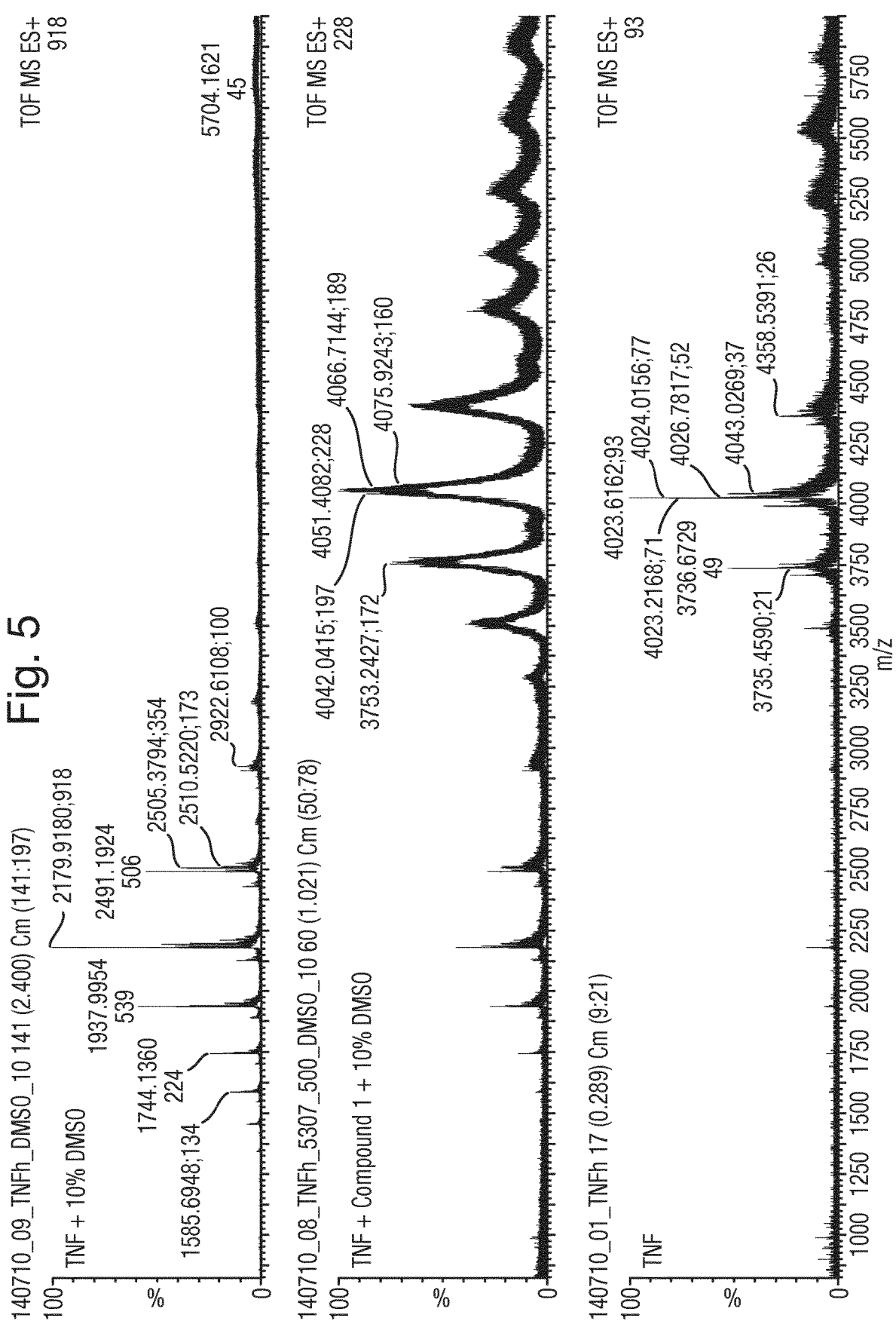
FIG. 5 (bottom trace) shows the deconvoluted mass spectrogram of TNFα in 100% aqueous solution.

When 10% v/v DMSO was added only the charge state envelope associated with the monomeric form is observed indicating that this level of DMSO disrupts trimer formation of TNFα (FIG. 5, top trace).

The compound of formula (1) was added to a solution containing TNFα and 5% v/v DMSO and the mass spectrum acquired. Trimeric TNFα was found to exist in the solution of 5% v/v DMSO in the presence of the compound of formula (1) (FIG. 5, middle trace). The charge state envelope observed for the compound of formula 1-bound TNFα shifts to higher m/z values (exclusively +12 and +11), revealing that the compound of formula (1) not only overcame the weak unfolding influence of the DMSO on TNFα, but also resulted in a stabilization of the trimeric TNFα complex over and above that observed in the absence of DMSO.

To address the concern that it was necessary to have DMSO present in order to weaken the trimeric TNFα complex sufficiently before the test compounds could bind, the experiment was repeated with a water-soluble compound under 100% aqueous conditions. In the absence of DMSO compound bound to the trimeric complex causing the same shift to a higher m/z ratio that was observed when DMSO was present (data not shown). This confirmed that the test compounds do not need DMSO to be present to bind to the TNFα trimer and can exert their stabilizing affect regardless of the presence of a destabilising agent.

Further evidence for the stabilization of the trimeric form of TNFα by the test compounds was obtained from analyzing the samples under harsher ionization conditions that tend to favour breakdown of the native trimeric form into monomers. When TNFα was bound to the compound of formula (1) the quantity of TNFα monomer detected under these conditions was significantly reduced (data not shown). This suggests that the test compounds protect the TNFα trimer from mass spectrometric disruption.

Example 5—Stoichiometry of the TNFα—the Compound of Formula (1) Complex

Figure 6:
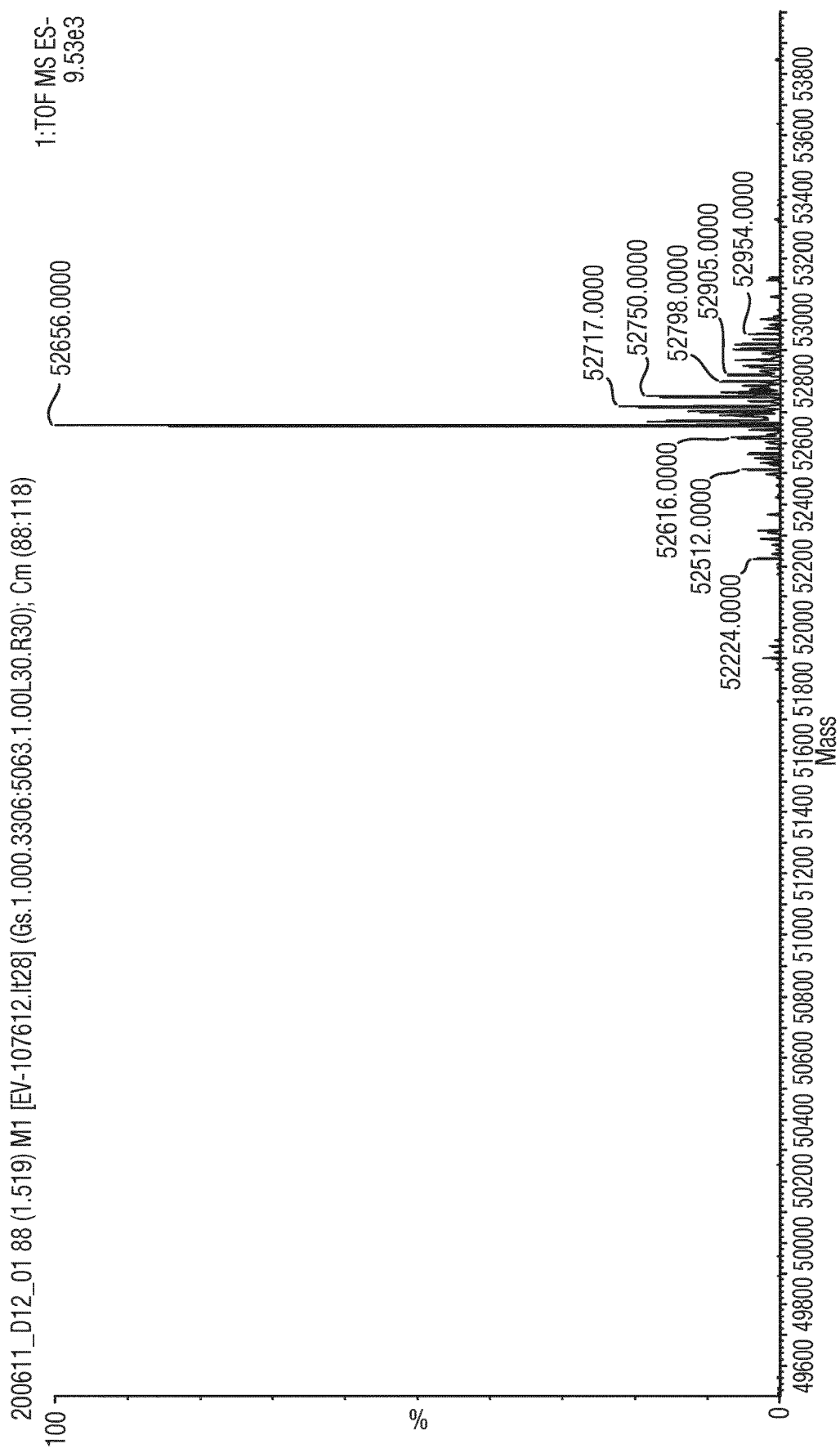
FIG. 6 shows the mass spectrogram of TNFα in a solution containing the compound of formula (1).

Incubation of a library of test compounds, including the compound of formula (1) with TNFα was monitored by mass spectrometry under soft ionization conditions. The data show the stoichiometry of binding as one molecule of the compound of formula (1) per TNFα trimer (FIG. 6). The compound of formula (1) was not observed to bind to the monomeric form of TNFα. There was no evidence for stabilization of the dimeric form of TNFα. This confirms that the test compounds, including the compound of formula (1), have a different mode of action to known compounds, which stabilize the dimeric form of TNFα.

Example 6—Monomer Exchange in TNFα Trimers

Human and mouse homotrimers of TNFα ($H_3$ and $M_3$ respectively) were incubated together and aliquots of the solution monitored by mass spectrometry appearance of the cross species heterotrimers. The mass spectrometric analysis confirmed that monomer exchange between native TNFα trimers was able to occur in solution. The exchange rate was slow and was monitored over a course of 4 hours before full equilibration was achieved (data not shown). The mechanism is unknown, although is it unlikely to involve formation of the dimeric forms as none of these were observed. Monomer exchange is likely to be occurring between pure human and mouse trimers, the mixing of mouse and human trimers simply makes this exchange visible by mass spectrometry.

In a second series of experiments an excess of the compound of formula (1) was incubated with Human TNFα, the excess compound of formula (1) was then removed. Mass Spectral analysis confirmed that a 1:1 complex had been formed between the compound of formula (1) and h-TNFα. Mouse TNFα was now added to this sample which was then subjected to mass spectral analysis over a number of hours. After 18 hours there was no observed change in the composition of the sample. Notably no monomer subunit exchange had occurred, formation of the mixed heterotrimeric species either free as $MH_2$ and $M_2H$ or ligated as $MH_2L$ and $M_2HL$ were not observed. In addition, there was no evidence of formation of the $M_3L$ species and no evidence of formation of the unligated $H_3$ species. This strongly suggests that once the compound of formula (1) is bound to h-TNFα there is no measurable off-rate. Thus, when preincubated with h-TNFα, the compound of formula (1) locked the human trimer, hence no cross species monomer subunit exchange was observed.

The experiment was then repeated in reverse. Excess compound of formula 1 was incubated with Mouse TNFα, the excess compound of formula (1) was then removed. Mass Spectral analysis confirmed that a 1:1 complex had been formed between the compound of formula (1) and m-TNFα. Human TNFα was now added to this sample which was then subjected to mass spectral analysis over a number of hours. The data show clearly that monomer subunit exchange can occur, formation of the mixed heterotrimeric species was observed in both the free ($MH_2$ and $M_2H$) and ligated ($MH_2L$ and $M_2HL$) state. In addition there was evidence of formation of the ligated human homotrimer ($H_3L$), the unligated mouse homotrimer ($M_3$) and for unbound compound of formula (1) (L). This suggests that although a 1:1 complex was formed between compound of formula (1) and the mouse TNFα homotrimer, there is a measurable off-rate. Once this complex ($M_3L$) has dissociated, monomer subunit exchange between the $H_3$ and $M_3$ species proceeds and the liberated ligand is then able to form complexes with all 4 trimer species present in solution. Thus, when preincubated with m-TNFα, the compound of formula (1) did not prevent monomer subunit exchange and the formation of the mixed heterotrimers was observed.

These two experiments were then repeated with the compound of formula (2) instead of the compound of formula (1). The results when the compound of formula (2) was pre-incubated with h-TNFα to give a 1:1 complex and then mixed with unligated m-TNFα were the same as with the compound of formula (1). No monomer subunit exchange was observed, after 18 hours only the $H_3L$ and $M_3$ species were observed in solution confirming that the compound of formula (2) has also no measurable off-rate when complexed with h-TNFα. Thus, when preincubated with h-TNFα, the compound of formula (2) locked the human trimer, hence no cross species monomer subunit exchange was observed.

However, in contrast to the compound of formula (1), when the compound of formula (2) was preincubated with m-TNFα to form a 1:1 complex and then mixed with unligated h-TNFα no monomer subunit exchange was observed, after 18 hours only the $M_3L$ and $H_3$ species were observed in solution. This suggests that the compound of formula (2) has also no measurable off-rate when complexed with m-TNFα. Thus, when preincubated with m-TNFα, the compound of formula (2) locked the mouse trimer, hence no cross species monomer subunit exchange was observed.

Together these data suggest that while the compound of formula (1) and the compound of formula (2) have similar affinities for the human TNFα, the compounds have different affinities for the mouse TNFα trimer, the compound of formula (2) binding more tightly than the compound of formula (1) to the latter.

Example 7—Mass Spectrometric Analysis of Fractions from Size Exclusion Experiments Using TNFα, TNF-R and the Compound of Formula (1)

Figure 7A:
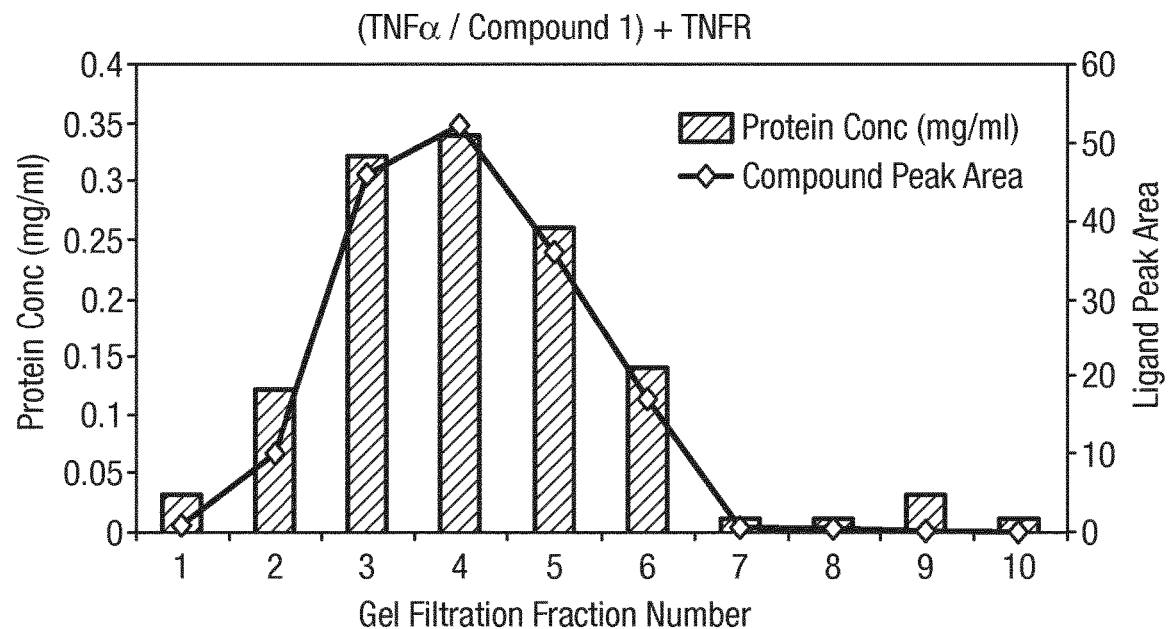
FIG. 7 shows an overlay of the elution profile of a size exclusion chromatography experiment and subsequent mass spectrometric analysis of (A) a sample of TNFα pre-incubated with the compound of formula (1) and then mixed with TNF-R and (B) a sample of TNFα pre-incubated with TNF-R and then mixed with the compound of formula (1).
Figure 7B:
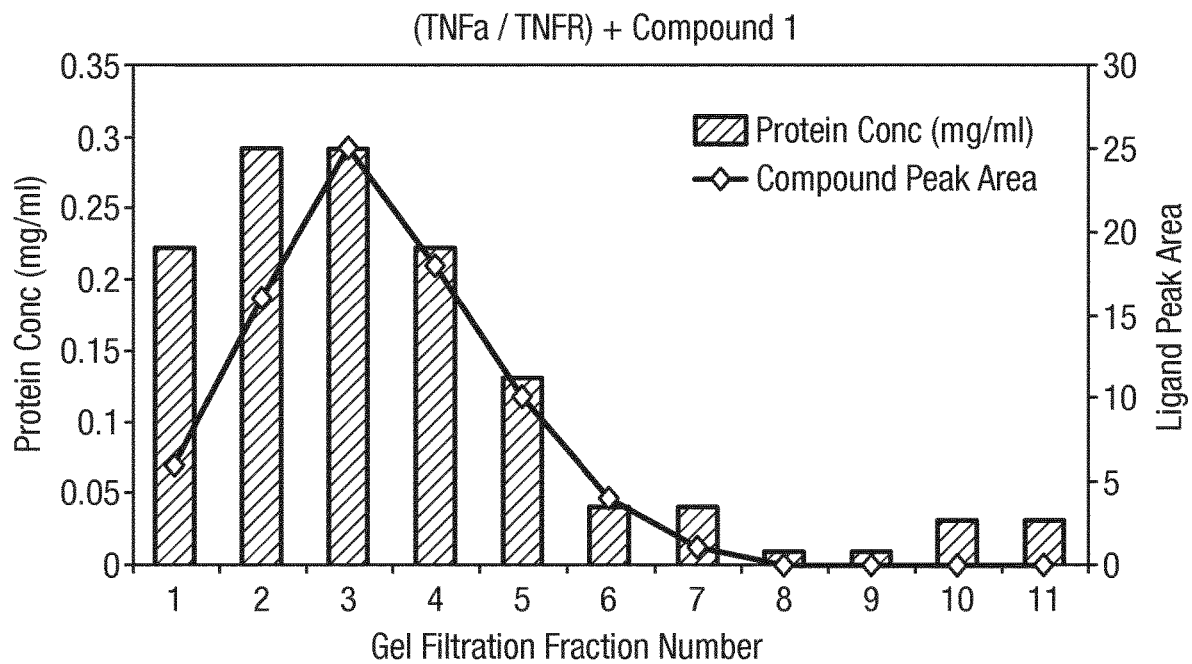

Fractions from size exclusion chromatographic separation of mixtures of TNFα, TNF-R and the compound of formula (1) were analysed by liquid chromatography-mass spectrometry (LC-MS). Two samples were prepared for size exclusion chromatography. In the first sample the compound of formula (1) was pre-incubated with TNFα before the addition of the compound-trimer complex to TNF-R. In the second sample the compound of formula (1) was added to a pre-formed complex of TNFα and TNF-R. The LC-MS analysis revealed that the compound of formula (1) was associated with those fractions that contain the two proteins (FIG. 7), suggesting that regardless of the order of addition the compound of formula (1) is still able to bind to TNFα, i.e. that the compound of formula (1) binds to TNFα even in the presence of TNF-R.

Example 8—Isothermal Calorimetric Analysis of TNFα and the Compound of Formula (2)-TNFα Trimer Complexes Binding to TNF-R TNFα (128 μM) in ITC buffer (50 mM HEPES, 150 mM NaCl, pH 7.4) was incubated for 60 minutes with a DMSO stock of compound 2 giving a final compound concentration of 300 mM in 5% DMSO (test sample). A control sample in which DMSO but not compound was added to the TNFα sample was also incubated for 60 minutes (control).

Following incubation the samples were gel filtered on a Nap 5 size exclusion column (GE Healthcare). The column was equilibrated with 15 ml of ITC buffer prior to the addition of 500 μl of sample which was run into the column and then eluted using 1 ml of ITC buffer. This process separates the TNF and compound bound TNF from free compound and DMSO.

Absorbance readings at 280 nm were used to determine the concentration of TNFα in the test sample or the control following elution from the NAP 5 column and the samples were diluted to a TNFα concentration of 64 μM.

200 μl of the extracellular domain (ECD) of TNFR1 (10 mM) was loaded into the sample cell of an AutoITC200 (GE Healthcare) automatically (using the Plates Standard B protocol). In 2 experiments 40 μl of either the test sample or the control was loaded into the injection syringe automatically using the same protocol.

The ITC experiments were performed using the ITC injection protocol described on the Isotherm plots (FIGS. 8A and B) at 25 degrees centigrade stirring at 1000 rpm.

Data was collected and analysed using GE Healthcare ITC applications in Origin 4.0 Software and the results were calculated using a one-site binding algorithm.

Figure 8A:
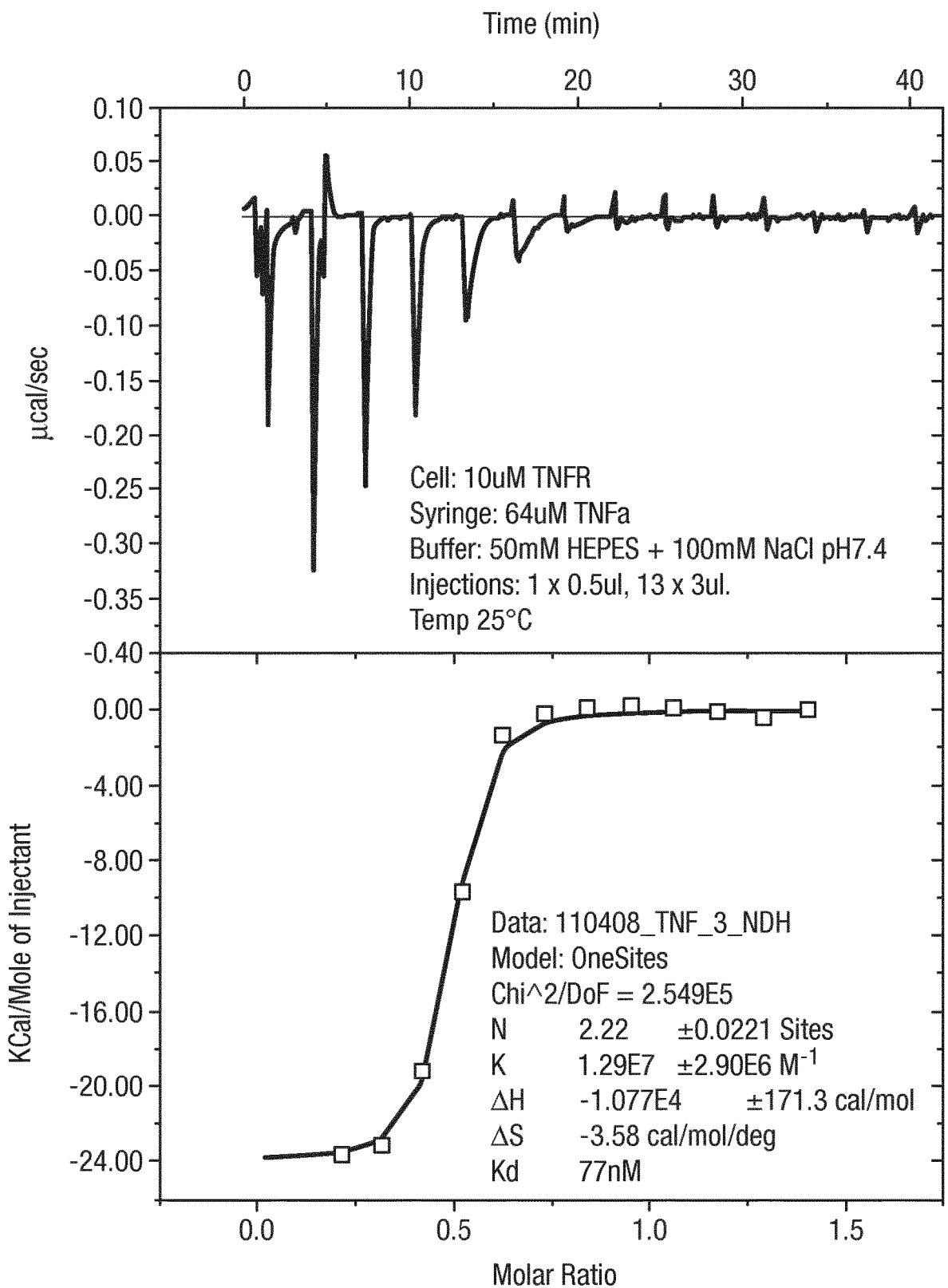
FIG. 8 shows (A) the results of isothermal calorimetric analysis of the binding of TNFα to TNF-R and (B) the results of isothermal calorimetric analysis of the binding of TNFα to TNF-R wherein the TNFα has been pre-incubated with the compound of formula (2).
Figure 8B:
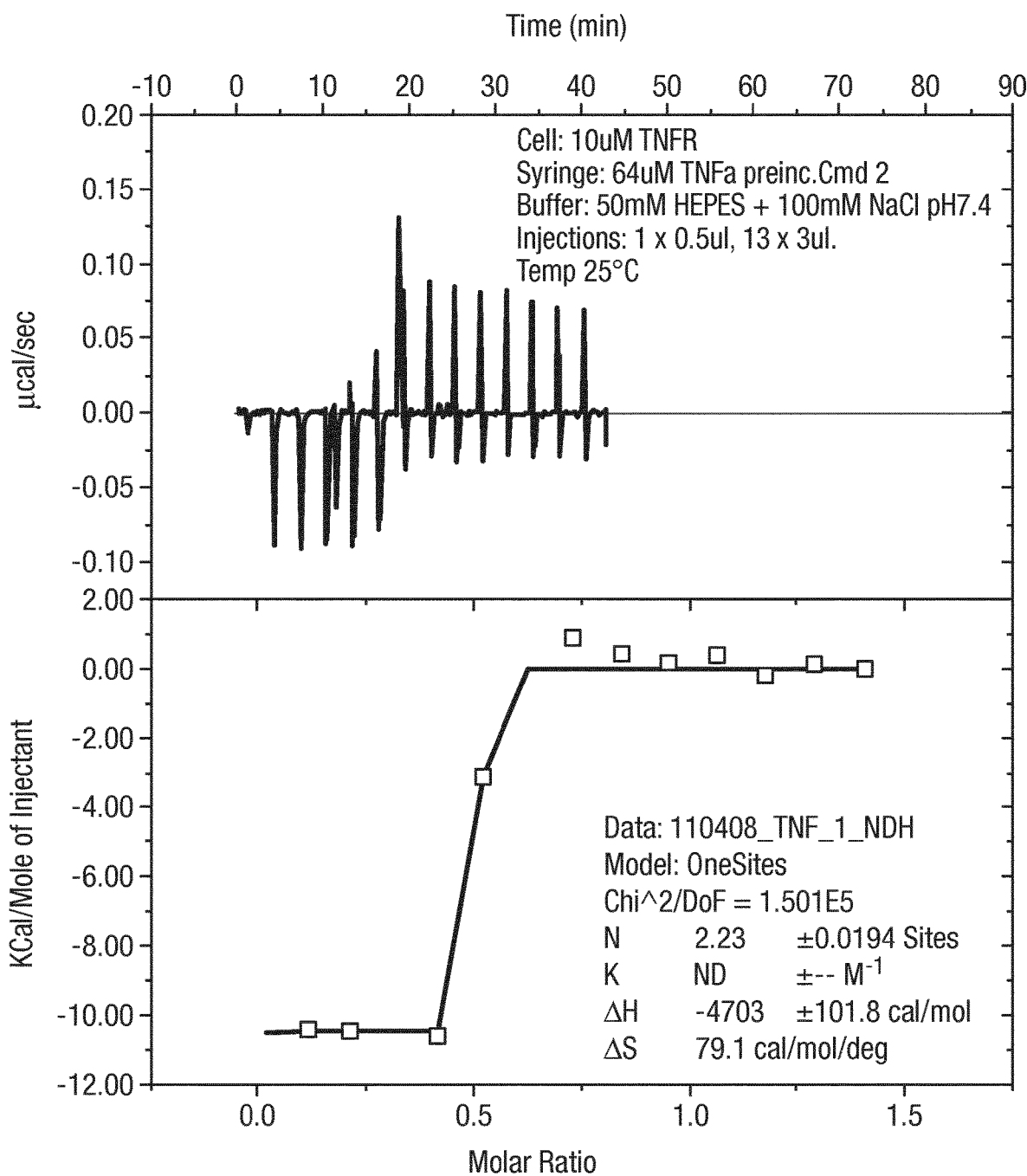

The $K_D$ of TNFα binding to TNF-R in the absence of any test compound was calculated to be 77 nM (FIG. 8A). The $K_D$ of TNFα binding to TNF-R in the presence of the compound of formula (2) was below the sensitivity range of the calorimeter and so could not be accurately calculated. However, the calorimeter has a lower sensitivity boundary of about 1 nM. Therefore, the $K_D$ of TNFα binding to TNF-R in the presence of the compound of formula (2) must be 1 nM or lower (see FIG. 8B).

Example 9—Crystal Structure of Trimeric TNFα Bound to the Compound of Formula (1)

Figure 9:
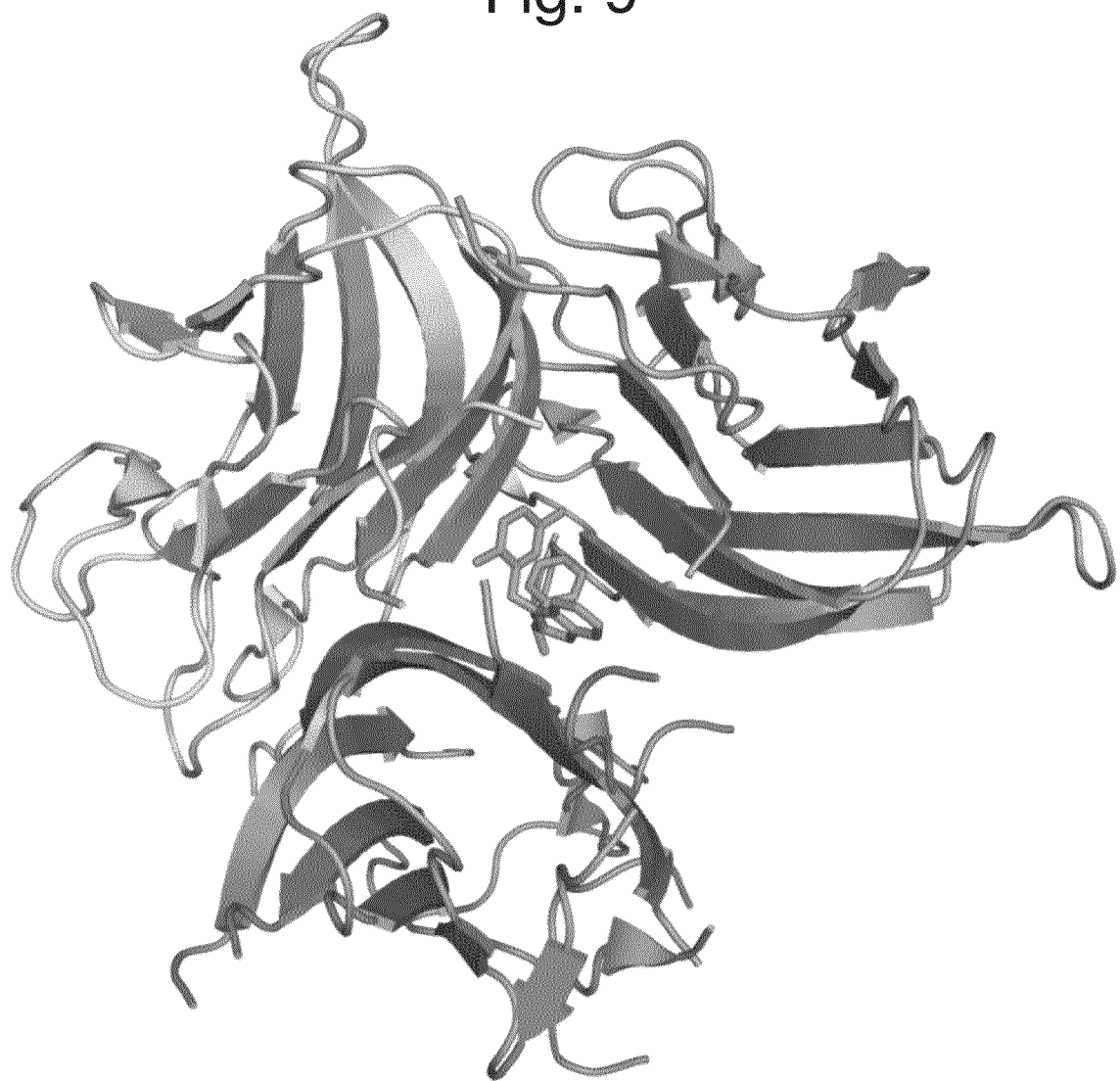
FIG. 9 shows the crystal structure of a compound of formula (1)-trimeric TNFα complex.

TNFα was pre-incubated with the compound of formula (1) and the resulting compound-trimer complex crystallised. The crystal structure of the compound-trimer TNFα complex was determined using X-ray crystallography. The crystal structure of the complex with a resolution of 2.2 Å is shown in FIG. 9. The compound can be seen in the middle of the trimer which is no longer symmetrical.

Example 10—Neutralisation of TNFα by Compounds of the Invention

The L929 neutralisation assays were carried out using the protocol disclosed in Baarsch M J J et al (Immunol Methods 1991; 140: 15-22) and Galloway C J et al J (Immunol Methods 1991; 140: 37-43).

Briefly, L929 cells (ECACC, 85011425) were cultured in culture medium consisting of RPMI 1640 (Gibco) containing 10% FCS (PAA), 2 mM glutamine (Gibco), 50 U/ml penicillin (Gibco) and 50 μg/ml streptomycin (Gibco). When they were subcultured, the cells were washed three times with 10 mL Dulbecco's phosphate-buffered saline without calcium and magnesium (Gibco) and 3 ml of trypsin-EDTA (Gibco) was then added for 2 minutes to remove the cells from the flask. Culture medium was added to neutralise the trypsin and the cells pipetted up and down to remove any clumps.

The L929 cells were split 1/2 or 1/3 the day before use and cultured for a further 24 hours. The flasks were then trypsinised as above and $2 \times 10^4$ cells in 100 μl were added per well of a 96 well flat-bottomed plate (Becton Dickinson). The plates were cultured for 24 hours before the assay was set up.

Serial dilutions were made from DMSO stocks of the compounds. Typically a 9 point titration curve would be generated by double diluting from a concentrated solution of compound to give a final assay concentration of 25, 12.5, 6.25, 3.125, 1.56, 0.78, 0.39, 0.2, 0.1 μM.

The assay medium was the same as culture medium but also contained 1 μg/ml actinomycin D (Sigma). The medium was flicked off the plates and the assay samples plus TNFα, standards and controls were added in 100 μl volumes in duplicate. Plates were incubated for a further 16 hours and then 10 μl per well of a 5 mg/ml methylthiazoletetrazolium (MTT; Sigma) solution in culture medium was added for a further 4 hours. The reaction was stopped by the addition of 100 μl of solubilisation buffer containing 20% sodium dodecyl sulphate (SDS, BDH) dissolved in 50% dimethyl formamide (DMF; BDH) and 50% deionised water.

After overnight incubation at 37° C. to allow the dye to dissolve, the plates were read on a Multiskan EX plate reader (Labsystem) at 570 nm with subtraction at 630 nm. Data were analysed using the Genesis software package.

Figure 10:
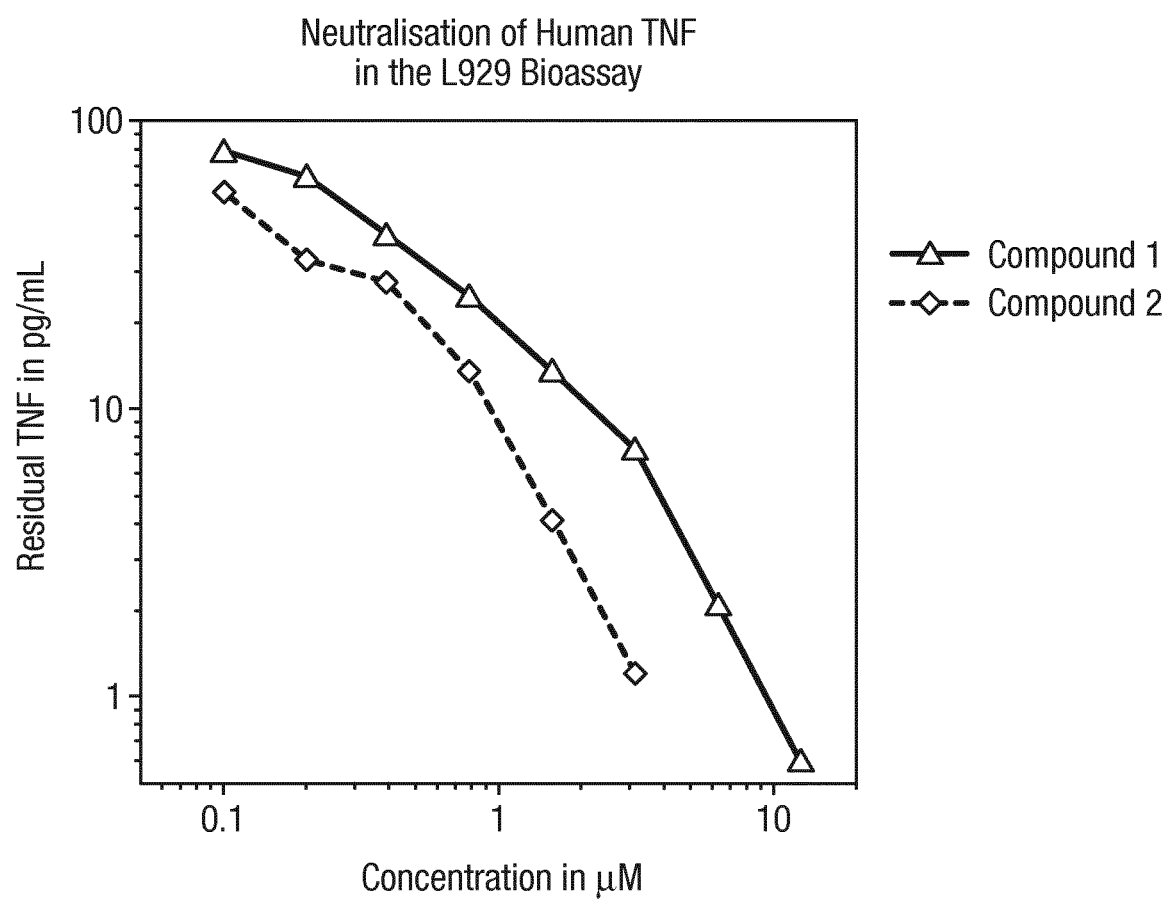
FIG. 10 shows a graph of the neutralisation of human TNFα by the compound of formula (1) and the compound of formula (2) as measured in terms of the concentration of the compound of formula (1) ( ) and the compound of formula (2) 0) against residual human TNFα concentration (pg/ml) measured using an L929 murine fibrosarcoma cell-killing assay.

Both the compound of formula (1) and the compound of formula (2) inhibited the cell killing activity of human TNFα (FIG. 10), indicating that both the compound of formula (1) and the compound of formula (2) were able to inhibit human TNFα-induced signalling through TNF-R. In this instance the compound of formula (1) gave an $IC_{50}$ value of 306 nM and the compound of formula (2) gave an $IC_{50}$ value of 125 nM. The protocol was repeated using the compound of formula (3), which was also found to inhibit human TNFα-induced signalling through TNF-R. Thus, the compound of formula (3) gave an $IC_{50}$ value of 21 nM.

Example 11—Inhibition of TNFα-Induced IL-8 Production by the Compound of Formula (1)

Venous blood from healthy donors was collected by venupuncture into sodium/heparin containing tubes (BD Biosciences). Peripheral blood mononuclear cells (PBMC) were isolated by density gradient centrifugation with Ficoll Paque (Amersham Biosciences). Briefly, 10 mL of blood was diluted 1:1 (v/v) with RPMI 1640 (Gibco) and carefully layered onto 20 mL Ficoll Paque. Cells were spun down for 30 minutes (min) at 470 g, the PBMC collected, washed once in RPMI 1640 and any remaining contaminating erythrocytes lysed in erythrocyte lysis buffer (1 g/L $KHCO_3$, 8.3 g/L $NH_4Cl$, 0.0372 g/L EDTA). Isolation of monocytes from the PBMC was performed using CD14+ Magnetic Micro-Beads (Miltenyi Biotec) according to the manufacturer's instructions. Briefly, PBMC were resuspended in Dulbecco's modified Eagle's medium containing 5% BSA (Sigma) and 2 mM EDTA (Sigma) at $1 \times 10^7$ cells/ml. 254 of CD14 MicroBeads per $10^7$ total cells were incubated for 15 min at room temperature. The magnetic separation was performed using a LS column (Miltenyi Biotec). Prior to application of the cell/bead mixture to the column, the column was placed in the magnetic field and washed twice with 5 mL buffer. The cell suspension was then applied onto the column, in the magnetic field. Monocytes binding $CD14^+$ MicroBeads were retained on the LS column while the remaining PBMC passed through the column. To isolate monocytes, the column (containing the retained cells) was then removed from the magnet and placed in a collection tube. 5 mL buffer were add to the column and the $CD14^+$ cells collected from the column by applying a syringe plunger to the top of the column. The collected cells were washed once in RPMI 1640.

An 11 points 3-fold serial dilution (blank included) of the compounds (stock concentration 10 mM) was performed in DMSO in a 96 well round-bottomed plate. Purified monocytes were washed by centrifugation (300 g for 5 minutes) and resuspended in complete medium at a concentration of $1 \times 10^6$ cells/mL. 1604 of this cell population was incubated at 37° C. in a 96 well round-bottomed plate with 404 of the compounds and TNFα (final concentration ~1 ng/ml) in RPMI 1640 or relevant controls in triplicate.

After 18 hours the plate was spun down (300 g, 5 min) and the supernatants collected for cytokine measurement.

Human IL-8 was measured in the cell culture supernatants using enzyme-linked immunosorbent assay (ELISA) kits from R&D Systems Ltd. according to the manufacturer's instructions. The substrate used for the ELISAs was TM Blue (Serologicals Corporation). Plates were read at a wavelength of 630 nm with correction at 470 nm. The compound of formula (1) inhibited the TNFα-induced production of IL-8 in a concentration dependent manner (FIG. 11), with an $IC_{50}$ value of 454.1 nM.

Example 12—Inhibition of TNFα-Induced NF-κB Activation by the Compound of Formula (2)

Stimulation of HEK-293 cells by TNF-alpha leads to activation of the NF-kB pathway. The reporter cell line used to determine TNF alpha activity was purchased from Invivogen. HEK-BlueTM CD40L, is a stable transfectant expressing SEAP (secreted alkaline phosphatase) under the control of the IFN-beta minimal promoter fused to 5 NF-kB binding sites. Secretion of SEAP by these cells is stimulated in a concentration dependent manner by TNF-alpha (0.5 ng/ml), IL-1-beta (0.5 ng/ml) and an activating anti-human TNFR1 antibody (300 ng/ml).

Compounds were diluted from 10 mM DMSO stocks (final assay concentration 0.3%) to generate a 10 point 3 fold serial dilution curve (30,000 nM to 2 nM final concentration). They were mixed with stimulating ligand for 1 hour in a 384 well microtitre plate. Freshly thawed and washed cells were added to the compound/stimulus mixture and further incubated for 18 hours. SEAP activity was determined in the supernatant using the colorimetric substrate Quanti-blue TM (Invivogen).

Percentage inhibitions for compound dilutions were calculated between a DMSO control and maximum inhibition (by excess control compound) and an $IC_{50}$ calculated using xlfit (4 parameter logistic model) in Activity Base.

The specific activity of each compound against the TNF-alpha response was compared to that seen with the counterscreens (IL-1beta and anti-human TNFR1 antibody).

Figure 12A:
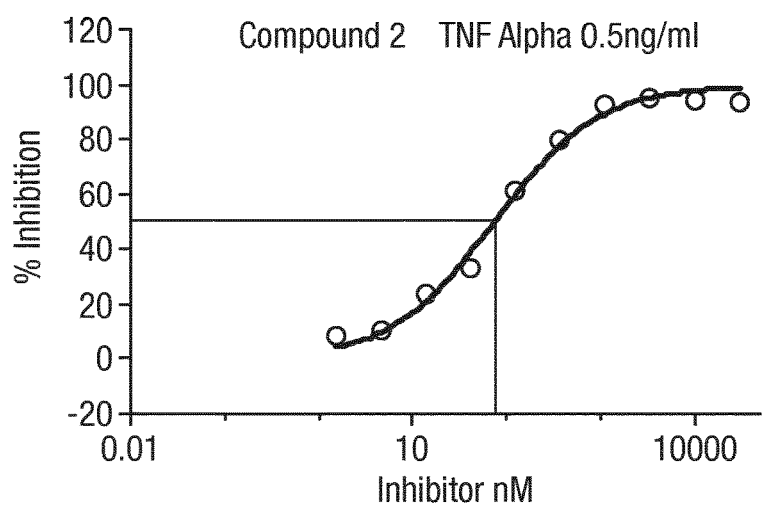
FIG. 12 shows a graph of the concentration of the compound of formula (2) (nM) against % inhibition of NF-κB activation in HEK293 cells in the presence of (A) TNFα (0.5 ng/mL), (B) IL-1β (0.5 ng/mL) and (C) an activating TNF-R1 antibody (300 ng/mL).
Figure 12B:
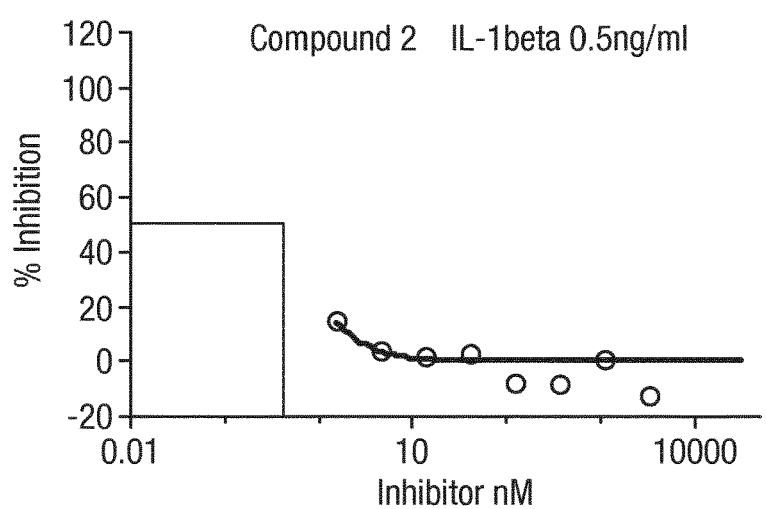
Figure 12C:
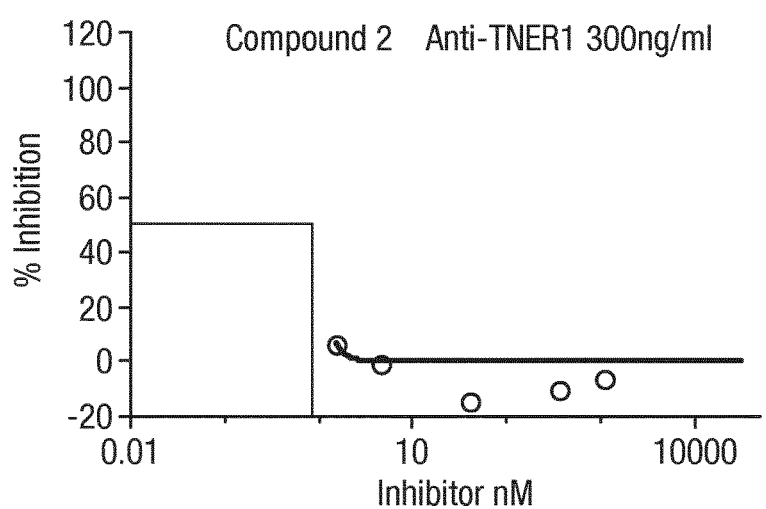

The compound of formula (2) inhibited the activation of NF-κB by TNFα in a concentration-dependent manner, with an $IC_{50}$ of 113 nM (FIG. 12A). In contrast, the compound of formula (2) did not inhibit the activation of NF-κB by IL-1β (FIG. 12B) or the activating TNF-R1 antibody (FIG. 12C). $IC_{50}$ values of more than 30,000 nM were obtained in each case. Therefore, the compound of formula (2) specifically inhibits TNFα-induced signalling through the TNF-R1, but has no effect on NF-κB activation induced by other signalling pathways (such as by IL-1β), or when the initiation of signalling from the TNF-R1 by TNFα is bypassed (such as by using an activating TNF-R1 antibody).

Example 13—Determining the Kinetics of Binding to TNFα

Figure 13A:
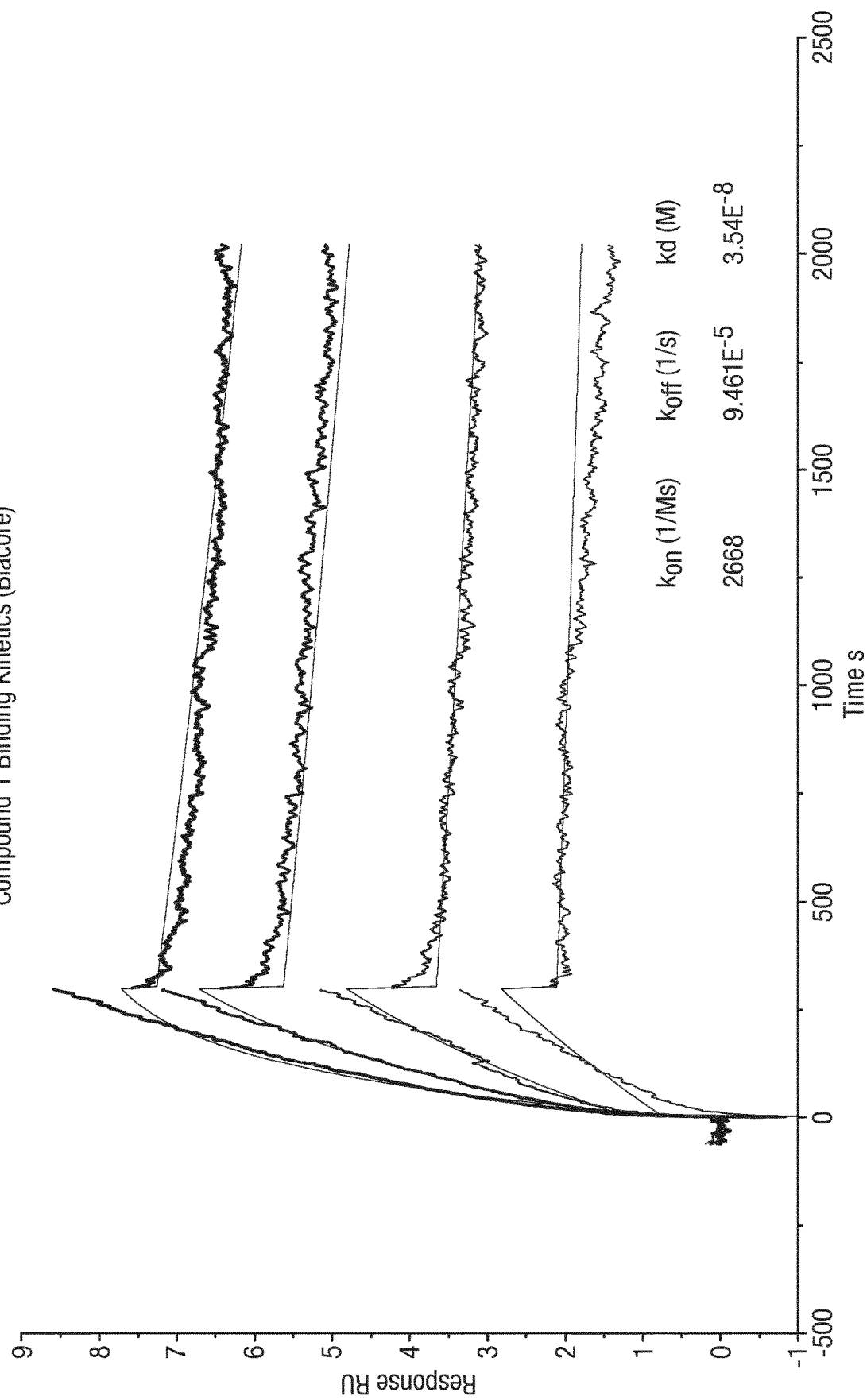
FIG. 13A shows the binding kinetics of the compound of formula (1) with TNFα over time as measured using surface plasmon resonance.

Surface plasmon resonance was used to measure the association rate, the dissociation rate and the affinity of the compounds of formulae (1) and (2) for TNFα (FIGS. 13A and B). For the purpose of this study a Biacore T100/T200 was used.

TNFα was immobilised at pH5 to a level of 5-8 KRU onto a CMS sensor in HBS-P buffer (10 mM HEPES pH 7.4, 0.15 M NaCl, 0.005% Surfactant P20, BIAcore, GE Healthcare). The TNFα was then equilibrated in HBS-P with 5% DMSO for at least 5 hours. The samples were diluted from 10 mM stocks into DMSO matched buffer and left to solubilise for at least 5 hours. The flow rate was 304/min.

This assay was performed by adding 4 or 5 concentrations of compound starting from a highest concentration of 25 μM for compound of formula (1) and 1 μM for compound of formula (2) and then serially diluting this sample. Background subtraction binding curves were analysed using the BIAevaluation software following standard procedures. Binding, affinity and kinetic parameters were determined using Biacore software. The kinetic data were fitted using the levenberg marquardt algorithm.

The experiment showed that these compounds bind immobilised TNFα very slowly as evidenced by a $k_{on}$ of $2.668e^3$ $M^{-1}$ $s^{-1}$ for compound of formula (1) (FIG. 13A) and $1.119e^3$ $M^{-1}$ $s^{-1}$ for compound of formula (2) (FIG. 13B). They also have remarkably slow dissociation rates which appears to be a characteristic of compounds with this mode of action. The dissociation rate constant ($k_{off}$) for the compound of formula (1) is $9.46e^{-5}$ s$^{-1}$ and for compound of formula (2) is equal to $2.24e^{-5}$ s$^{-1}$. This equates to a dissociation half-life ($t_{1/2}$) of over 2 hours and 8 hours, respectively. The dissociation constant ($K_D$) can be calculated from the ratio of the two constants $k_{off}/k_{on}$. In this experiment the $K_D$ values for the compound of formula (1) and for the compound of formula (2) are 35 nM and 2 nM, respectively. This is significantly lower than the $EC_{50}$s determined on the Biacore shown in Example 4 and is likely to reflect the differences in the format of the assays. Additionally the form of TNFα differs in that in the kinetic assay of Example 13 the TNFα is immobilised.

The experiment was repeated to measure the association rate, dissociation rate and affinity of the compound of formula (3) for TNFα (FIG. 13C). The compound of formula (3) was found to have a $k_{on}$ of 5470 M$^{-1}$ s$^{-1}$, a dissociation rate constant of $4.067e^{-5}$ s$^{-1}$ and a $K_D$ of 7 nM.

Example 14—the Compound of Formula (1) and the Compound of Formula (2) Antagonise TNFα Activity In Vivo In separate studies, compounds of formula (1) and formula (2) were mixed with 20 μM solutions of TNFα dissolved in phosphate buffered saline (PBS) to a concentration of 2 μM, 20 μM and 200 μM. The ratio of each compound to TNFα was, therefore, 0.1:1 (sample 1), 1:1 (sample 2) and 10:1 (sample 3). The solutions were incubated at room temperature for 3 hours to allow the compounds to bind to TNFα, prior to gel filtration using a Zeba Spin desalting column (Thermo Scientific). This process separates protein bound compound and free compound. A control sample containing PBS only was processed in the same way to provide a vehicle control for the study. The concentration of eluted protein was determined using a Nanodrop (ND-1000). The TNFα: compound complexes were diluted in PBS to a concentration for injection of 0.03 μg/kg For the study, typically, each group contained 10 male Balb/c mice (Charles River) apart from an anti-human TNFα antibody positive control, which used a set of 5 mice. Antibody control mice were administered anti-hTNFα at 10 mg/kg (1004) by intraperitoneal (i.p.) injection five minutes before (t=−5) being given an i.p. injection of either PBS or hTNFα at 0.1 μg/kg (t=0).

Test mice were injected i.p. at t=0 with 1004 of either gel filtered vehicle (PBS), hTNFα (0.03 μg/kg) or samples 1, 2 and 3 (compound bound to TNFα at a ratio of 0.1:1, 1:1 and 10:1, respectively).

Compound only mice were also included in the study to assess the effect of compound on neutrophil recruitment.

All mice were killed by cervical dislocation two hours post-injection of hTNFα (t=2 h) and the peritoneal cavity was lavaged with 3 mL of FACS buffer (500 mL PBS containing 2 g bovine serum albumin, 6 mL HEPES buffer and 500 mL EDTA). Lavage fluid was aspirated and neutrophil numbers were assessed by staining cells with anti-Gr1 PE and anti-CD45 FITC by FACS as detailed below.

100 μL of lavage fluid from each sample was aliquoted into FACS tubes. A FACS cocktail was made up using anti-GR-1 PE (BD cat #553128 Lot #75542) at 1 in 39 dilution and anti-CD45 FITC (BD cat #553080 Lot #80807) at 1 in 19 dilution in FACS buffer. Fc block (BD Cat #553142 Lot #87810) was prepared 1 in 10 with FACS buffer and 10 μL added to each sample 5 minutes before adding the antibody cocktail. 10 μl of antibody cocktail was added to each tube containing the 1004 of sample. Samples were then left for 20 mins on ice. 1 mL of FACS Lyse solution (BD Cat #349202 Lot #29076, diluted 1:10 in dH$_2$0) was added to each tube, mixed and left at room temperature for 5 minutes. 1 mL of FACS Buffer was then added to each tube and centrifuged at 400 g for 5 minutes. The FACS buffer was then carefully poured off and the tip of the tube dabbed on absorbent paper to leave the tube completely dry. Then 3004 of 1 in 10 Reference Bead solution (Sigma cat #P2477 Lot #116K1612) diluted in FACS buffer was added to each tube.

Samples were analysed using FACScalibur II and FloJo software.

Figure 14A:
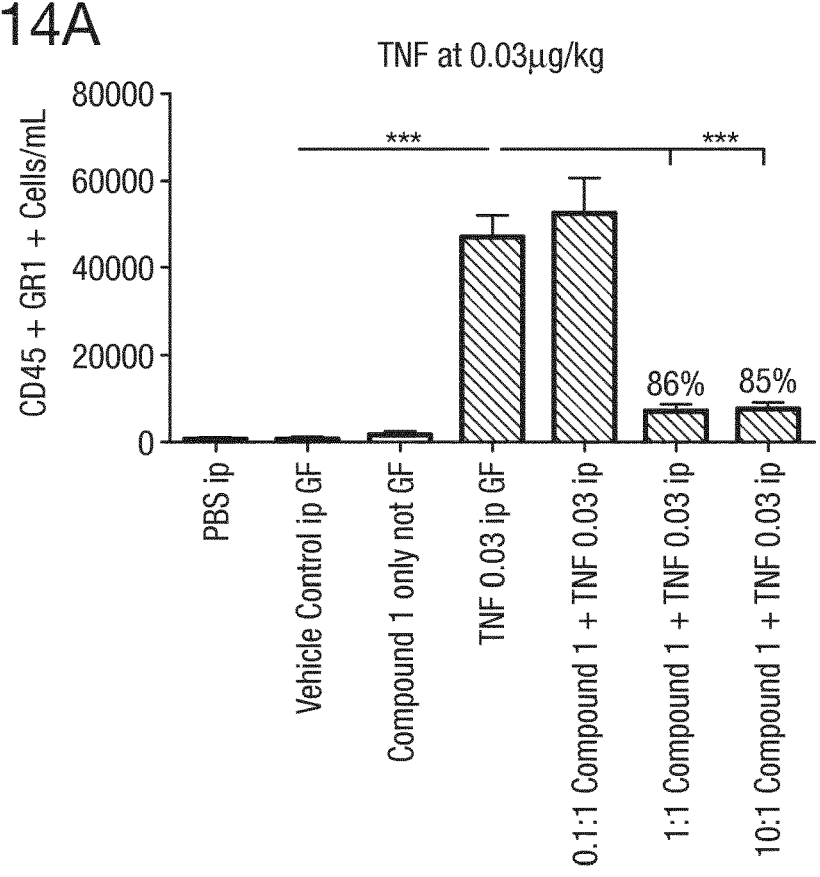
FIG. 14 shows the level of neutrophil recruitment in response to TNFα alone or TNFα that has been pre-incubated with increasing concentrations of (A) the compound of formula (1) or (B) the compound of formula (2) and administered by intraperitoneal injection (ip.).
Figure 14B:
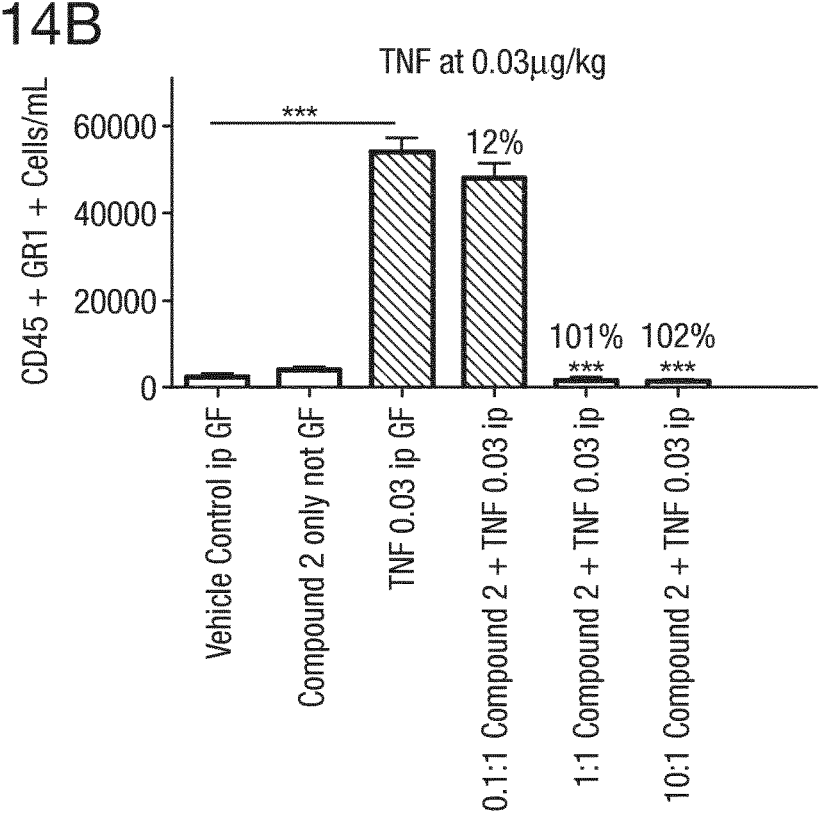

FIG. 14 shows the results for the compound of formula (1) (A) and the compound of formula (2) (B). Vehicle alone had a negligible effect on neutrophil recruitment as did compound alone (slightly higher in (B)). Sample 1 from each study (ratio compound:TNFα 0.1:1) was not significantly different from adding TNFα in the absence of the compound. Sample 2 (1:1) and sample 3 (10:1) showed significant inhibition of neutrophil recruitment, (86% and 85%, respectively). Similarly, sample 2 and sample 3 of the compound of formula (2) showed significant inhibition of neutrophil recruitment, (101% and 102%, respectively). The antibody control mice showed 100% inhibition of neutrophil recruitment (data not shown).

In a further experiment, mice were treated with hTNFα (0.3n/ml) and the compound of formula (1) was administered orally (p.o.).

The compound of formula (1) was made into a suspension in 1% methylcellulose vehicle using a covaris machine.

An anti-human TNFα monoclonal antibody (anti-hTNFα, UCB) was also utilised as a positive control in this study.

Ten male Balb/c mice were used per group except in the group that received anti-hTNFα for which 4 mice were used.

Mice received 1004 of either vehicle (1% methylcellulose) or compound of formula (1) at 30 mg/kg or 100 mg/kg p.o. 30 minutes (t=−30) or anti-hTNFα at 10 mg/kg i.p. 5 minutes (t=−5) prior to being injected with human TNFα. At t=0 mice were injected with 1004 i.p. of either PBS or hTNFα at 0.03 μg/kg.

All mice were killed by cervical dislocation two hours post-injection of hTNFα (t=2 h) and the peritoneal cavity was lavaged and neutrophil numbers measured as described above.

Figure 15:
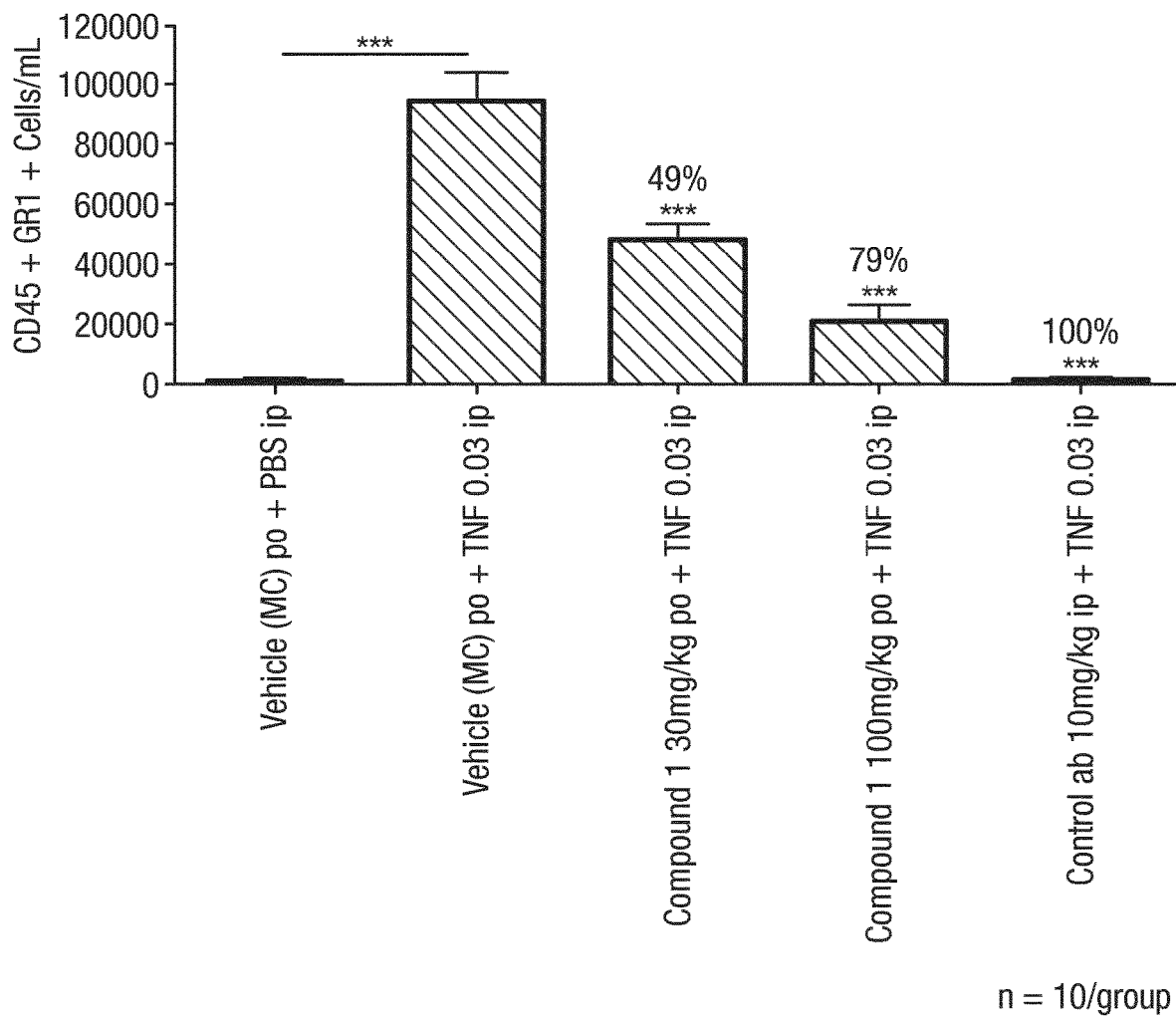
FIG. 15 shows the level of neutrophil recruitment in response to TNFα, alone or in the presence of increasing concentrations of the compound of formula (1) administered orally.

Oral administration of 30 mg/kg and 100 mg/kg of compound of formula (1) reduced TNFα stimulated neutrophil recruitment into the peritoneal cavity by 49% and 79%, respectively (FIG. 15). The positive control antibody (10 mg/kg) given by i.p. injection completely inhibited neutrophil recruitment.

Therefore, the compound of formula (1) can antagonise TNFα activity in vivo not only when premixed with the TNFα and administered by the i.p route but also when it is administered orally.

Example 15—Analysis of TNFα Trimer Stabilisation by the Compounds of Formulae (1) and (2)

A fluorescence probed thermal denaturation assay was performed to assess the effect of the compounds on the thermal stability of TNFα as a measure of compound binding. The reaction mix contained 5 μl of 30×SYPRO® Orange dye (Invitrogen) and 5 μl of TNFα (at 1.0 mg/ml), 37.5 μl PBS, pH 7.4 and 2.5 μl of compound (at 2 mM in DMSO). 10 μl of the mix was dispensed in quadruplicate into a 384 PCR optical well plate and was run on a 7900HT Fast Real-Time PCR System (Agilent Technologies). PCR System heating device was set at 20° C. to 99° C. with a ramp rate of 1.1° C./min; fluorescence changes in the wells were monitored by a Charge-coupled device (CCD). The fluorescence intensity increase was plotted as a function of temperature and the $T_m$ calculated as the midpoint of this denaturation curve (determined as the point of inflection) (Table 1).

Stabilising TNFα is indicated by an increase in Tm. The compounds of formulae (1) and (2) both increase the Tm of TNFα (as shown in Table 1). Therefore, both the compounds of formulae (1) and (2) increase the stability of the TNFα trimer.

Table 1 shows the thermal transition midpoint (Tm) of TNFα in the presence of either compound (1) or (2).

| Sample | Tm (° C.) (mean ± sd) | Tm difference (=(TNF + cpd) − (TNF + DMSO)) |
| --- | --- | --- |
| TNFα + 5% DMSO | 61.4 ± .86 (n = 13) | — |
| TNFα + 5% DMSO + compound (1) | 73.2 ± 0.6 (n = 4) | 11.8 |
| TNFα + 5% DMSO + compound (2) | 78.5 ± 1.1 (n = 4) | 17.1 |

Example 16—Fluorescence Polarization Assay to Determine the Effect of Compounds of Formula (1), (2) and (3) on the Binding of the Compound of Formula (4) to TNFα

The compound of formula (1) was tested at 10 concentrations starting from 100 μM at a final concentration of 5% DMSO, by pre-incubation with TNFα for 60 minutes at ambient temperature in 20 mM Tris, 150 mM NaCl, 0.05% Tween 20, before addition of the compound of formula (4) and a further incubation at ambient temperature overnight. The final concentrations of TNFα and the compound of formula (4) were 50 nM and 10 nM respectively in a total assay volume of 25 μl. Plates were read on an Analyst HT reader. An $IC_{50}$ was calculated using xlfit (4 parameter logistic model) in Activity Base.

Figure 16:
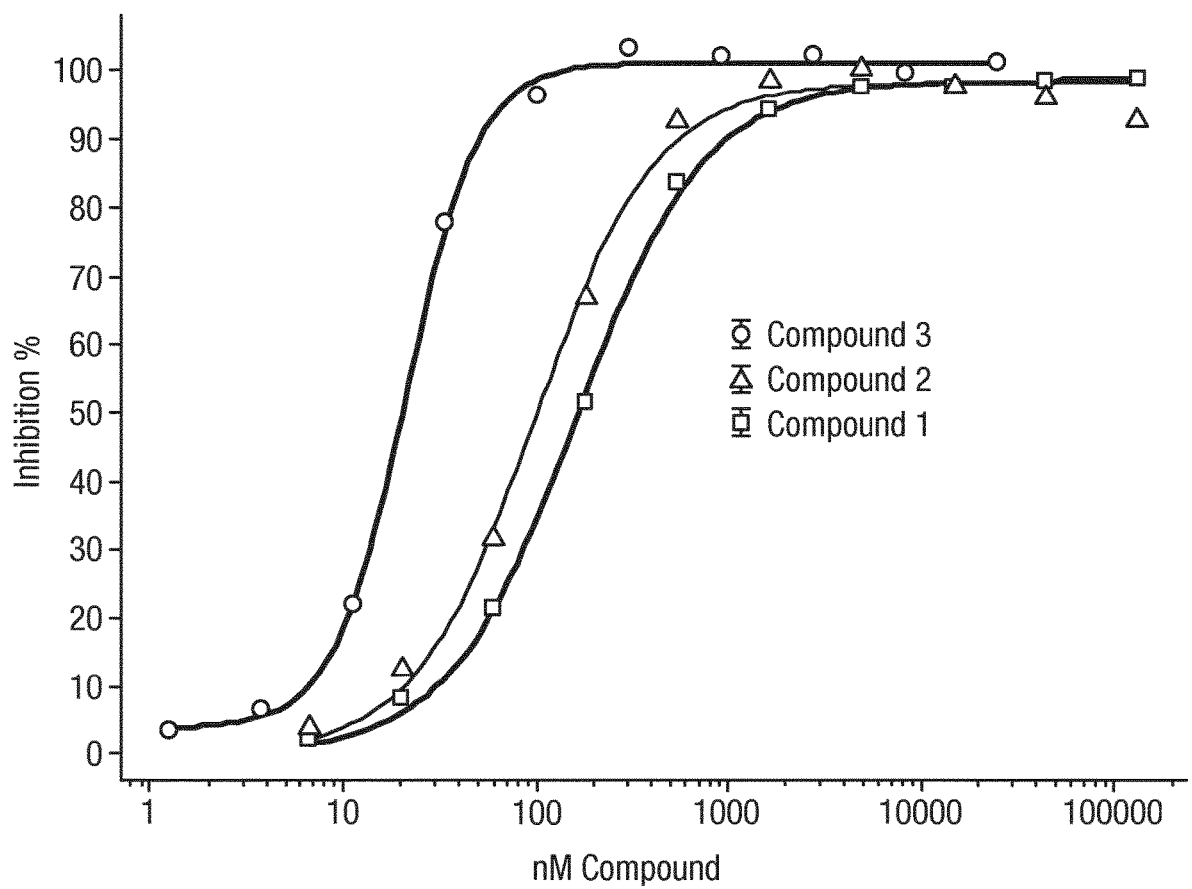
FIG. 16 is a graph of the results of a fluorescence polarization (FP) assay using test compounds of formula (1), (2) and (3). Concentrations of the test compound are plotted against the % inhibition of binding of the compound of formula (4) to TNFα.

The results are illustrated graphically in FIG. 16. The compound of formula (1) was able to inhibit binding of the compound of formula (4) to TNFα with an $IC_{50}$ value of 167 nM.

The experiment was repeated using the compounds of formula (2) and (3). The compound of formula (2) was able to inhibit binding of the compound of formula (4) to TNFα with an $IC_{50}$ value of 102 nM. The compound of formula (3) was able to inhibit binding of the compound of formula (4) to TNFα with an $IC_{50}$ value of 20 nM.

Example 17—Preliminary Studies with Other Members of the TNF Superfamily

Figure 17:
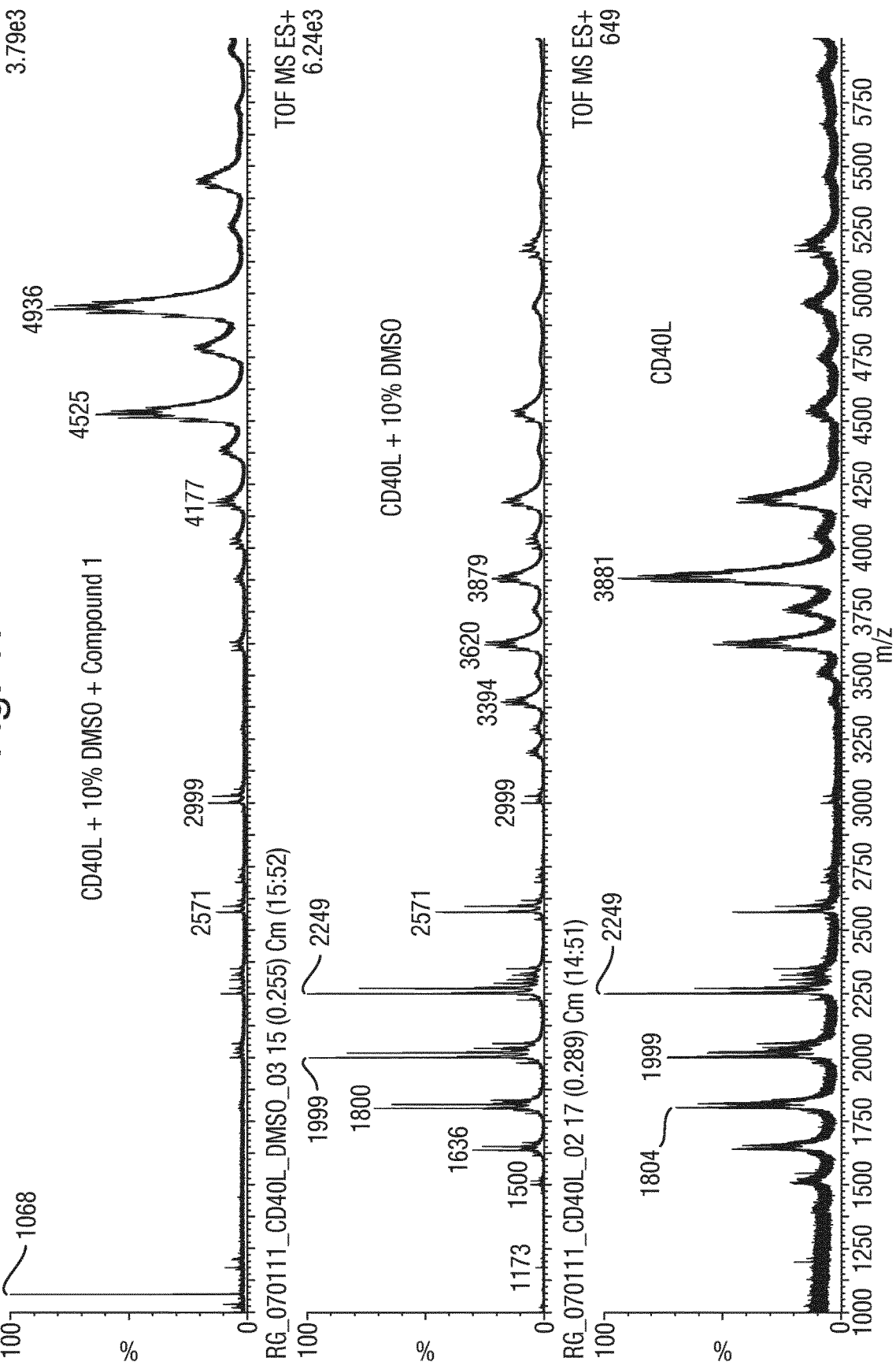
FIG. 17 (bottom trace) shows the mass spectrogram of CD40L in 100% aqueous solution.

Mass spectrometric analysis has shown that CD40L, which also forms homotrimers, is destabilised by DMSO, resulting in a reduced amount of the trimeric CD40L. The assay protocol used was the same as that described in Example 3 for TNFα, but using CD40L instead. The compound of formula (1) has been shown to stabilise trimeric CD40L in the presence of DMSO (FIG. 17). This indicates that the mass spectrometric techniques applied to the study of TNFα, its conformation in the presence of destabilising agents and the effects of compounds according to the invention are applicable to other members of the TNF superfamily.

Example 18—Compounds and Complexes of Ma et al (2014) and Silvian et al (2011) have Different Characteristics to Those of the Present Invention As described on page 12458 of Ma et al. (2014) JBC 289:12457-12466, C87 was discovered through virtual screening by attempting to find molecules which fit the space occupied by a 7 amino-acid peptide from loop2/domain2 of TNFR1 in its interaction with the external surface of TNFβ. The C87 compound from Ma et al. and the BIO8898 compound from Silvian et al. (2011) ACS Chemical Biology 6:636-647 were tested by the present inventors.

Summary of Findings

The Biacore observations described in Ma et al. for C87 could not be repeated.

No evidence of TNF specific inhibition in cells was observed.

Additionally C87 was not observed to bind by mass spectrometry, which is sensitive to millimolar affinities.

Extensive crystallography trials only produced apo-TNF (TNF without compound).

In the fluorescence polarisation (FP) assay, C87 showed no significant inhibition above the interference level of the compound with the fluorescent read-out.

Thermofluor, which measures stabilisation of the thermal melting temperature of TNFα, did show a small stabilisation for C87.

In summary, no evidence was found that C87 binds in the centre of the trimer. The overwhelming majority of the data suggested no direct interaction with TNFα. BIO8898 was also found not to bind to TNFα.

Cells—TNF Induced HEK NFKB Reporter Gene Assay

C87 was preincubated with TNFα for 1 hour prior to the addition to HEK-293 cells stably transfected with SEAP under the control of NFκB. An appropriate counter-screen was also tested in order to detect non-TNF related (off target) activity. The assay was incubated overnight before inhibition was measured compared to 100% blocking by a control compound. The maximum C87 concentration was 10,000 nM, with a 3-fold serial dilution.

No inhibitory effect could be detected that could not be attributed to off-target activity.

Biacore

TNF was immobilised using an avi-tag linker and C87 was passed over the chip. In one experiment, a dose response of C87 from a highest concentration of 10 μM was performed. No binding was observed.

In a second experiment, the flow rate of C87 passing over the chip was reduced. A small shift was observed but overall binding was negligible.

The binding of C87 to TNF described in Ma et al was likely to be super-stoichiometric based on the RU value on the Y-axis. At standard TNF density on the chip this value was in the region of thirty times higher than expected for simple 1:1 binding.

In another experiment, BIO8898 was tested against the immobilised soluble form of CD40L and the soluble form of TNFα by SPR on a Biacore 4000 machine. A geomean IC50 of 17 μM was determined for binding against CD40L whereas no binding was detected at a concentration of up to 100 μM for TNFα in this assay.

Mass Spectrometry

There was no evidence of C87 binding to human TNFα (20 μM) at a concentration of 400 μM. A species of lower molecular weight (~473 Da appears to bind at less than 5% occupancy). C87 has a molecular weight of 503 Da. Based on the occupancy at a concentration of 400 μM, an affinity of the low molecular weight species in excess of 1 mM is predicted.

Crystallography

Overall a large effort was put into crystallising C87 with TNFα, including testing conditions that routinely work with compounds described in the present application. This comprised setting up a large number of crystallization trials at different ligand concentrations, different protein concentrations, and different soaking times. A few crystals were observed that, on analysis, proved to be salt or TNF with no compound.

Fluorescent Polarization (FP)

C87 was preincubated with TNFα for 1 hour prior to assay against the fluorescent compound (probe). Competition with the fluorescent compound either directly (binding at the same site) or indirectly (disrupting TNF) is detected by a reduction in FP.

Extrapolation of the inhibition curve produced an IC50 of about 100 μM. Fluorescence quenching was, however, observed at the highest concentrations of inhibitor which, when subtracted, resulted in negligible inhibition of C87 in this assay.

Thermofluor

Thermofluor measures the change of melting temperature (Tm) of TNFα due to compound either stabilising or disrupting the protein. A stabilization effect of 3.8° C. was observed at a concentration of 500 μM C87, suggesting the possibility of weak binding, which may not be specific.

Sequence listing

SEQ ID NO: 1 (HCVR of 1974)
DVQLVESGGGLVQPGRSLKLSCAASGFTFSAYYMAWVRQAPTKGLEWVAS
INYDGANTFYRDSVKGRFTVSRDNARSSLYLQMDSLRSEDTATYYCTTEA
YGYNSNWFGYWGQGTLVTVSS

SEQ ID NO: 2 (LCVR of 1974)
DIQMTQSPASLPASPEEIVTITCQASQDIGNWLSWYQQKPGKSPQLLIYG
ATSLADGVPSRFSASRSGTQYSLKISRLQVEDFGIFYCLQGQSTPYTFGA
GTKLELK

SEQ ID NO: 3 (1974 HC mIgG1 full)
DVQLVESGGGLVQPGRSLKLSCAASGFTFSAYYMAWVRQAPTKGLEWVAS
INYDGANTFYRDSVKGRFTVSRDNARSSLYLQMDSLRSEDTATYYCTTEA
YGYNSNWFGYWGQGTLVTVSSAKTTPPSVYPLAPGSAAQTNSMVTLGCLV
KGYFPEPVTVTWNSGSLSSGVHTFPAVLQSDLYTLSSSVTVPSSTWPSET
VTCNVAHPASSTKVDKKIVPRDCGCKPCICTVPEVSSVFIFPPKPKDVLT
ITLTPKVTCVVVDISKDDPEVQFSWFVDDVEVHTAQTQPREEQFNSTFRS
VSELPIMHQDWLNGKEFKCRVNSAAFPAPIEKTISKTKGRPKAPQVYTIP
PPKEQMAKDKVSLTCMITDFFPEDITVEWQWNGQPAENYKNTQPIMDTDG
SYFVYSKLNVQKSNWEAGNTFTCSVLHEGLHNHHTEKSLSHSPGK SEQ ID NO: 4 (1974 LC kappa full)
DIQMTQSPASLPASPEEIVTITCQASQDIGNWLSWYQQKPGKSPQLLIYG
ATSLADGVPSRFSASRSGTQYSLKISRLQVEDFGIFYCLQGQSTPYTFGA
GTKLELKRTDAAPTVSIFPPSSEQLTSGGASVVCFLNNFYPKDINVKWKI
DGSERQNGVLNSWTDQDSKDSTYSMSSTLTLTKDEYERHNSYTCEATHKT
STSPIVKSFNRNEC SEQ ID NO: 5 (HCVR of 1979)
EVHLVESGPGLVKPSQSLSLTCSVTGYSITNSYWDWIRKFPGNKMEWMGY
INYSGSTGYNPSLKSRISISRDTSNNQFFLQLNSITTEDTATYYCARGTY
GYNAYHFDYWGRGVMVTVSS SEQ ID NO: 6 (LCVR of 1979)
DIQMTQSPASLSASLEEIVTITCQASQDIGNWLSWYQQKPGKSPHLLIYG
TTSLADGVPSRFSGSRSGTQYSLKISGLQVADIGIYVCLQAYSTPFTFGS
GTKLEIK SEQ ID NO: 7 (1979 HC mIgG1 full)
EVHLVESGPGLVKPSQSLSLTCSVTGYSITNSYWDWIRKFPGNKMEWMGY
INYSGSTGYNPSLKSRISISRDTSNNQFFLQLNSITTEDTATYYCARGTY
GYNAYHFDYWGRGVMVTVSSAKTTPPSVYPLAPGSAAQTNSMVTLGCLVK
GYFPEPVTVTWNSGSLSSGVHTFPAVLQSDLYTLSSSVTVPSSTWPSETV
TCNVAHPASSTKVDKKIVPRDCGCKPCICTVPEVSSVFIFPPKPKDVLTI
TLTPKVTCVVVDISKDDPEVQFSWFVDDVEVHTAQTQPREEQFNSTFRSV
SELPIMHQDWLNGKEFKCRVNSAAFPAPIEKTISKTKGRPKAPQVYTIPP
PKEQMAKDKVSLTCMITDFFPEDITVEWQWNGQPAENYKNTQPIMDTDGS
YFVYSKLNVQKSNWEAGNTFTCSVLHEGLHNHHTEKSLSHSPGK SEQ ID NO: 8 (1979 LC Kappa full)
DIQMTQSPASLSASLEEIVTITCQASQDIGNWLSWYQQKPGKSPHLLIYG
TTSLADGVPSRFSGSRSGTQYSLKISGLQVADIGIYVCLQAYSTPFTFGS
GTKLEIKRTDAAPTVSIFPPSSEQLTSGGASVVCFLNNFYPKDINVKWKI
DGSERQNGVLNSWTDQDSKDSTYSMSSTLTLTKDEYERHNSYTCEATHKT
STSPIVKSFNRNEC

The invention claimed is:

1. A method for identifying a compound that is capable of binding to trimeric TNFα or CD40L, whereby the compound-trimer complex binds to the requisite TNF superfamily receptor and modulates the signalling of the receptor, comprising:
 a) performing a receptor-ligand binding assay in which a sample of the TNFα or CD40L trimers and the compound is applied to the requisite TNF receptor;
 b) comparing the binding of the TNFα or CD40L trimer-compound complex to the requisite TNF receptor with a control sample, wherein the control sample comprises TNFα or CD40L trimers in the absence of compound; and
 c) selecting a compound that enhances the binding of the TNFα or CD40L trimers to the receptor compared to the binding of the TNFα or CD40L trimers to the receptor in the control sample, and wherein the method further comprises contacting the requisite receptors with both the TNFα or CD40L and the compound-trimer complex and detecting whether the test compound prevents or reduces the TNFα or CD40L trimer signaling through the requisite TNF superfamily receptor.

2. The method of claim 1, wherein the identifying further comprises:

a) conducting a mass spectrometric analysis on a sample containing the TNFα or CD40L and the compound to detect the amount of the TNF Guperfamily member TNFα or CD40L trimer; and b) comparing the amount of TNFα or CD40L trimer in the sample with a control sample, wherein if the trimer is detected in the sample, the compound is identified as capable of binding to the trimer.

3. The method of claim 1, wherein the requisite TNF receptor has been bound to a surface.

4. The method of claim 1, wherein the identifying further comprises:

a) performing an assay to determine the thermal transition midpoint (Tm) of the trimeric form of the TNFα or CD40L in a sample of the TNF TNFα or CD40L and the compound;

b) comparing the Tm of the trimeric form of the TNFα or CD40L in the sample with a control sample in the absence of compound; and c) selecting a compound that increases the Tm of the trimeric form of the TNFα or CD40L compared to the Tm of the trimeric form of the TNFα or CD40L in the absence of the compound.

5. The method of claim 1, wherein the identifying further comprises:

a) performing a fluorescence polarization assay using the compound and a probe compound;

b) comparing the degree of polarization of the probe compound in the presence of the compound with the degree of polarization in a control sample, wherein a higher degree of polarization with the compound identifies the compound as capable of binding to the trimer; and c) selecting a compound that modulates the signalling of the receptor.

6. The method of claim 1, wherein the sample containing the TNFα or CD40L and the compound further comprises a destabilising agent.

7. The method of claim 6, wherein the destabilising agent is dimethyl sulfoxide (DMSO).

8. The method of claim 1, which comprises performing an isothermal calorimetric analysis to measure the binding of the TNFα or *CD*40*L* for the requisite receptor.

9. The method of claim 1, which comprises measuring the binding affinity of trimeric TNFα or CD40L to the requisite receptor in a sample comprising the compound.

10. The method of claim 9, which comprises:

a) performing an assay to determine the binding affinity for a superfamily receptor (KD-r) of the trimeric form of the TNFα or CD40L in a sample of the TNF superfamily member TNFα or CD40L and the compound;

b) comparing the KD-r of the trimeric form of the TNFα or CD40L in the sample with a control sample; and c) selecting a compound that increases the binding affinity of the to the requisite receptor compared to the binding affinity of the TNFα or CD40L to its receptor in the absence of the compound.

11. The method of claim 4, wherein the increase in stability results in an increase in the Tm of the trimeric form of the TNFα or CD40L of at least 1° C.

12. The method of claim 10, wherein the compound increases the binding affinity of the TNFα or CD40L to the requisite receptor by increasing the on rate (kon-r) and/or decreasing the off rate (koff-r) compared to the kon-r and koff-r values for binding of the TNFα or CD40L to its receptor in the absence of the compound.

13. The method of claim 10, wherein the compound increases the binding affinity of the TNFα or CD40L to the requisite receptor by increasing the on rate (kon-r) compared to the kon-r value for binding of the TNFα or CD40L to its receptor in the absence of the compound.

14. The method of claim 10, wherein the compound decreases the KD-r of the TNFα or CD40L to the requisite receptor compared to the KD-r of the TNFα or CD40L to its receptor in the absence of the compound, wherein:

a) the compound decreases the KD-r of the TNFα or CD40L to the requisite receptor by at least 10 times compared to the KD-r of the TNFα or CD40L to its receptor in the absence of the compound;

b) the KD-r value of the TNFα or CD40L for binding to the requisite receptor in the presence of the compound is less than 10 nM.

15. The method of claim 10, wherein the compound decreases the KD-r of the TNFα or CD40L to the requisite receptor compared to the KD-r of the TNFα or CD40L to its receptor in the absence of the compound, wherein:

a) the compound decreases the KD-r of the TNFα or CD40L to the requisite receptor by at least 4 times compared to the KD-r of the TNFα or CD40L to its receptor in the absence of the compound;

b) the KD-r value of the TNFα or CD40L for binding to the requisite receptor in the presence of the compound is less than 600 pM.

16. The method of claim 15, wherein the KD-r value of the TNFα or CD40L for binding to the requisite receptor in the presence of the compound is less than 200 pM.

17. The method of claim 1, wherein said compound has an IC50 value of 500 nM or less.

* * * * *

SEQUENCE LISTING

```
<160> NUMBER OF SEQ ID NOS: 8

<210> SEQ ID NO 1
<211> LENGTH: 121
<212> TYPE: PRT
<213> ORGANISM: Artificial Sequence
<220> FEATURE:
<223> OTHER INFORMATION: HCVR of 1974

<400> SEQUENCE: 1

Asp Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Ala Tyr
                20                  25                  30

Tyr Met Ala Trp Val Arg Gln Ala Pro Thr Lys Gly Leu Glu Trp Val
            35                  40                  45
```

Ala Ser Ile Asn Tyr Asp Gly Ala Asn Thr Phe Tyr Arg Asp Ser Val
          50                  55                  60

Lys Gly Arg Phe Thr Val Ser Arg Asp Asn Ala Arg Ser Ser Leu Tyr
 65                  70                  75                  80

Leu Gln Met Asp Ser Leu Arg Ser Glu Asp Thr Ala Thr Tyr Tyr Cys
                 85                  90                  95

Thr Thr Glu Ala Tyr Gly Tyr Asn Ser Asn Trp Phe Gly Tyr Trp Gly
             100                 105                 110

Gln Gly Thr Leu Val Thr Val Ser Ser
         115                 120

<210> SEQ ID NO 2
<211> LENGTH: 107
<212> TYPE: PRT
<213> ORGANISM: Artificial Sequence
<220> FEATURE:
<223> OTHER INFORMATION: LCVR of 1974

<400> SEQUENCE: 2

Asp Ile Gln Met Thr Gln Ser Pro Ala Ser Leu Pro Ala Ser Pro Glu
 1               5                  10                  15

Glu Ile Val Thr Ile Thr Cys Gln Ala Ser Gln Asp Ile Gly Asn Trp
             20                  25                  30

Leu Ser Trp Tyr Gln Gln Lys Pro Gly Lys Ser Pro Gln Leu Leu Ile
         35                  40                  45

Tyr Gly Ala Thr Ser Leu Ala Asp Gly Val Pro Ser Arg Phe Ser Ala
     50                  55                  60

Ser Arg Ser Gly Thr Gln Tyr Ser Leu Lys Ile Ser Arg Leu Gln Val
 65                  70                  75                  80

Glu Asp Phe Gly Ile Phe Tyr Cys Leu Gln Gly Gln Ser Thr Pro Tyr
                 85                  90                  95

Thr Phe Gly Ala Gly Thr Lys Leu Glu Leu Lys
             100                 105

<210> SEQ ID NO 3
<211> LENGTH: 445
<212> TYPE: PRT
<213> ORGANISM: Artificial Sequence
<220> FEATURE:
<223> OTHER INFORMATION: 1974 HC mIgG1 full

<400> SEQUENCE: 3

Asp Val Gln Leu Val Glu Ser Gly Gly Leu Val Gln Pro Gly Arg
 1               5                  10                  15

Ser Leu Lys Leu Ser Cys Ala Ala Ser Gly Phe Thr Phe Ser Ala Tyr
             20                  25                  30

Tyr Met Ala Trp Val Arg Gln Ala Pro Thr Lys Gly Leu Glu Trp Val
         35                  40                  45

Ala Ser Ile Asn Tyr Asp Gly Ala Asn Thr Phe Tyr Arg Asp Ser Val
     50                  55                  60

Lys Gly Arg Phe Thr Val Ser Arg Asp Asn Ala Arg Ser Ser Leu Tyr
 65                  70                  75                  80

Leu Gln Met Asp Ser Leu Arg Ser Glu Asp Thr Ala Thr Tyr Tyr Cys
                 85                  90                  95

Thr Thr Glu Ala Tyr Gly Tyr Asn Ser Asn Trp Phe Gly Tyr Trp Gly
             100                 105                 110

Gln Gly Thr Leu Val Thr Val Ser Ser Ala Lys Thr Thr Pro Pro Ser
         115                 120                 125

Val Tyr Pro Leu Ala Pro Gly Ser Ala Ala Gln Thr Asn Ser Met Val
            130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
            165                 170                 175

Val Leu Gln Ser Asp Leu Tyr Thr Leu Ser Ser Ser Val Thr Val Pro
            180                 185                 190

Ser Ser Thr Trp Pro Ser Glu Thr Val Thr Cys Asn Val Ala His Pro
            195                 200                 205

Ala Ser Ser Thr Lys Val Asp Lys Lys Ile Val Pro Arg Asp Cys Gly
            210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
            245                 250                 255

Val Thr Cys Val Val Val Asp Ile Ser Lys Asp Asp Pro Glu Val Gln
            260                 265                 270

Phe Ser Trp Phe Val Asp Asp Val Glu Val His Thr Ala Gln Thr Gln
            275                 280                 285

Pro Arg Glu Glu Gln Phe Asn Ser Thr Phe Arg Ser Val Ser Glu Leu
            290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
            325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
            355                 360                 365

Asp Phe Phe Pro Glu Asp Ile Thr Val Glu Trp Gln Trp Asn Gly Gln
            370                 375                 380

Pro Ala Glu Asn Tyr Lys Asn Thr Gln Pro Ile Met Asp Thr Asp Gly
385                 390                 395                 400

Ser Tyr Phe Val Tyr Ser Lys Leu Asn Val Gln Lys Ser Asn Trp Glu
            405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
            435                 440                 445

<210> SEQ ID NO 4
<211> LENGTH: 214
<212> TYPE: PRT
<213> ORGANISM: Artificial Sequence
<220> FEATURE:
<223> OTHER INFORMATION: 1974 LC kappa full

<400> SEQUENCE: 4

Asp Ile Gln Met Thr Gln Ser Pro Ala Ser Leu Pro Ala Ser Pro Glu
1               5                   10                  15

Glu Ile Val Thr Ile Thr Cys Gln Ala Ser Gln Asp Ile Gly Asn Trp
            20                  25                  30

Leu Ser Trp Tyr Gln Gln Lys Pro Gly Lys Ser Pro Gln Leu Leu Ile
            35                  40                  45

```
Tyr Gly Ala Thr Ser Leu Ala Asp Gly Val Pro Ser Arg Phe Ser Ala
            50                  55                  60

Ser Arg Ser Gly Thr Gln Tyr Ser Leu Lys Ile Ser Arg Leu Gln Val
 65                 70                  75                  80

Glu Asp Phe Gly Ile Phe Tyr Cys Leu Gln Gly Gln Ser Thr Pro Tyr
                85                  90                  95

Thr Phe Gly Ala Gly Thr Lys Leu Glu Leu Lys Arg Thr Asp Ala Ala
            100                 105                 110

Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Lys Asp Ile
            130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
                180                 185                 190

Thr Cys Glu Ala Thr His Lys Thr Ser Thr Ser Pro Ile Val Lys Ser
                195                 200                 205

Phe Asn Arg Asn Glu Cys
    210

<210> SEQ ID NO 5
<211> LENGTH: 120
<212> TYPE: PRT
<213> ORGANISM: Artificial Sequence
<220> FEATURE:
<223> OTHER INFORMATION: HCVR of 1979

<400> SEQUENCE: 5

Glu Val His Leu Val Glu Ser Gly Pro Gly Leu Val Lys Pro Ser Gln
 1               5                  10                  15

Ser Leu Ser Leu Thr Cys Ser Val Thr Gly Tyr Ser Ile Thr Asn Ser
                20                  25                  30

Tyr Trp Asp Trp Ile Arg Lys Phe Pro Gly Asn Lys Met Glu Trp Met
            35                  40                  45

Gly Tyr Ile Asn Tyr Ser Gly Ser Thr Gly Tyr Asn Pro Ser Leu Lys
        50                  55                  60

Ser Arg Ile Ser Ile Ser Arg Asp Thr Ser Asn Asn Gln Phe Phe Leu
 65                 70                  75                  80

Gln Leu Asn Ser Ile Thr Thr Glu Asp Thr Ala Thr Tyr Tyr Cys Ala
                85                  90                  95

Arg Gly Thr Tyr Gly Tyr Asn Ala Tyr His Phe Asp Tyr Trp Gly Arg
            100                 105                 110

Gly Val Met Val Thr Val Ser Ser
            115                 120

<210> SEQ ID NO 6
<211> LENGTH: 107
<212> TYPE: PRT
<213> ORGANISM: Artificial Sequence
<220> FEATURE:
<223> OTHER INFORMATION: LCVR of 1979

<400> SEQUENCE: 6

Asp Ile Gln Met Thr Gln Ser Pro Ala Ser Leu Ser Ala Ser Leu Glu
```

```
1               5                   10                  15
Glu Ile Val Thr Ile Thr Cys Gln Ala Ser Gln Asp Ile Gly Asn Trp
                20                  25                  30

Leu Ser Trp Tyr Gln Gln Lys Pro Gly Lys Ser Pro His Leu Leu Ile
            35                  40                  45

Tyr Gly Thr Thr Ser Leu Ala Asp Gly Val Pro Ser Arg Phe Ser Gly
        50                  55                  60

Ser Arg Ser Gly Thr Gln Tyr Ser Leu Lys Ile Ser Gly Leu Gln Val
65                  70                  75                  80

Ala Asp Ile Gly Ile Tyr Val Cys Leu Gln Ala Tyr Ser Thr Pro Phe
                85                  90                  95

Thr Phe Gly Ser Gly Thr Lys Leu Glu Ile Lys
                100                 105

<210> SEQ ID NO 7
<211> LENGTH: 444
<212> TYPE: PRT
<213> ORGANISM: Artificial Sequence
<220> FEATURE:
<223> OTHER INFORMATION: 1979 HC mIgG1 full

<400> SEQUENCE: 7

Glu Val His Leu Val Glu Ser Gly Pro Gly Leu Val Lys Pro Ser Gln
1               5                   10                  15

Ser Leu Ser Leu Thr Cys Ser Val Thr Gly Tyr Ser Ile Thr Asn Ser
                20                  25                  30

Tyr Trp Asp Trp Ile Arg Lys Phe Pro Gly Asn Lys Met Glu Trp Met
            35                  40                  45

Gly Tyr Ile Asn Tyr Ser Gly Ser Thr Gly Tyr Asn Pro Ser Leu Lys
        50                  55                  60

Ser Arg Ile Ser Ile Ser Arg Asp Thr Ser Asn Asn Gln Phe Phe Leu
65                  70                  75                  80

Gln Leu Asn Ser Ile Thr Thr Glu Asp Thr Ala Thr Tyr Tyr Cys Ala
                85                  90                  95

Arg Gly Thr Tyr Gly Tyr Asn Ala Tyr His Phe Asp Tyr Trp Gly Arg
                100                 105                 110

Gly Val Met Val Thr Val Ser Ser Ala Lys Thr Thr Pro Pro Ser Val
            115                 120                 125

Tyr Pro Leu Ala Pro Gly Ser Ala Ala Gln Thr Asn Ser Met Val Thr
        130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Glu Thr Val Thr Cys Asn Val Ala His Pro Ala
        195                 200                 205

Ser Ser Thr Lys Val Asp Lys Lys Ile Val Pro Arg Asp Cys Gly Cys
210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
```

```
                260                 265                 270
Ser Trp Phe Val Asp Asp Val Glu Val His Thr Ala Gln Thr Gln Pro
            275                 280                 285

Arg Glu Glu Gln Phe Asn Ser Thr Phe Arg Ser Val Ser Glu Leu Pro
        290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
        355                 360                 365

Phe Phe Pro Glu Asp Ile Thr Val Glu Trp Gln Trp Asn Gly Gln Pro
370                 375                 380

Ala Glu Asn Tyr Lys Asn Thr Gln Pro Ile Met Asp Thr Asp Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
            420                 425                 430

His Thr Glu Lys Ser Leu Ser His Ser Pro Gly Lys
        435                 440

<210> SEQ ID NO 8
<211> LENGTH: 214
<212> TYPE: PRT
<213> ORGANISM: Artificial Sequence
<220> FEATURE:
<223> OTHER INFORMATION: 1979 LC Kappa full

<400> SEQUENCE: 8

Asp Ile Gln Met Thr Gln Ser Pro Ala Ser Leu Ser Ala Ser Leu Glu
1               5                   10                  15

Glu Ile Val Thr Ile Thr Cys Gln Ala Ser Gln Asp Ile Gly Asn Trp
            20                  25                  30

Leu Ser Trp Tyr Gln Gln Lys Pro Gly Lys Ser Pro His Leu Leu Ile
        35                  40                  45

Tyr Gly Thr Thr Ser Leu Ala Asp Gly Val Pro Ser Arg Phe Ser Gly
    50                  55                  60

Ser Arg Ser Gly Thr Gln Tyr Ser Leu Lys Ile Ser Gly Leu Gln Val
65                  70                  75                  80

Ala Asp Ile Gly Ile Tyr Val Cys Leu Gln Ala Tyr Ser Thr Pro Phe
                85                  90                  95

Thr Phe Gly Ser Gly Thr Lys Leu Glu Ile Lys Arg Thr Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
```

```
                180              185              190
Thr Cys Glu Ala Thr His Lys Thr Ser Thr Ser Pro Ile Val Lys Ser
        195                      200              205
Phe Asn Arg Asn Glu Cys
    210
```

UNITED STATES PATENT AND TRADEMARK OFFICE
CERTIFICATE OF CORRECTION

| | |
|---|---|
| PATENT NO. | : 11,448,655 B2 |
| APPLICATION NO. | : 16/883859 |
| DATED | : September 20, 2022 |
| INVENTOR(S) | : James Philip O'Connell et al. |

It is certified that error appears in the above-identified patent and that said Letters Patent is hereby corrected as shown below:

In the Claims

Claim 2, Column 55, Lines 38-41: replace "a) conducting a mass spectrometric analysis on a sample containing the TNFα or CD40L and the compound to detect the amount of the TNF Guperfamily member TNFα or CD40L trimer; and" with -- a) conducting a mass spectrometric analysis on a sample containing the TNFα or CD40L and the compound to detect the amount of the TNFα or CD40L trimer; and --

Claim 4, Column 55, Lines 50-53: replace "a) performing an assay to determine the thermal transition 50 midpoint (Tm) of the trimeric form of the TNFα or CD40L in a sample of the TNF TNFα or CD40L and the compound;" with -- a) performing an assay to determine the thermal transition 50 midpoint (Tm) of the trimeric form of the TNFα or CD40L in a sample of the TNFα or CD40L and the compound; --

Claim 10, Column 56, Lines 28-32: replace "a) performing an assay to determine the binding affinity for a superfamily receptor (KD-r) of the trimeric form of the TNFα or CD40L in a sample of the TNF superfamily member TNFα or CD40L and the compound;" with -- a) performing an assay to determine the binding affinity for a superfamily receptor (KD-r) of the trimeric form of the TNFα or CD40L in a sample of the TNFα or CD40L and the compound; --

Claim 10, Column 56, Lines 35-38: replace "c) selecting a compound that increases the binding affinity of the to the requisite receptor compared to the binding affinity of the TNFα or CD40L to its receptor in the absence of the compound." with -- c) selecting a compound that increases the binding affinity to the requisite receptor compared to the binding affinity of the TNFα or CD40L to its receptor in the absence of the compound. --

Signed and Sealed this
Twentieth Day of December, 2022

Katherine Kelly Vidal
*Director of the United States Patent and Trademark Office*